United States Patent
Seal et al.

(10) Patent No.: US 11,713,470 B2
(45) Date of Patent: Aug. 1, 2023

(54) TARGETED GENE THERAPIES FOR PAIN AND OTHER NEURO-RELATED DISORDERS

(71) Applicant: University of Pittsburgh—Of the Commonwealth System of Higher Education, Pittsburgh, PA (US)

(72) Inventors: Rebecca Seal, Pittsburgh, PA (US); Cynthia Mary Arokiaraj, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 540 days.

(21) Appl. No.: 16/493,387

(22) PCT Filed: Mar. 20, 2018

(86) PCT No.: PCT/US2018/023364
§ 371 (c)(1),
(2) Date: Sep. 12, 2019

(87) PCT Pub. No.: WO2018/175443
PCT Pub. Date: Sep. 27, 2018

(65) Prior Publication Data
US 2020/0131537 A1   Apr. 30, 2020

Related U.S. Application Data

(60) Provisional application No. 62/473,630, filed on Mar. 20, 2017.

(51) Int. Cl.
| C12N 15/90 | (2006.01) |
| A61K 47/64 | (2017.01) |
| A61K 48/00 | (2006.01) |
| C07K 14/705 | (2006.01) |
| C12N 15/86 | (2006.01) |
| A61K 45/06 | (2006.01) |

(52) U.S. Cl.
CPC .......... *C12N 15/90* (2013.01); *A61K 47/6425* (2017.08); *A61K 48/0075* (2013.01); *C07K 14/705* (2013.01); *C12N 15/86* (2013.01); *A61K 45/06* (2013.01); *C12N 2750/14143* (2013.01); *C12N 2800/30* (2013.01); *C12N 2830/008* (2013.01)

(58) Field of Classification Search
None
See application file for complete search history.

(56) References Cited

U.S. PATENT DOCUMENTS

| 6,093,570 A | 7/2000 | Ferrari et al. |
| 6,458,587 B2 | 10/2002 | Ferrari et al. |
| 6,951,758 B2 | 10/2005 | Ferrari et al. |
| 7,439,065 B2 | 10/2008 | Ferrari et al. |
| 8,435,762 B2 | 5/2013 | Sternson et al. |
| 8,957,036 B2 | 2/2015 | Cascio et al. |
| 2008/0213182 A1* | 9/2008 | Swanson .............. C12N 15/907 800/9 |
| 2008/0255064 A1* | 10/2008 | Attie ...................... G01N 33/74 435/456 |
| 2008/0300202 A1* | 12/2008 | Kentros ............. C12N 15/8509 435/325 |
| 2015/0284362 A1* | 10/2015 | Bersot ...................... A61P 3/04 435/6.12 |
| 2018/0009862 A1* | 1/2018 | Sternson ................ C12N 15/00 |

FOREIGN PATENT DOCUMENTS

| WO | 2010042799 A2 | 4/2010 |
| WO | 2017049252 A1 | 3/2017 |

OTHER PUBLICATIONS

Wells "additivity of mutational effects in proteins" biochem 29(37):8509-8517 (Year: 1990).*
Chhatwal "Identification of cell-type-specific promoters within the brain using lentiviral vectors" gene ther 14(7): 575-583 (Year: 2007).*
Wiesenfeld "The Role of Spinal Cholecystokinin in Chronic Pain States" pharma tox 91:398-403 (Year: 2002).*
Deng "Effects of Endogenous Neurotrophins on Sympathetic Sprouting in the Dorsal Root Ganglia and Allodynia Following Spinal Nerve Injury" exp neuro 164:344-350 (Year: 2000).*
Ayuso, "Manufacturing of recombinant adeno-associated viral vectors: new technologies are welcome", Molecular Therapy, Methods & Clinical Development, 2016, pp. 1-3, vol. 3.
Bierhaus et al., "Methylglyoxal modification of Nav1.8 facilitates nociceptive neuron firing and causes hyperalgesia in diabetic neuropathy", Nature Medicine, 2012, pp. 926-935, vol. 3:6.
Cavanaugh et al., "Distinct subsets of unmyelinated primary sensory fibers mediate behavioral responses to noxious thermal and mechanical stimuli", PNAS, 2009, pp. 9075-9080, vol. 106:22.
Chan et al., "Engineered AAVs for efficient noninvasive gene delivery to the central and peripheral nervous systems", 2017, Nature Neuroscience, 2017, pp. 1172-1181, vol. 20:8.
Chuquilin et al., "Cutaneous neuroanatomy and mechanisms of itch and pain", J Am Acad Dermatol, 2016, pp. 197-212, vol. 74.
Decosterd et al., "Spared nerve injury: an animal model of persistent peripheral neuropathic pain", Pain, 2000, pp. 149-158, vol. 87.

(Continued)

*Primary Examiner* — Adam Weidner
(74) *Attorney, Agent, or Firm* — The Webb Law Firm

(57) ABSTRACT

Provided herein are nucleic acids for expressing modified ligand-gated ion channel proteins in excitable cells or secretory cells, such as nerves and neurons and optionally including viral sequences, such as Adeno-associated virus sequences, for delivery to excitable cells or secretory cells of a patient. Also provided herein are methods of modulating cell membrane potentials in an excitable cell or secretory cell, and for treatment of a disease or disorder associated with the nervous system in a patient, such as chronic pain or itch.

5 Claims, 29 Drawing Sheets
Specification includes a Sequence Listing.

(56) References Cited

OTHER PUBLICATIONS

"Applications & Technologies for DNA synthesis", Gene Synthesis Handbook, Second Edition, 2014, pp. 1-33.
Gompf et al., "Targeted genetic manipulations of neuronal sybtypes using promoter-specific combinatorial AAVs in wild-type animals", Methods, 2016, pp. 1-12, vol. 9:152.
Gray et al., "Production of Recombinant Adeno-Associated Viral Vectors and Use in In Vitro and In Vivo Administration", Curr Protoc Neurosci, 2011, pp. 1-36.
Guo et al., "Rapid and simplified purification of recombinant adeno-associated virus", Journal of Virological Methods, 2012, pp. 139-146, vol. 183.
"*Homo sapiens* chromosome 3, GRCh38.p13 Primary Assembly", Nucleotide, 2019, pp. 1-2, https://www.ncbi.nlm.nih.gov/nuccore/NC_000003.12.
"*Homo sapiens* chromosome 19, GRCh38.p13 Primary Assembly", Nucleotide, 2019, pp. 1-2, https://www.ncbi.nlm.nih.gov/nuccore/568815779/.
Katzel et al., "Chemical-genetic attenuation of focal neocortical seizures", Nature Communications, 2014, pp. 1-9.
Lynagh et al., "An Improved Ivermectin-activated Chloride Channel Receptor for Inhibiting Electrical Activity in Defined Neuronal Populations", The Journal of Biological Chemistry, 2010, pp. 14890-14897, vol. 285:20.
Mangus et al., "Chemical and genetic engineering of selective ligand-ion channel interactions", Science, 2011, pp. 1292-1296, vol. 333:6047.
Merten et al., "Current issues in adeno-associated viral vector production", Gene Therapy, 2005, pp. S51-S61, vol. 12.
NCBI Gene ID: 794, CALB2 calbindin 2 [*Homo sapiens* (human)], updated Dec. 24, 2019, pp. 1-8, https://www.ncbi.nlm.nih.gov/gene/?term=794.
NCBI Gene ID: 885, CCK cholecystokinin [*Homo sapiens* (human)], updated Jan. 13, 2020, pp. 1-9, https://www.ncbi.nlm.nih.gov/gene/?term=885.
NCBI Gene ID: 5582, PRKCG protein kinase C gamma [*Homo sapiens* (human)], updated Jan. 5, 2020, pp. 1-12, https://www.ncbi.nlm.nih.gov/gene/?term=5582.
"pscAAV—MCS Expression Vector", Cell Biolabs, Inc., 2016, pp. 1-9.
Peirs et al., "Dorsal Horn Circuits for Persistent Mechanical Pain", Neuron, 2015, pp. 797-812.
Rogan et al., "Remote Control of Neuronal Signaling", Pharmacol Rev, 2011, pp. 291-315, vol. 63:2.
Roth, "DREADDs for Neuroscientists", Neuron, 2016, pp. 683-694, vol. 89.
Samulski et al., "AAV-Mediated Gene Therapy for Research and Therapeutic Purposes", Annu. Rev. Virol., 2014, pp. 427-451, vol. 1.
Seal et al., "Injury-induced mechanical hypersensitivity requires C-low threshold mechanoreceptors". Nature, 2009, pp. 651-655, vol. 462.
Snowball et al., "Changing channels in pain and epilepsy: Exploiting ion channel gene therapy for disorders of neuronal hyperexcitability", FEBS Letters, 2015, pp. 1620-1634, vol. 589.
Sternson et al., "Chemogenetic Tools to Interrogate Brain Functions", Annu. Rev. Neurosci., 2014, pp. 387-407, vol. 37.
Tervo et al., "A Designer AAV Variant Permits Efficient Retrograde Access to Projection Neurons", Neuron, 2016, pp. 372-382, vol. 92.
Troy, DB Editor, Remington: The Science and Practice of Pharmacy, 21st Ed., Lippincott Williams & Wilkins, 2005, Chapters 39-42, pp. 745-849.
Weir et al., "Using an engineered glutamate-gated chloride channel to silence sensory neurons and treat neuropathic pain at the source". Brain, 2017, pp. 2570-2585, vol. 140.
CALB2 calbindin 2 [*Homo sapiens* (human)], Gene NCBI, updated on Dec. 24, 2019, pp. 1-8.
CCK cholecystokinin [*Homo sapiens* (human)], updated on Jan. 13, 2020, pp. 1-9.
"PRKCG protein kinase C gamma [*Homo sapiens* (human)]", Gene NCBI, updated on Jan. 5, 2020, pp. 1.

\* cited by examiner

Human CCK Promoter: GenBank Reference No. AC018358.20 Gene ID: 885
TTCTAACCGAAAGAAGAAAAATAAAACCCCACGAGATTAAAAATAGTGTGAAAAAAATATCCTAAAGGGAAGACTCC
GTGGGAGAAATGAGAACCCTGGGGAAAGCACTTTTCCAGATAGCTAACAAGCTTTCAATATGGAAATACAGTAAATG
ATGAAAAAGAGAAGCACAGTTTAAAATGTAGGAGCAATAAATAAAGCCGTATTTATAAAGTTTTTCTCAAAGTGTAC
GTGGGAAATGGCAATAAGCCACTACGCAGAACATAGGCAGGTTTTAAAATCAGAAATATGTGCCCAGCGCTCAGGCT
TCGAAAGCCCCGTGCATTTTAGATCGCTAGTGGATAAAACACCCTCAAGTTTCTATCCGTAAAGCCTCGAAATTTTC
TGCAGTATTTAGAAAATGAATTTAAATCTTAAAACCCTCTAATATTTTATTAGAAAAGATTGCAAAGTCCCCCGCAC
CGCTGTGTAACAGCTAGCAAACTCAATCTGCATGCGAATCTTAGCGAATGGGTAGTTCATCCCTTAATGATGCTGGC
GTATGAAAGGCTCTAAAGCAGCTCTACCCACCCAGACCTCACTTTTAGACCCAGAGCCGTTATTTCTGACTTCAAGA
AATGTCTTTCGAGCTCTCGGAGGGAAGACACAGAAATAGAAAAGCATAATGGAAATGGGCACAAAGCTGAAGACAG
CATCCTTCAAAGACACACGACACTTGGATCCCCGCTGACGAACCGAGGGACCTACCTTTTGGATTAGGACGCAGCT
GGCTTGGCGTTTCCAACCGGAGCAGCCCGGCAGCTGAGCCAAGTTCAGGGAGGACCAGCGGGCGGCTGTCTCTTAAA
TAGCCCCACCCGGCGGCGTCGGCCAGTCATGTATTTACCCAACGCTGACGCAGACTGGCAGTAACACGTGCTCAGAG
GGCGGCCACTGGGGCGACAACCGGTTGAAGTGGCTCCTGGGAGAGAGGGGGAGGTGGTCTAGTGGGGTGGAGTTAAT
CCCTCCCACGCGCGGTGCCGGGTGTCCGCCCCTCTGGGTCCGAGAAGCTTCCGCCCAACCCTTTCCAGGTGCCGCT
CCCCTGCGCATTCCAGAGCAGTACTCTCCAAGGTGGGAAACCTAGGAGTTTGGAGTCTCCTCCGGGATGGAGAAGCT
GCCGCTAGCTTAGTTCGCTTTGGGGACCGGAGGGGCTAGAAAGGAAACTGGGGGCGGGGTGGGGGGTGGACACTGG
GCAGGACTGAGCATCAGCAAGGCGTGATTCTGAAAGGGAGGGGGCGTCGGCCCCTACCCCGGAGCGTCCGAGGCGC
TGGTCTTCATACCTGTGTCGGCTCTTTCGAAGGAGAGAGGAGGAGTCGGGGTCTTCACTTTCTTCAGCCGCATTA
AAAGCCCTCGCAGTTCTCCAGGTTTCCGAGGGCCAGTGTTCTGGGTCAGTGAAAGGGCTCTGGCCACAGCTGGCTCT
TGGTGTCCTGGGCCTCTCTTGACGCAGCTGTAAAATGCGGATGACACCATCTGGTTTTGCTCAGAGGAATCCGGTTT
GGGAAAGGGATGTGTTTCTTCCCGGGCCAAGTTACCACCACCCGCGGCGCCCACTGTTCCCCGTTGTCGACAAGCG
GCGCCAGCGAGGGTCCTGGGGAACTTGACCACCGCACCCCCGCAAGCTCGGGTAGACCACGGCATCCGCCCCTCGCA
CCTTTCCTGAGGGCCCACACACTCACACCCCCAGGACAGTACCTTCCAGAACTCAGCTGCGCAGCCTGGAGGTGAGG
ACCTCACCCCTAGTCAGTCACCCGTCCGGTGGAGGGAAGGGAGGCACCGAGGCTGCCGTGCGCCTTTCCCTGCACGC
GGTTACTCTCCCGGCTCCGGAGCGGGCCGACCTGGAGCCCCTCAGTGCGCTCTGGTCGTCTACACCCTGAAACCCTT
TGAGTTCGAGTCCGCTTGCTGGTGCTTGAGTTCGCCGCGTCCCTGCAAAGGCACTGCCAACCCCATTTCACAGACCG
CAAACCGAGGCGCGAGGAAGAGCAGCGCCTTGCCAAGGCTCCACAACACGCCCCTCGCCCTCTCCGTGCACCGAGGC
CGCCCAGCCTGGGACCTGGAGATCACCAGGCCTTGAACCTTGGGACCTCAACTCCTCTCCCTTTCTTTCCCCCACCC
GTCTTAGATGCAAGGAGAAAGATTTAGAAGCGCTTATTTTAAAATCGGAATCCGTATTCCGCTCTGGAATTCCCTCT
GGAATGGAGGGACTGTGGCAACGCCAGTGTGAGGGTGGAGTGGGCGAGGCGGGGTGGGGGGTTGGGGGGCGGCCC
AGAGACGCCTCCGGTTGCTGCTCCACTTTCTAATCCTGAGAGGCAGCTGCGTTTCTGCAACCTATGGGCAACATGTT
TGAAAGAGCTGAAGCTGATTAAATGCTTTCCAGTGGTTTCGCCACGAGCCTGCTAAGGTTTGTGTAGTTCAGTTGCG
AAAAAGAGTCTTATTTGTGATTGTGGCAAGACATGTCTGGAAACATAAACTTGTTATCGAAATACCCCCAGAGCTTC
TAATTCAGTAGGTCTGAGGAAGGGCCCAAGAATCCGAATTCCTTCCTTCCTTCCTTCCTTCCTTCCTTCCTTCCTTC
CTTCCTTTCTTCCTCCTTCCCTCCTTCCCTCCCTCCCTTCCTTCCTCCCTCCCTCCCTTCCTCCCTCCT
TCCCTCCCTCTCTCCCCTTCCCTCTTTCCCTCTCTCCCTTCCTTCCTTCCTTCCTTCCTTCCTTCCTTCCTTC
CCTCCCTCCTTCCTTCCTTCCTTCCCCCCTCCCTCCCTCCGTCTCTCCTTCTCCCTCTTTCCCTCTTTCTCTCTCTC
TTTCTTTCTTTCTTTATTTCTTTCTTTCTTCATTTCCTTCCTTCCTTCCTTCCTTCCTTCCTTCCT
TCCTTCCTTCCTTTCCTTGCCTTTCCTTCTTTGAGACAGAGTCTCACTCTGTCGCCCAGGCTGGAGTACA

*Fig. 1A*

Human Tac1 Promoter  GenBank Reference No. AC004140.2 Gene ID: 6863

```
AAACATAGGTCATAAATATTTAGAAAAAAATGCATCCGTGCTAAACACATACAGACTTTTTCCCTTTGTGTTATTCC
CCACATAATACAGTATAACAACTATTTACACTGCCTTTATATTATATTAAGTATCATAAGTAATCTAGAGATTATTT
AAAATATATGAGACGATGTGCATAGGTTATATTCAAATACCACACCATTTTGCATCAGGGACTTGAGCATCCACAGG
TTTTGATACCTACAGGAGGTCCTACAGCCAATCCCCTATGCATACTGAGTGATGACTGTATGTCAAATGTGTTTAAA
TCCAGGAAGTCATAATAATCCTAATTTTTTAAAGTGGGTCTTATTAAAAGGTGTTAATTTACCAATTCATTATTTTC
AAAATTGGTAGAGAGACATAATCAAGCATTTATCCCATCTTTCCTATATTAATAATGCTTTAGAATAACTAGTTGCT
GAGAAACATGAAAGAAACAAGTCTGCCTACCAGACAAATAATGAATGATAAAATCAACATAGCACTGTTTTGAAAAT
ACTAATGAATTAATAGATCTAGAAAATGATAGTCAATGGCTGCTAACAACTCAAAAGGAGAAACAACCACATATCAT
GTGCTTCCTACCAGAACAACACAACACATGTGAAGTAGTCTCATCAAAAAAAAAAAAAAAGAAAAAGAAAAGGAAAA
AGAAAAAAATGTACAGAGGATCAAACTTCTAGATACAACTACCAATTAACAGGAAATAATCGAAACAGAGAAACAAG
TTAAAAGGCAATCAGCAAAGTCCAGAATGCGGTACACTCTCCTGACCTGTCTTATCAATAAACTACAATAGAGAGAG
AAAGAGAGAGCGAATTACAGATTCAGGGAGATTTAAGAAACATGCAGTAGAAGGAATGTTCGTGTCCCTCCAAAATG
CATGTGTTGAAATCGTAACCCCTAAGGTTATGGTATTAGGAAGTGGGGTCTTTGGAAGATAATTAGATCATGATGGT
GCAGCTCTTATGAATGAGATCAGTGCCCCGATAAAAGGGACTTTGAAGAGCTCTCTCATTCTTTCCTGCCATGTGAG
GATATAACAAGGAGACAATATGACAGTCTGTAACCTGGAAGAGGGCCTTAAACACAACCAGACCATGCTGACACCAC
GATCTCAGACTTCCAACCTTCGAAACTGTGAGAAATAAATTTCTGTTGTTTACGTCACCCAGACCATGGTACTTTCT
TACAGCAGCCTGAACTAACAAAACCAATTGTAATGTATGGACTTCATTATAATTCTGATTTCAAGTAGTAAACTGTG
TGGGCCGGAATTAGGAAGCAATGAGAAATATTTGAATGCTAACTGGATATTTAATGTAAGGAATTATTTTATGTTGT
TTTAGGTGGGATAATGGCGTGGATATGTTTTTATTTTTTTAATTCCTACCTTTATACAGACATGCTGAAATATTTA
CAGTTGAAATGATTAACTGTCTGGGATTTTTTCAAAATAATCTCAGTGCAGAGGAAACTGGAAGGGTTGTAGATGA
AACTTGGAAGTGGATGTTTCTCTCTACTTTTGGATATGCTTATAATTTTCCATATAAAAGTTCTGAAAACGGAAAAT
AAAATGCTCACATTGTGAGGCTAAGGCCAAAAGAAATCAGAGATGCATGAGAATTTCCAAATTCAGGATTATTTAAG
AACAACATAGAGAAAAAAATACTTCTGGTTTGAGTTGCAAAAATTTATTTCTTTTATGCAATATACTAAAAAATCAT
AATTAATTGAAAAATATAATACTTCATATGTAAAGGGGAGAAAACTACTCCACCAAAGATGTCACATCTTTTAATTC
ATTTGGAGATCAAAGAAATGTGTCTGCCAGGCAACCAAGGGCTCATGGAAAGGTGTGGTTTCTGTACAAATGCTATT
TGTCTAATATTTTGTGCTGTTAATGACTGTCCCATTAGCATCTTCACTACACTTACTTTCATAGAAAGGAGAAACAT
GATTTATAGAGCCCTTTAGTGACAAGGGTGAGGATCCTACACACTATGTTGCTGGTTTCCTAGTCTTCAGCAAGAAA
GTGTAGGAGAGAAGCAAAAAACGTCCTGTTCAACCCCTGCTCCTGGATGTGGCAAGGAAGAGGAGTTACCCGGCTTG
AAACAAAAGAAATCCTAAGTCTGACACACAATGTCATGTTTAAATTCCCCTTTCTCCAAAATGTAAAATAAATCTGC
TTCCATCTTCTAAAATACTATGGGACTAAACATCCTTTTGTTATGCTAAGGAAAAGCCAGTATTCGCGTTGATTTAG
AAGAGGGATGTTCTGGTTATAGAACGATGCTGTGTCTCAGAAACACTTAAATACTATTAAGCTAGAAATAGAAGGGA
AAATAATGCTTCCCCGCATCTCCCCTCAAGTGTAGTCCTCTTTTTTAGCCTGATTTCCGACGAAATGTCTGAATGC
CTACAGTTATTTGGCCATCCTGAAAAGTGCAACTTATCCTGACGTCTCGAGGGACGGAAAAGTTACCGAAGTCCAAG
GAATGAGTCACTTTGCTCAAATTTGATGAGTAATATCAGGTGTCATGAAACCCAGTTTCGAAGGAGAGGGGAGGGGG
CGTCAGATCTGCAGACGGAAGCAGGCCGCTCCGGATTGGATGGCGAGACCTCGATTTTCCTAAAATTGCGTCATTTA
GAACCCAATTGGGTCCAGATGTTATGGGCATCGACGAGTTACCGTCTCGGAAACTCTCAATCACGCAAGCGAAGGA
GAGGAGGCGGCTAATTAAATATTGAGCAGAAAGTCGCGTGGGGAGAATGTCACGTGGGTCTGGAGGCTCAAGGAGGC
TGGGATAAATACCGCAAGGCACTGAGCAGGCGAAAGAGCGCGCTCGGACCTCCTTCCCGGCGGCAGCTACCGAGAGT
GCGGAGCGACCAGCGTGCGCTCGGAGGAACCAGAGAACTCAGCACCCCGCGGGACTGTCCGTCGCAGTAAGTGC
```

*Fig. 1B*

Human Nts Promoter GenBank Reference No. NG_047010.1 Gene ID: 4922
GATTATTTTCAGCAATTACCTAATAAAGGTCTGACATAAGTAACAGTACAAGCTTAGAAATCTACCTACTTTAGAGA
TGTTGTAATCAACAGGTACCTAACAGGTAACATCCACTTAAGAAGGCCAACACAGGAATATTATTAAAGGACAATGC
TTAAAATCTTTATCAGATATTTTAAGAACTAGGTAACCCTTAGAAGGATCTAAGGTATGCCGGGCATGGTGGCTCAC
GCCTGTAATCCCAGCACTTTGGGAGGCCGAGGTGGGCGGATCATGAGGTCAAGAGATCGAGACCATCCTGGCCAACA
TGGTGAAACCCCGTCTCTACTAAAAATACAAGAATTAGCTGGGCCTGGTGGTGTGCCTGTAGTCCCAGCTACTCGGG
GGGCTGAGGCAGGAGAGTTGCTTGAACCCAGGAGGTGGAGACTGCAGTGAGCCGAGATCACACCACTGCACTCCAGC
CTGGTGACAGAGAGAAGCTCCATCTCAAAAAAAAAAAAAAAGAAAAAAGAAAAAGGATCTGGGGTAAAAAGCCTTTA
AAATAAAAACAGTTCACCCATCTCCATAGCAAGGTGTCTACAATCCTGCATTAAAGGCATCATTTAGGAAGTTCGTA
GGGTACTTTTTAAGTGGAAAAATACATACTTAACCTTTATCCCTACAACAAATTGTTTTATTGGTTTATGTGTAGCT
TGAAGGCATTAGATTAGAGCAAGAAACAAAAAGCCTAACACATTAAAGAAAATACCAATTAGAGGTCAAAGTTTATC
TACATCATAATTTTACCAAAGTTATACATCTTTTTTCCCCAAAAGAAAAGTAGCATATAGCATCTATTTGAATTTGA
ATTATTTGACATAACTTAATGTTTCCCCTATTCTTGAATATTTATCACATATCTCAATTTTCACATTAACAACTAAT
ATCCATGTTATATATTTAAAATGAATTTCCATTAATTCTTCTCCCCCTTTTTTCTAATTAATTAGGGATCAATTTTG
TCAACATATTGAAGAAATCATCTGAGGAAAATAAGAATCACATTTCCTTTTTACTATTAGACTGCTATCACACATTT
TAAAAGATCATTCTTTGTATTTGCAATTCAAAAGCAGAGAAAACAACTAATTTAATTATCATGCAAAGTATATATAA
TTTTCCCGATTTGTTAATCAAAGTGGCTTTAAGAGGATTCTGTCACAAAGATGCTCTGATAGTAACAGGAAAGTAAG
CACAAATCCTCACTGAGACTCTGTTAAGTGAAAACCAAGTGTTTCAAGCTTCCATTGCTCCCCCTAATGGTAGGAAA
GCAGAAAACATCTAGACGTATGTATTTCACATTTGTCAACTAAATACTTTACAGAAACCTTCCTCCATGTGAGTATG
TTCAATATTGTGTTTTATGTAAGTTCAGAAAACAAACTAAAAGTAATAAATATATCAGTTATTATTAAATTTCTGGT
ATTATATGAAAGACTCCTTGCTATTCTAAGTAATTATTAAATGTTTGGATTTAATCGCTTTGCTTAAGTTTTGGGTA
AAGGTGAAAAAGTTAAACTCATAGATTGTATAATATAAATCAATTATCTATAGGAACCAATCCTATTTTTTCTCAAC
TGTTACTACATGATTGATTTATTTAAAAATTAAACAAGACTCAGACAACTTTACATTCAAATATTCACATCTCTAAC
AGCACTGACTTGTCAAATTACCCCATGTATCTTGAAATGCTTACTACAAGAAGAAAGTTTTACTCTAAAAGGCATTT
TGAACAATTTTCTTTTGAGAACTCAGACAAAGAATGGGTATCAGTGTAACTCATGAAATACATGAAGACTATCATAG
AAAAGTGACTTTGGTGAATGGTGGTTATTTAGGATTGTCTCCTTTCCAAAAGTACAATCTCTTTTTTTATGGTGAAA
AGAGTATTATAACAGGGAAAGAAAGCCGATGCAATAGTAAAAACTGTTGAGAAGGGAATTATACAAAGAGTGAGACA
TGGCATCAAGAATGAATTCAAAAAGAGCAGAAAAATATAGGCATAAAAAGAGATAATGTACAGAAAAAAAGTCAGTG
ATACAACAACACAAATTTTTACCTGCTAGAATGTAAGTAATTTAGAGCTGGATTTTATAAACATGAAATTGTTTTTC
TAATACATTCAACCAAAAGTCAGCACACATAGTTCAGTCATCTCTCATTACTTACAATAAAATATTTCTATTTGTT
AGGAAATAATATCTTATTCCCTGGATCTATTATTTCTTTTATTGATTTCTTTCTATTCTCTAAACTTAATTGCTT
AATTTTTATAACTGATTCTCTGTCTCTATTCCATCTTATTCCAGCATGGATTATTTAAAACCTGTATTAGTTTTGGA
ACCACTAAACATTTGCTCAGAAGTTTGAATTACCAGAGAAGCACCCTAACTCTTCAAGAACTTCCAAGCCTAAGGAA
TCACTGATTTCATGCATTCATCCTGGAGATTTTCCTTAAAAATTAGAAATAACAGATCTCATGTTTCACAAAATCAA
AATGACAACTTTTGGAGTGGGGGAATGAGAAGTGGGAAAAGGATGATACTGGGGGTTCTTTGTCAGTATGCTGTATG
TATGCTGTATGTCAGTGCAGTTGAATGACTCCTTCTGTGCGTCAGAAATCCAAAGCAGCAGCAGCAGCAATTAGGGA
AGATCGTCACTTTCACTCAAGGTTCAGAAATGGGGGAGGAGAGCAGGGGGGACAAAGGAAAAGGGGAGGAGAAAGCA
GGGCAAAGAGGGGAGGGATGGAGGTGAAGATAGGGCACATCCTGCAAAGATAATGTCTGTACAATCAATGACATCAT
CCTCCTGCTTATATATATAGGGGAATGGCCAGAGCACCTCTCATAGTTCACTCACTTTCAAAGCCAGCTGAAGGAAA
GAGGAAGTGCTAGAGAGAGCCCCCTTCAGTGTGCTTCTGACTTTTACGGACTTGGCTTGTTAGAAGGCTGAAAG

*Fig. 1C*

Human Nmu Promoter: GenBank Reference No. AC024243.8 Gene ID: 10874
GGATGTATTAGCTGGTGTCCTGGAAGAGGCTGCTTCCTGAACGTTTCCAATCAAGGAAATAAAGGAAAGTATAGAGA
TGGAAAGAGGGAGTCAGGTCACGGTAGAAATCAGGATGCAATAGCAGCAGAAATGCATAGAAAAAGGAGTTTCCTTA
GGCTTGGAAATCCGTAGGATAACCAGCGCTCCAGACCAGTTAGAAATGTGTGTGTGGTCAAGCCCCAGCAGTCCT
TTCTTCTTTGTCCTTTATTAACAGGCAACTGCATTTCCCTAAGGGGTCTGTGATTTTGCAGGAATTTGGGGGAGGGT
CGATAGCATCAACATCACAGTTGAACCAACACTGCCCTGATATGCACCAGGCATTGCGCTTGGAACTGGGGATAAAC
CGGGGAACAAAACAGAGGTGCTTCCACAGAGGTGCGTACTAGTGACTGCCGGAGCTCTGGAAGAGGTGAAGGAGAAA
GGGTGTCCCACGTAGACCCAGGACACCAGAGAGCGTCGCCACTACCAAGTTTAAAAACTCAGACGGCCTGGTTTGCC
ATCCACACCCTGTTCCCAGTCCAGTCCTTCCAAAGGTGGGAATGGTGCATTATTTAAATTCCATTCTCTTTATCCCA
GAGCGAAAATGCGTGGTACTCGGGTCAGAAACTCAGGCTAGGGGGCTCGGGTCCTGCTGCAGGGTGGGGCGCGGGCA
GGCAGCGGGGCGGGGTGAGGCGAGGTAGGCCGGGGGCGGCAGGCGGCGAGGTGACGCGCGGCGGGGACCGCGCAGCC
CAGCCCACTTGTGCGCGAGATTTAAAAGTTGGCGGCTCGCCGGGCGCTCAGTCCTGTGTCCGGGCCCCGAGGCACAG
CCAGGGCACCAGGTGGAGCACCAGCTACGCGTGGCGCAGCGCAGCGTCCCTAGCACCGAGCCTCCCGCAGCCGCCGA
GATGCTGCGAACAGAGAGCT

Human Calb1 Promoter: GenBank Reference No. AC123779.5 Gene ID: 793
ACAAATTGAAGCAAATAATTTGGAAATGTGTATTAAAATCTAAAATATGCATTCTATTAACTAAAAATACTGCTTTT
GGGACTCTGCCCTGTTGTATTCAGAAACATGTATAGCTAATATAAATGTATAAAGGTGTTTATTGCAGCATTGTGTG
TCACAGTGTACTACTAGAAATAGATCCGTATATCTGTAATTATAGTTAATTAATAAAATATTAAACTGTAAAAAGTA
TACATTAGATGTTGATGTTAATACTGGAGGGATGCCCTTGAATTAATAATAGAAAGTTGAAGGATAATATACAAAAC
ATAGTCCCTTTTCTGTAAAACCAGATAACAACAACAAAAAAAAAAACCTTTAGATATGGATTTGTATATTTCCATAAG
CATGGCTCTTTTAGTGTTGATTACCTCATGGTAGGGGCAGCACTAAACTGCTTTAGAGCTCCATAATCTACATTAGT
TCCCTCAAAAGCCACTTCATATAAACATAAAAAGAACACACAAAAAAAACTATGTCCAAACTTGCTGTTTGGACATA
GTTCCAAGGAAGTCTCCCATTTATTTCTCACTCTCTCTCAAGTCACAGCACCTATACATTTCTAAATGGAAATTTGG
AAGTTGCCATAGCTTCAGGAAAGTGAATAAGAAAAAAGATTACTTTCATATAAATATTTTTAACTTTTACAAATTGT
CTTGTAATACTTTTGGAAGTTAAGATAAAATTCTAAAAAACCAACAAACAGATTATGGTGAAAATGTTTAGGAATTT
TTACCACAGTGTGTGGTCTCTTTTTAGGAAGAAAATTAATTTTAATTACTTTTTAAAATAGTAGAAATGTTGCTCTT
TTTTCATCAGTTTGTTCAGTCCATATTCCTACATACTTTTTCTAGCATTTTTCTTTGTCTCAGAACTGTATCCAAAG
TCTAGACATTGTTAGCTCTGTCAAGACTAGCAAGGGTCAGAGTGATTCTTCAAGTCATTCCTTAGTCACTGCATTCT
CACTCTCTCTTCAAAGTTTATTCTCTAGCGCTGGTCTCCAAGTTCACACACTATATTTTTCACACAGCGACCCTGGC
CACTAACATAGGACCAATAGGACCATCAGTGAGAATCAGATGAGGTATCATAAGTAAAAATAATGTATGAACTGGAA
AGTACTATGGAAGTGAGGATTCCATTAAGAAGATTATTGAAATAGGCTAGCTTCAAATTGATGGGTCTCTGAAAAGG
ATACTTACAAAAAAACTCCACAAATATAATAATGGATAGAGCCCTAATCTCAAAAACATAAATTTGAGGGGTCCCAA
ACTCAATTACACAAGGTTAAGAATATAGAGCTTGGTAAATTCTCTCTCTCTCTTTTTTTTTTGGAGACAGAGTCTT
GCTCTGTCACCAGGCTGGAGTGCAGTGGCGTGATCTTGGCTCACTGCAACCTCCGCCTCCCAGGTTCAAGCCATTCT
CCTGCCTCAGCCTCCCAAGTAGTTCAGATTACAGGTGCCCACCCCCATGCCCAGCTAATTTTTGTATTTTTAGTAGA
GACGGGATTTCACCATGTTGGCCAGGATGGTCTCGATCTCGTGACCTTGTGATCTGCCTGCCTCGGCCTTCCAAAGT
GCTGGGATTACAGGCGTGAGCCACCGCGCCCGGCCGGTAAATTCATTTTAATTCACTTTAAGCTTATATTGGCTATG
TGTAGATTTTCTCTTGTTCCTTCATTTTGTTTTAGTACAATTGTAATTAGACTTTTGGGATACATTTTTAGTGGACT
TCAAGGTCCAAAAGACTCAAAGCCAAATACTCCAGAAGTACTTATGTAAATAAGAAATAATCCAAGTATATAATTAA
TTATATTAAAATACATAACACATATACATATGTATATATAGTACAGAACATATATACATATGTGTGTATACATACAT
ATATATTACATATATATATATATATATATATATATATACATAACATAGCATACATTTAGTTAGATAGCTTTTCCAACTC
TGATGGTGACTTCCAATTTCTGAAAAATTCTCCAGTAGGGGTTGCTTGAAACAGAAAGAAGGAGACGTGTGTGTTAA
GGCGACTGAATGGGGCTGTGGTGGTAGCACTAACGTACCTACTTATGAACCTGGTCAGATCCTTCCTTTCTCTTTGT
TTTAGTTTACTCACTCCTTCTAAACTGAAAGGCAGTAAACTCTAGTATCTGTAAGATGACTTCCTTATCTAAGATTT
TAAGGTTTTATAATTTAACTGTATTACTTTCCAATTATAATTCTACTTCATGCTGAAAAGAAATCCATAATCTAGCT
TTTTTCGTGTTGGCAAGGTAGTTCATAGAAACCATCTTAAGAAACATTGACATGATGGCACAAAATAGAGTGATTA
TTGATAGCAATCAACTCATTGTATACATTAATCAAATTATTCTAATGCGTGCCAAGGTTTCACATGCTTTTTTTTT
TCAAACAAATACTGAAAAGTCTTGGAGAAATCACACAAGAATATAATAATCTTTATGTGATTTTACCCGTCATCAG
CTTTCCCCTTCTATCTGAACATTTAAACCTCTCTAGATAACAAGAGTTTTACTATAATATTCAGGAATAAGATTCTT
CCTGGACTAGGAGGATGTAGGGGGAAATGAGCCTCTGTTTTCAGCATCCAATCTCTGAGCAAAGGATCTCCCACCAC
CTGCTGCTTCCAACAAGCCCAAACTCCGCTCCAGCTAGCTTTCCTGGGAACAGAGCAGAAAACTGGAAGGGAGGGGA
AGAAGGCTGGTGAGAGCAAGAGGCGGGGGTGAGGAATGGGAGGCTGGAGGAGGCGTGGCCCGGCTTGGGCCGTCGG
GAAAATACTGAGAACTGGGTGCGGGGTGTAGGGAGAGAACTCTGGAGGAACGCTAGCTGAGCAGCACCGAGGACAGC
GCCCGGCAGCGCCCGCGCCCAGGTCTCCTCCGCAGCCCTGACTCGCGCACACGCTGAGCTTTTGCTCACT

*Fig. 1D*

Human Parvalbumin Promoter: GenBank Reference No. Z82185.2 Gene ID: 5816

CCAAAGGACTTGGACCTGAAAGTTTGTAGCATTGCAGGGACAGCCATCTTGCCACCCTCAGGGGTCAACCAGTTTGA
GAGAGTGGCACAAGGTATTGCTGAGAAGTAAGAGAAACAGCATCTTCCTGACAGCATTTGAGTTCTGGATCAAACCA
TGCTTGAACCTTCGTGGACTTTTCAGTTGCACGAGTTAGCAAATCCCCCACTGTCTTAAGCCAGCCCAAGTCAGACT
TTCTCATCACTTACAGGCAAAAACAGACCTGACTGATAAACCCATTTTCTGGCATCAAGGCCCTTGTATAATTAACC
AAATTAATAAAATGAAGCCTGCTTCAATCAGCACAGATTCAGAGCAAAAAAACAAACAAACAAAAAAAAAAAAAACT
AGATCATGTTTCCAGATATATGACTCGGGTTTTAGGACATCTCTACCCTACTTTAAGTATTGTAGGGGGAAAGATCC
TCCAGAATCAGAAGTGCTCAGTTTAAATCCTAGCTCTCCCACCTACTTCCTACCTGTGTGACCTTAGGTAAGTCACT
AAACCTCTCTGAGATTCTATTTCTTCGAACGTCTGAGATAAAGCACATAAAGCACTAGGTACGCAGTAGGTGCTCAA
TAAATGCACCCCCCCCCAACACACACACACACACGATATGGTTCAGCCCATTCAGATTTGCTTAATTAGAGGTA
CATGAAGAAGACCTATGGGGACAAAGAGGAAGGCCATCTGGGCTCCTGAGAATTCACCCACAGTAGGTGCTGCTCCC
GTCTTCCGGTCTTATTCTGGAAGCAGGATAGTGTGGTAGAAAGGAGCAAGTGCTTTGGAGTCAGAGAACCGGGGCTG
AAATCCTACCTCCATTCTGTGATCTTAGGCAAGTTGCCCAATCTCTCTGAGCCTTGTTCTTCCATCATTAGTAAAAA
AGAGAGGGTTTTGCCTACCTCTTAAGGGGATACAAGAATCAAAGTGCGATGCTGTGCACACAGAACCCAGCACACTG
TTCAACAAACAAGTGTAATTATTTTCCCAGGCCCCAGCCAGCGATCTTCCTCAAGGGTTCATCCTCAAGGTTCTCCT
GCATCCCGGCTCCCTGAGCTCAGCCATGCCCACGACTTGACGAGATCAACTCCTTGACTTCTCTGATGACAAAGCCC
CCAGGGTCCAGCCCTGACCTCACTCCAGAGTTCAGACACATCTCCGCCAGGGTGTCCTTCAGGTCCCCTAAACCCAG
CATCAGCTCTTGGCTCTTCCACTACTCTCTGGGGGATTTGGGTAAGTCACCCTGGCCTTGGTTTCTTCATCTATAAC
ATGATGTCATTTGTAGAAGTTTGTAGCCGATCACCACGGAGGCTGTCCCAGCCCTAACATCCTAGGATTCAACACCA
CTTACTCTATCATCCCTTCGACTGAGCACTACCTCCTCCCTACACTCCCTGCCTTCAAAGTCAACACCTTCCTTCTT
CAGCAAACCCCACCTTGAATATTTAGGGTCAGCTTGGATTTGTCCCTCTTGTTCATGCCACAGCCCCAATTCTGGAA
GCTTCTCTCCAAGAGGTGCTCCCCTATCTGCACACTCCTTCCTGTTGCCACCACCAGCAACCTAGCTCAGGCCCCAG
CACCACACCTCAAGGAGGCCCCAGTCCCAGCTTCCCCCATGCAGCCTGCCCTCGGCCCTTTCTATCCATGGAGCTTC
CAAACAGCCTTTGCATGGAGCCTGGGATTCCTCGTGTCACTGTGAAGAACTAGACCCCACCATTGACAATCTTCGTG
CCCTGGAGATTCTTTTCAGGTTAGGGATGAGGAGAGGAACATTTCATGGTGGTCAGATTAGATATTCACTACGTATT
TATTGAATTCATTTGGTCATTCATGCTTCTCAAAACACATCCCTCAGCTGGTCCTCTCCAATCCAAAACAGACAATG
TCAGAGATCTCTTTGCAAATCATGAAGGGCTTGGGCCTTTGTGCCTCAATGTCACACGCATACAATTTCAGGGGGTC
CATCTTCCCCTCGCCCTAGACCATCTATAGGGCACAGTTTACCTCTGATTGAGCTCATGTTACAGGTGGAAAGACTG
AGAAAGAGAGAGGAAGGGACTTGTCTGAGAATATGCGGAACATTTCCTTCTACCAGGCACTAGATCCTCGCACAAAA
GTGCTGAGTCCGCTCCCAACCCCAGGCCCGTGGCTTTGAGCAGCAGGTCACTTAACATCTAACGTCTTTATGCTGTT
TCCTCATCTGTGCGAGAGCAGCTATGTCTACCTGGCAAGGCTGTAGTGAGAGATCATATCAGCATAGGAATGGGGCT
CAGCCCCATGCACAGAGGACAGTTCTTGTTTCATTCTTTTCCTTGCTGTTTCTCTTCCTTTCCTGGCAGAATATGGA
GGAAGGAAGCATCGCTGCCATCTACAGTGGTCACGAAGGCTTCATGGAAGAGGCGAGCCCTGCCTGGGCCTCAATT
TTGGGTGCTGGAGGGAAGCAGGGGCCAAGAGTTATTAATAGTCTTGGCCTGATGGGCCCAGGGAGGCTGAATGTGAT
ACAGACACCCAGCACCACGGTTGGGGAGTACCTGACACCGGAAGGGGAGGGGCCGGGGCTACGGGGAGTGCCACCT
CCCAAAATAGCCAGAGCAGAAGCCTATATAGGTGGCCATCCCACCTCCAGGCTCACTTCCCGACAGGACTTCCCACC
AGCCCAGCCTTTCAGTGCAGGCTCCAGCCCTCCACCCCCACCCGAGGTGAGTGGCAGCTACCGAGGTTGGAGGATAG
AGGGATGCAGCAGGATGAGCCAGCTGGAAGGGAGAGCTACATCTCCCCTGTCCGTAGTGACCCGGGGAGGGGGTGC
GGTGGGGGTGCTGGAGGCAGGGCAGCTGTGGAATGTAGGGCTGAGAGCATGCATTCCTGCTTCTCCACCCAGACTCC
TGGTGTGGCCTGGGGCAAACTCCCCCCACCCACCGCCCCCGTGGCTGGGCCTCAGATTCCCCAGCCTTAGAAC

*Fig. 1E*

Human Gal Promoter: GenBank Reference No. NG_052785.1 Gene ID: 51083

```
CTTGGCCTCCCAAAGTGCTGGGATTACAGGCATGAGCCACCGCACCCGGCCTGAAATTTATTTTTCTTTTTTTCCTT
TCTCTTTCCTCACTTTCCTTCCTTCTCTTTTCTTCTTCTCCTTCTCCTCCTCGTCCTCCTCCTTCTTCTTCTTCTTT
CTTCTTCTTCCCTTCTCTCTCTCTCTCTCTCTCTCCCTCCCTCCCTCCTTCTTTCTTTCTTGACAGAGACTTGCT
CTGTTGCCTATGCTGGAGTGCAGGCTTGATCGTGGCTCACTGTAGCCTCAACCTCCTGGGCTCAGGTGATCCTCCCA
CCTCAGCCTCCTGAGCTGAGTAGCTGGGACTACAGGCACGTGCCATCATGCTTGGCTGATTTTTAAAAAATATTTAT
TTATTTATTTTTAGTAGAGATGAGGCCTTGCTATGTTGCCCCAGCTGGTCTTGGACTCCAGGGCTCAAGTGATCTAT
CTACTCACCTCAGCCTCCCAAAATGCTGGGATTACAAGCGTGAGCCACTGCGCCCAGTCTGAAGTTTCTTTGAAAGC
AAAAAAGGAAACAAAAAGAGTACATAGGCCCAAATGAAGACAGCTGAAAGTTTAATGTACCTCAAATTCCAGCCCAT
GACTAAGGGATGGACTTTGAGTCTCTTTTCGAATCCATCTCAAGGATTTAGGTTTAGAGTTTGTGCTCCTTTAAACA
GACTAAGAGCCTCTGTGACAAAGTAAATAGAGAAAATAAGTGTAGTCAAGCTCTGGCAGGATTTGGAAGGGGGCCTA
ACGTGGAAGAAAGGAGAAGGCTGGAATTGACTAAGATGTGCTATGCACTGGGCTGGATTTGTTCTCAGCAGAAAGCA
AGAAAGAGCTCTGGGATGGTAGCAGGGCTCCCACTACCACCGGGGGCCAAAGGTTGCAGTATTTCTCAGGTAGCCAA
GAGGCACCCATGAGCCCAGCCCCTGCCCACTCCCTGATGTCATCTAGACACAAGGACATGGGGCATGAGAGGACATC
ATTGTCACTTCTCTGCAGAGTCACAGGAACGTGCCCTCTGCTCCTCCGCCTCTCGGCTGTCCTTCTGCCCACGGCTG
GCCCAGACTCTCATGGCGACTCACTGTCTCCCACGCCCCACTCCCGGCAGGAAACCACTTCAGGGTTTACTGTGGG
CTCCGAAATCAGCCTGTGAGTCCTAGTTAGGGTCCCCTGTGCCTGACTCTCCTCTCCCAGGCTGCAAGAAATAGGG
ATGACCAGAAGTCAAACTGTGCCCTTGGGAACACCCCACCCCTCACCACTGTCGTGCCAGGAGTCTGTTCCTAAGAC
CCCTCCCCAAGTCCTGTCTCCTCCTCTTCCTCCCATAAACCACAGCAGACACTCAGCCACCAGGCTGCAGCCCTGCA
CCTTCTCCAGCAGCCGCTGGCCTTCGCCAGAGTTCTTGAAAGCCCAGTTGTCCTTCCCCAGCCACGTGGAGGCAGAC
GGATCTCTCCTGGGGGCAGCCTGTAGCTGTCTGTGCAAAGGTTCCCAAGACTAAAGTGTAGAGGACAGGTAAGATGA
CACTGTCATGATCATCATTCGTCCTGTGCCCTGTGGACATCAACCCACAGATGTGACATCAACCCATCTGATATTGA
GCCCAGTGGGTGGGGAGATCCTAACCCAGCTGCTGCTGTTGAGGACTTGGGTGGTGTCTGGCCAGTGGGAGGGGAGG
TCAGGCGAGTTTTCAGCAGATGACCCCGTGCTCTTCGGAAGCCCGGAGGTGCCACACTGTACAAGTGTGATGCCTGG
GATCCTGTGCTCCCCTGATGCCTGGGAATGGGGTGAAGGAACAGCCTAGGCTTGGGTTCTCTCCTGGGTTGTTTCGG
GACTTGGCCCCAGCTCAGGAAGGGTTTGTGGAGGAGCCAAGGAGGGCCTTGTTCCTGTGGGATGTCTTTGCCTTGGG
CACAAGGACAGCCTCTTGCTGCTGCTCTGCCCACCGCCCACCCCTTGGCGGCCTCTGGGAGTCTGGGCTGCTCTCCC
TCTGGACCTAACCAGTTGCCCAATGGCTGGACCTGCTTAAGCTCCCTCTTACAACTGGACCAGGCAGCCAGGGGAGG
CACTGAGAGGCCGAGCTTCTGAGCTGGTGCCTGTGGATGCTCGACGGTCCCGCAGCTCCCACAATGGGATGGCCAAG
CAGACCCTGAGATCCACAGCCCCCTTTAGTGAAACAGGAGGGAGGTCGCTGGGCACAGGGAGCCGGGAACGCCTGC
CCTCCCCGCCATCGACGGCTCCCGAGGCCTGAACCTTCGCTCCAGCCCCAGCACAAGCCGGCCAGGGCGCAGGGCCA
AGTGTTGCCCGCCATTCCCCGGGTACCCCATGACCTCCCAGCTGGGGCTGGCTCGGACTGAGGAGTCGTCCCTGCCC
GTCACCCTCTGGGGTCTCCAGTGCTGCGGAGCTCAGCTGGCTTTTGCAGCGGTAGGGGCTGGGAGGAGAAGCTGCAG
GGAGACCGCAGGCGTGGGACGTTGTGGGGGGTCAGGCTTGCTCTGGGGCTGGGACCCCGGGGGGAGCAGTGGGGTTG
ACGCCACAGCGATGACTTGGGCCACGGGTCTGGGGGCTCTCCCGCGGGGCGATTGGGCTCTGTCTTTCGGGATTAGG
GTCTCTCCCACAGGGTTTGGGGTTCTCTCTGCAGATTTGGGGGAGTCTCTCCCGCGGGATGAGGGGGGGCTCTCCGC
CGCACCCGCCTATGATGGCCCAGAGGACCCGAGCTCGGGTCACTCCCGTCGCCCTCGGGGCTCGGCGAGGGTGCAGG
AGGCGGGCGCTGAGCCGGTGACGCGACTCCGGGCGGCTCCCGGGTGCGCCGCATATATAGCAGCGGCGGCGGTGGCG
GCGGCCACACCGGGCGGCGGACACGTGGAGGGACCCGGCCCGCGCCTTCTGCCCCTGCTGCCGGCCGCGCCATGCGG
TGAGCGCCCCAGGCCGCCAGAGCCCACCCGACCCGGCCCGACGCCCGGACCTGCCGCCCAGACCCGCCACCGCA
```

*Fig. 1F*

Human NPY Promoter: GenBank Reference No. NG_016148.1 Gene ID: 4852
AGGTATAAGGTGCAAAATACACTGGATAGGATTGGCAGTAATCAGATATTACAGAAGAAAACATTAGTGAACTCACA
GACATAGCAATAGAGACTATCCAAAATAAAATATGAAGGAAAAAATGAGCAAAACAGAAGCAAAAACAGATCACCAA
CAAACTGTGGGCCAATATACACTCACCGTCTGACTCAGCCATTCTGGTTTTAAGTATTTTCCAAGAGAATTAAAGGC
TTTATGTCCATACAAAGACTTGCATATGAATGTCAAGGCAGCTTTATTCGTAAAAGTTTCAAGTGAAAATAACCAAA
AATTCATGAGCAGTAGAATTGATTAAAAATTTTGAAGTATATCATATAATGAAATACTGCCCAGCAATAAAAAAGAA
TAAACTATTGCTACATTTAACAATGTGAGTGGATTCAAAATAATGATGCTAAGTGAAAGAAGTCAGACAAAGAGTA
CCTACCGTGGAACTATATTTATGTGCAATTCTAGAAAACGCAAACAAATCTCTAGTGATAGCAGATCAATGGAGGAG
GGGGTGAGGAAGAGGCAAAAGGAAGGAATTACAAAGGTACATGTGGAAATTTGGGGAAGTGATGTATAATCTTCATT
TTCTTGGTTTCAGTGATGGCTTCCTGAGCATATAACACACATGCATATGTGTAAGAATATATCCAATTGAATATTTT
ACACATTTGTAGCTTTGTATATATTCAGCAGTATCTATTCATTCCTTCTGCTTCTTTACCTTAGGTTTAGTCATGAA
ACCACTGGGTTTCATGTGGTCCAGGTTCTATCTGAATCAAGCTATGAACCTGCTATCAGTAAGACCTCCTAATTGCA
AACCACATGGACCTTTACCGGTTATTTGACTTCTCTCGGTCATTACCTTCTCTAGTCTCCACTGATTCACCTCCTTT
TGAATCTCAACAAGCTCAACAGTATCTCAATGTTATCTTAACAAAGCTGTTAGAAATAAACAACTTGACTTTGAAAC
AAAGGAGAGAAATGGCTCAGCAGCTAGGAGAAGATGCAGGGTTGAGTTGCCAACAGTTGGTTTTGTTTGTATTTTGG
CCAGGGGATGTGGCTTGGACTGGAGAGAAAGGAGATAAGGATGTAAGCACATGTAGGGCATATCACCCCCTATTTTT
TATTCTCTGAATCCTTAACCCTCAGAATAAGTTCTTATTCTTGAGAATCAATGACATTATCTTAAGCTAAATTAATC
AAGCCTCCACAGTGTTCTTCTCAATAGTGGTGTGGGCCTTCCTAGAAGTAATTTTTCCCAAATTCAGTGATACAT
TTTAAGTTCAGATTTTAATTGATATGAATCTGTGATACACTCTAAAATAAGATTATTTTATTGAAAAGTGGACTGTA
ACTTTCCCTTTATCTAGGAAGAGCTCTAAGTTAGAAGATGTTTTGCACTTTTACCGAAGGCTGTGTCTTGTAAGCAC
CCCCGAGCAACTCTGAGAGCCTTGATTTTTGTGTCCTCAGCATATGTTTGTGTAATACAGAAAGAGAAGCAGTTGCC
AAGTGAAAGGGATGTTGGTCTCCAAAATTATAGTTTGATCCCACAAACACACAAACACATACATGCAAAGGATTGTT
TGCTTCACGGTTTTTGATATTTAATTCAATGCTGTTGGAACAGCACAAAAACTAAGTGTCAGTTTAACAGAATCACT
TGTCCTTTTAGCATTAAAATAACATGGAACTTAATGCTTTAATTTCCCAACATGCCTTTTTATTTAGAAAGATTCAG
ACTTATATTTCATTTAGAAATAAAATGCCATTTTATTTAGAAAGATACAGGAGCATTCATTCACGGAACTTTCAGAT
CTCAGTCCACTGCATAAAATCTTGATCCTGTAATAATAGTTTCTGTATCTTGCATATTCATTCAACAGGTTTAACGC
GATGAGCAAATTAATGTTCATCGTTTTAACATGTTTCATCTTAATCAGAACCCACATTCTCAACGTTAATTGAACG
TACATAGGACTATACAAGGGTTAGTAAATAAGACAGAAACTGTTGTTCATTTAACCACCGTCACTTTGGACCAAAAA
AGAAAAAATATATATTTTAAAATTGAGCTTAAAAGAGTCTCTAGAAGCTGGAAGCGTGGCTCTTTTTCAGCAAACT
GGGGGAATAGGTTTACCGTGTTCCCCCTCTGGGGAATTTTGAGTCGCCACACTCATGTCTCGACCGAGCCTGGCTCG
CTGCGTCTGAGCGAGTACTTGAGGAAGGCTGATCTAGAAAAACCAGCTGAGAGAAGGGGCAGAAGCCCCTGAAACCA
CGGGCGGGGTGGGGTGGGGAGCGCAGCTTTGGGACCCTCTAGCCGGAGACTTCCGGCAGCTGCCTCCGACTTGTTC
TAAGTACAGGAAAAATCTGTGCGCCCAGTTGCCTCACTCCAACAGCGCGCAGTTGTGCCCGGCGAGGATGCCGCGCT
AGTCGTGGAGATGCCCCACCACAAAGAGGATTCAGGTGCTTCCTACTCCGGCACCCAGTGGGTTGGTAGTCCTGTTG
GCAGGAGACAAGAATCGTCTGGGCTGCTCCTATCTCTGGCAGGACTAGACGGGGCGTGAAGGAAAGAAGGAAAGAAG
GAAAGCAGGGATCGGGCACTGCCCGAGGGCAGATACTTGGGCTTTGGTGTTGTCCAGCGCGCTCGGAGTGCGCTGCC
TCGCTCACGCGGTCCCAGGCCCCGCTTCTTCAGGCAGTGCCTGGGCGGGAGGGTTGGGGTGTGGGTGGCTCCCTAA
GTCGACACTCGTGCGGCTGCGGTTCCAGCCCCCTCCCCCGCCACTCAGGGGCGGGAAGTGGCGGGTGGGAGTCACC
CAAGCGTGACTGCCCGAGGCCCCTCCTGCCGCGGCGAGGAAGCTCCATAAAAGCCCTGTCGCGACCCGCTCTCTGCA
CCCCATCCGCTGGCTCTCACCCCTCGGAGACGCTCGCCCGACAGCATAGTACTTGCCGCCCAGCCACGCCCGCGCG

*Fig. 1G*

Human SST Promoter: GenBank Reference No. AC072022.19 Gene ID: 6750
CCTGCCTGTGTGCCCTCTTGTAAGGCACTGAAGGTCTCAGGACCTCAGTTTCCTCCTCTGTGAGGTGGGAATAGCAT
GCCCTGAAGTGTTGGATGAGAAAGTGTTTTGTGAGCAACAGAGGACTGGGTAAGGATTCCTAGTGAGTTTGGTTGGT
CTGGGCAATAGCGTCCCCAATACAACCACAAAACACTTTACCCTTCCAGCTTTGAGACTTGGGAGAGATGCCCTGGG
GGTTGATTACAGAAGGCTCAGGTTGGGAAAGTTTGAAGTGCTTCATGCTAAACCAACCTTTAAGCTATAACTGGCCA
TGGAGGGCTTAAGGGAGAATTTATGTCCCTTTTTGTCCTGGCTTCTCTGATAAGTGGTTCTCAGACTCATAACTCTC
CAGGAGTTATAAAACAACAAAAGCAAAACCCTTAAGTCATCTCATTTACAGCTTCAGCTCTTCAGCAGGGTATGAGG
GAAGCAACTGTTTACTATTCATAAGTAGATACTTAAACAGATAGACATCATGAGGTTTTTGTTTGTTTGTTTTTGG
TGAGAAGCAGTTGAGGAGGAAGAAGAAAGAAAAGAGGAGAGAAAAGAGAGGGAGAGATGTCTTGAGGCAGAGACTG
GGATAGGCACTGGCTAAGCAGGGTGAGAAGGCAGGGAAAGAGCCGGGCTGACCCAAACCAAAGTCAGAAAATGATTG
AGAAGAGCAAGAAAAACAAAGGAATGAGGATACAGAGTCAAGAGAGGAGACAAAAGAAGGATTGAGTGAGGAAAATT
CTGAAACATAAATTTGCAGAAAGGTTAAGGAAAAGGAGGAATAAGAAGGAGGAGAAAGTGTAGAGGGAGAGCACAAG
GATGTGGAAGGAGGGGAGCAAGCGTCTGGGGAAGGAGACAGAAGAGATCCTAGAGCACAGGGGAAGATGGGGAGCTG
CTATTTGTTCTTCGGCTGGCTCCTGCTTTGGAAAAATCCTCGTTTCCTACTCAGTGGGTATGCCAAAGACCACATCC
TGGGTACAGGAGATATGAGATCATTTGGAGGTACCTAGAGACAGTCACAGTGATAGAACTAAACTCTGAGTCCTTAG
AGGCCAGAGAGAGTTGCAAGATTTAGAGAATATAACATGTATTTCCTAGGACTGGGTTCCACAGCTCCAGATTCATT
GATCTCTTAGACTACTCCAACACATGTGAATGACTTTTTAATGCCCCACTTTGTGCTTAGTCTTGGCTGGCCTTGTC
AAGACCTGGAAACTTTAACACTTCTTGCTGTGCATTTCCGCTTTGCCTTGGATTACAAGCACAAAAGAAATAGTGA
CAATTATTCAAGCCATTCAGGATACTTCCCAAACCCTTCTGCCTCTCAACACTGTGGTTCGGGTCTAAGTACTGAGA
ATATTTAATACCTAATATGAGCTTCGCATGGTTTCCAGAGATGCAGCATATCTTTTAGCTAATATTGGCTTTTTT
GAAGCTCATAAGATAACAGCTCTTAAAGATCCTGTAGGGATCATCTCGTCCATGCTAGGAAATTAGCTGGTCCTTCC
TCAGTAAGGAACTATTTAGATAAAAGCAGTCAGAACTCTGGCCTGAACAGTAAACATTTAACCAGAGTTCAATCAGA
ATTCAAGGACAGGTTTTCTTAAACTTTCTTTGTTTCTAGGAGATCAGGCAGAGCTGAATTTAACCAAGAATCTTTTG
ATCCTTTCCACATATAGATATACAATAGTGGTCACATATGTTCTGGGAGTTCCTAGACCTTATATGTCTAAACTGGG
GCTTCCTGACATAAAACTATGCTTACCGGCCAGGAATCTGTTAGAAAACTCAGAGCTCAGTAGAAGGAACACTGGCT
TTGGAATGTGGAGGTCTGGTTTTGCTCAAAGTGTGCAGTATGTGAAGGAGAACAATTTACTGACCATTACTCTGCCT
TACTGATTCAAATTCTGAGGTTTATTGAATAATTTCTTAGATTGCCTTCCAGCTCTAAATTTCTCAGCACCAAAATG
AAGTCCATTTCAATCTCTCTCTCTCTTTCCCTCCCGTACATATACACACACTCATACATATATATGGTCACAATA
GAAAGGCAGGTAGATCAGAAGTCTCAGTTGCTGAGAAAGAGGGAGGGAGGGTGAGCCAGAGGTACCTTCTCCCCCAT
TGTAGAGAAAAGTGAAGTTCTTTTAGAGCCCCGTTACATCTTCAAGGCTTTTATGAGATAATGGAGGAAATAAAGA
GGGCTCAGTCCTTCTACTGTCCATATTTCATTCTCAAATCTGTTATTAGAGGAATGATTCTGATCTCCACCTACCAT
ACACATGCCCTGTTGCTTGTTGGGCCTTCCTAAAATGTTAGAGTATGATGACAGATGGAGTTGTCTGGGTACATTTG
TGTGCATTTAAGGGTGATAGTGTATTTGCTCTTTAAGAGCTGAGTGTTTGAGCCTCTGTTTGTGTGTAATTGAGTGT
GCATGTGTGGGAGTGAAATTGTGGAATGTGTATGCTCATAGCACTGAGTGAAAATAAAAGATTGTATAAATCGTGGG
GCATGTGGAATTGTGTGTGCCTGTGCGTGTGCAGTATTTTTTTTTTTAAGTAAGCCACTTTAGATCTTGTCACCT
CCCCTGTCTTCTGTGATTGATTTTGCGAGGCTAATGGTGCGTAAAAGGGCTGGTGAGATCTGGGGCGCCTCCTAGC
CTGACGTCAGAGAGAGAGTTTAAAACAGAGGGAGACGGTTGAGAGCACACAAGCCGCTTTAGGAGCGAGGTTCGGAG
CCATCGCTGCTGCCTGCTGATCCGCGCCTAGAGTTTGACCAGCCACTCTCCAGCTCGGCTTTCGCGGCGCCGAGATG
CTGTCCTGCCGCCTCCAGTGCGCGCTGGCTGCGCTGTCCATCGTCCTGGCCCTGGGCTGTGTCACCGGCGCTCCCTC
GGACCCCAGACTCCGTCAGTTTCTGCAGAAGTCCCTGGCTGCTGCCGCGGGGAAGCAGGTAAGGAGACTCCCTC

*Fig. 1H*

Human GRPR Promoter: GenBank Reference No. NG_012512.1 Gene ID: 2925

```
GCCTGAAGCCAAATTCAGCCTTTCCCTCCAGAAGCTTCCCTTTTGACCTTGCTCATAGCCAGTGGGAAGAGGCTTTG
TCTCCACACTCTGTGGTCCCATTGAATCTACCTGTTCTCCTAAATTCTATCAAGTCACTGTTGCCCACCTCATGTTA
GAGCCCCACAGAAAATCCAGTCTTTTGGAAAGATGAAAAAGGTGACTCTATTGACTGAAATAGAAACAGAAGTGACA
ACCCTGTCCCAACACATAAGAAAAGATGCTGAGTCATACTCCAATTCTATTCAGAAATTGGACTCCCTGGGGACAGA
GATTTTATATTACATTTGTTCCATGTCATGTTCACATGTCAGAGGCATCTCATGTTCACCAGTAAATAAAAAGCTAA
GCAAATGTCTGAATACGTTTGGTGTTTGGTGTTCCGGCTCTGCCGGAAGGTGACACATAATGGTAGGGATGGAAAGA
GTCATTATAGTTAATTAGTTGAAATGACATAGAAATTATGGAATTAGCTTTTTTTTTTTTTTTTTTTGAGAG
GGAGTCTTGCTCTGTCGCACAGGCTGGAGTGCAGTGGCACGATCTCGGCTCACTGCAAGCTCTGCCTCCTGGGTTCA
CGCCATTCTCCTGCCTCAGCCTCCCAAGTAGCTGGGACTACAGGTGCCCATCACCACGCTTGGTTAATTTTTTGTAT
TTTTAGTACAGACGGGGTTTCACTGTGTTAGCCAGGATGGTCTCGATCTCCTGACCTCATGATCCACCCGCCTCGGC
CTCCCAAAGTGCTGGGATTACATGCGTGAGCCACCGCACCTGGCCCGAATTAGCTTTTAAAGCATCCTTGATCCCC
GAAAATATTAGATGTCAAACCTCAACGCACCTTTACTCCTAAAATACCATTAGAAGAATCTATAGTGCTGTGGAACA
CATAATGCTAACACCAGCTATGAGAAATCAATATCTATCAGCATCCCCTTAACTTACATTGGAAGAAACACTAACCA
CCCAATTAGATTTAAGTAGTGAGGCTGACTCAGCACACAGGGGTGTCTAAAGAAATAAAGGGAAACAACATCCAGAA
GTTCTCTTTGTGAACCAAAAATATGCCTTTTAGACCAAACTTCTTAGCAAGAATACAAGATCCATCACAATCTCACC
CAAACCTGCTTCTAGCTGCATTTCACGCTGTTCTTTTCCACCCCTGTCTTCCAATCTGGGTGACCCTCTGGATTTA
TAGATGTCCCTCTGCTCAATGTCATGCTCTTTCCTTTATGCCTTGATCCTAGGCACATATGATTTCTTCATTCAAA
AGACCTTGTCAACACTTAACCTTTAAAGATATCGTCTTTTCTGGAGAAAAGGTAGTTGCTTCACTCCAGAGAGGGGT
TGGGGTCTAAAGAGCTGTGAGAGTACACATCTTCATGCTATTTTCTCAGCCTCTTGCTCAGTGCCTGGCAACTGGT
AGATGTTTGATAAATTTTTTTCAAGTAAATAAAGGAGTTGCTAATTCACTCGTATGAGTGCTTGCCTATTGATCTGA
GGTCAATCACTCTTCTGAACTCATTGGGCTTTTCCAAAGTAAGCCTTTCCCCCTCAATCTAATAATGATAATAATAA
TAAGTGCTAATATTAATTGAGCACTTACTATGTGCCAAATACTATGCAATCTTAACATGAATCATTTCATCTAACTT
CATAAGTTCTCCTCACCCTGCAGATGAGGAACCTGAAGCTTAAGCACTAAGTAACTTGCCATAATTATAAATGAGG
GAGCCAGGATTGAAGCAGAGCCTGTGTACTGTATCATTAAGCTATATTGCTGGCAACTAATCAACACCACTGGGCTC
ATGGCTATTGGCTGGTTACTGGTGCTACTGATCTCTGCCGAGAAGCTCTTCCACCTCTAGCCATGCAGCATCAGTCT
CCCTCCTGCTGGCAGAGAGGGGCGCTGAGCCTTTCATATTTACATAGAAAGCATGGCAGCAGCCTCAGTGTTGGAAC
CTGCCACTGGAAATGTCCATAACAACACAGTTGGGGGCTTTCTTTGTGGGCCCTGGCATGGTAAGTGCAAGTTTTGT
TATTCCTTATGGGTTCTGAAAAATGAGACTTCACCTGTTAGTGACTGGCTTCACGTCATGTACCTGGAGGAGCTGGC
TTCACATACGTCATAAAGATGCACTCTAATAATGTATTTAGAAGTTGTTGGCTAAAGGTCTAAGCCTGATTCTAATA
GCACTTCCTCAATTAAGCTTTTTCTAGCACTCCTTCAACGATAACTTACTTCTTTTACCACCCACTCAATTCCTCAG
TATTGTATCTATCACGCTTTTATAGTTCTTTATTTTCCACACAGGGCTATAAAGAGGATATTTGCTATAAAACATGG
CAAACATTCAATTAAAAATGCAAATAGCTGCATCAAAATGCCGATTCATAAAATTTTAGATCAGATGAGAAAAGAC
CCATTTTCTGGAAAAGACTATTGATCATTGAGAGTTAAGAATACAGCTGGTTCCCAATTTAATTTCTCCCTGGTAA
ACAGAATAGGAATGGCTTGGCAAATCTACAGGAAAGAACATGTGTGCATTGTGCTTCTGGCTTTTCCAGATGTCAGT
TGCTGAAGGTTTAAGGTGTGAGTCTGTGCATGTGTTTCTGAGGATCAGTCCCTGTTCAAAGAGGCAGTGGGAAGACT
GAGTGGGATAACTCACACATGGACACCCTGTGCATCAGTGTGCGTTTAATTCAAAGACAGACCTCATTTGATAGCAA
TATTGACATGTCATTCTAATGAATTAGAAAAAATGAGAAAATGGGATGTAAATCCCCATCTGGATTCATGGGGATAG
TATCAGAAAGATTTTCAGTGCCTTTGCAGAATGCTAGCAACATTTATTAAATACCTACCCTAGGTGCTATGTGCTTA
CATGAGAAGCCAAAGGTATCTGTTAAGCTAGGTAGGAACTGCAGTCGGCTGGTTGCTTCTCATCTGGAGAAAGCCTA
CACATGCTGCTGCCAGCGGCCAGCTGATCTCTAGGTGTTTAGGCCTAGAAGACCAACCAGCTCCAAATCACTTAAAG
CCTAAACGTTCCCTGTCTCTACTAAAATACAAACATTAGCCACGCATGGTGGCGGGCGCCTGTAATCCCAGCTACT
TGGGAGGCTGAGGGAGGAGAATCGCTTGAACCTGGGAGGTGGAGGTTGCAGTGAGCAGAGATTGCCCCATTGCACTC
TAGTCTGGGCGACAGAGTGAGACACACAGACACACACACACACACACACACACACACACACACACACACACACAC
ACACACACGCCTAAACATTCAAGGCCAGGATGCTTGACAGATGTTGATTCATAAAAATGACAAAAAGCACAAAATCC
AAAATCTCGTATAAGCTCAGTGGCTGTGGCAGCGAGGTTGAAGAGCAAAGGCAGGCCGGGCACCTGGCTGATGATGT
GTGGACCCGTTGCACAGCAGGGCCCCGCAGTGCGGTGTGGGTGTGGGTGGGCCAGTCTCTGCCGCTCACCCTATTCC
AGGGACACAGTCTGCTTGGCTCTTCTGGACTGAGCCATCCTCATCACCGAGATCCTCCCTGAATTCAGCCCACGACA
GCCACCCCGGCCGTTTTCCTTGTTCTGTGTGGGGAGGGAGGCAGCGCGGTGGTTATCAACCTCACCCTGCAGAGGAG
GCACCTGAGGGCCCAGAGACGAGGAGGGATGGGTCTAACCCAGAACCACAGATGGCTCTGAGCCGGGGCCTGTCCAC
CCTCCCAGGCCGACGTCAGTGGCCGCAGGACTGCCTGGGCCCTGCTAGGCCTGCTCACCTCTGAGGCCTCTGGGGTG
AGAGGTTCAGTCCTGGAAACACTTCAGTTCTAGGGGGCTGGGGCAGCAGCAAGTTGGAGTTTTGGGTACCCTGCTT
TCACAGGGCCCTTGGCAAGGAGGGCAGGTGGGTCTAAGGACAAGCAGTCCTTACTTTGGGAGTCAACCCCGGCGTG
GTGGCTGCTGCAGGTTGCACACTGGGCCACAGAGGATCCAGCAAGG
```

*Fig. 1I*

Human PRKCG Promoter GenBank Reference No. NG_009114.1 Gene ID: 5582
CCCGCCCAGCCTCGCGGGGCACGCCGGGAGGCGGAGTTCTCGGTCGTGTCCCGAGAGTGGCTGGTCCGCAGGCTCGG
ACTACCAGTCCCAGAATGCACTGCGCCCGCAGCCCGGGGCGGGCCGTGGTTGCCCCTGGCAACAGAGAGGGCTCCCG
GGAGCGGGGACTGGGAAGCGCTCCCGAGCCGGGGAGGCGCAGAGCCCGACCAGAGAGAGGCGGGGACGCGGGTAGAG
CGACCAAGAGGTGTGGAGGCCGGAAGAGACTGACCGCGCCGGCCCTTGGAGAGACCCCTTTCCTGAGAGGGGCGCA
CAGAGAGGATGCCGAAGCCAGCGAGATCTAGAGAGAGGGAGACAGGGATTGAATCACAGAGACACTTAGAGGGAGGG
AGAGACCTCAAAGACAGAGAGATTCACAGGGCCAGAGAGACACGTAGAGTGGGTCAGAGAAGAGGACAGAGGACAGA
GACATAGAAAAGACAGGAGGGAGAGAGACTGAATCACAGAGACACAGGGAGAGAGGGAGAGACCTCAGAGATGGAGA
GAGACTCACAGGGCCAGATAGACACATGGAGTGGGTCAGAGAAGGGGACAGAGAGAGAGACACAGAAAAGGGAAGAG
GGAGAGAGACTGAATCACAGAGACACAGAGAGGGAAGTCTCTATCTAGAGACCCTCGACAGAGATTCCTAGAGCCAG
AGACAGAGATTCAGAGAGCCAGAGACACAGAGAGATTCATAGAGACATATAGAGAGATTCAGAGAGCCTGAATCACA
GAGATTCACAGAGCCAACGAGACAAACAGAGAGATTCATAGAGCCAGAGACACAGATTCGGAGAGTCAGAGAGACAT
AGAAAGATTCATAGAGCCAGAGACACAGAGATTCAGAGAGTCAGAGAGACATAGAGAGACATTCATAGAGCCAGAGA
CACAGAGAGATTCATAGACATATAGAGAGATTCAGAGAGCCTGAATCACAGAGATTCACAGAGCCAAAGAGACAAAC
AGAGAGATTCATAGAGCCAGAGACACAGAGGGATTCGGAGAGTCAGAGAGACATAGAAAGAGATTCATAGAGCCAGA
GACACAGAGATTCATAGAGACATAGAGATTCATAGAGCCAGAGACACAGAGATTCAGAGAGTCAGAGAGACATAGAA
AGACATTCATAGAGCCAGAGACACAGAGAGATTCAGAGTCAGAGAAACATAGAGATTCATAGAGCCAGAGACACAGA
GAGATTCAGAGTCAGAGAGACATAGAGAGACATTCATAGAGCCGGAGACACAGAGAGATTCAGAGTCAGAGAGACAT
AGATTTATAGAGCCAGAGACACAGATTCAGGGAGTCAGAGAGACATAGAGAGACATTCATAGAGCCGGAGACACAGA
TTCAGAGTCAGAGAGACATAGACATTCATAGAGCCAGAGACACAGATTCAGAGTCAGAGAGATGAATAGATTCAG
AGAGCCAGAGACACAGGGAGAGTGAATCACAGACACAGAGGGACGGGGAGATCCCCAGAAACAGAAAGAGATTCATA
GAGCCAGAGAGACAAATAGAGATTGGGTCAGAGAGAAAGGGACAGAGACAGAGACAGAGAAGAGAAGAGGGAGAGAG
ATTGGGTCAGAGAGAAAGGGACAGAGACAGAGAAGAGAAGAGGGAGAGAGAGACTGAGTCATAGACAGGAGAGAGAC
CCCCCTAGCATCAGAGAGAGAGAGAGAGATCAACAGAGCCAGAGAGGGACAAGTACAGAGAAACAGATGGAACCAGA
GAGATATAGGAAGAGACAAACAAAAACAGAGACGGAGTTGCAGAACCGGAGGAAGGGAGAGAGACAGAGACAAAGGC
ATTTATAAAGACGGGTGGAGGTGAGGAGAGAGAGGGAGAGACAGGGGCAAGCATTTAGAGAGTGACTCCCAGAGAGG
AAGACAGAGACGGACTCCCAAAGAGATCAAGTTGCAGAGGGAGGGGGAGACAGAGTCACAGCCTGAGAGAGAATAGA
GATTCACAGAGCCAGAGAGACAAAGACAGGGAAAGAAACAAACTCAGGGAGACAGAGGCGGAAGAATTTATCAGACG
TAGAGGGAGAGACAGAGGGAGACTGATTCACAGTGAGGCAGACCAAGACCCCGAGAAGAACCACGACACCAAGACCC
AGAGATGGCGACAGATACAGATGGAGACACACAGCAGAGGAAATAGAGAAATAGAAAGAAATAGAAACAGCATTTCT
CGGAGACAGGGAAAAGAAAACAGATCCACTGAGAGGCAGAAACAGAGACACATCGAGAAAGCTCGCTCCAGGAATAG
AGGGAGAGGGACAGAGGTCACAAGAAAGACACACGCAGGCAGAGAGCTACACAAATAATGGAGAGGCAGGGGAGGA
AATAAAGACTCAGCCGGCATCGGAGAAAGTGAGAACCTTAGCGCCCTGCCTGTCCACTGCTGGACCCCTAGCGTGGA
GCATAAAGTTTGTTGAAGGAAGGAGAGGGGCAGGGTCAGACACAGGGACCCCAGGGCGCCCACAGGACACACGAGGC
ACCCTAGTGGGGGAGGAACGCGGGGCAGGATGACAGATTGCAGGGTGGTGGGGGGGAGCCAGGCTCAGAGGATGCCC
CTCCCTCCAGCCAGCCCCCGGAGTGGGTGTGTGCACGTGTGGGGGCGGGGAGGGAGGACATTTGTCCCGTGTCTCC
GGGAGGGGAGCGCCTTTAAGCCGAAACCCCGCCCTCTCGGTCGTCCTGGCAACGCCTCCCCCAACCCGGGGCTCCCA
CATTTCAGCAGGTGCCGGAGCTGGAGCTCCCACCGCCGCCGCCCGTGCCTCCGGCTGCCGGCGCCCCTGCCTTTGGC
TCTTCCTCCCCACTCGCCCGCTCCCCCTGGCGGAGCCGGCGCGCCCGGGGTGCCGCTCCCTGCCTGGCGCGCTCCGC
ACCTGGAGGTGCCTTGCCCCTCTCCTGCCCACCTCGGAATTTCCCTGTGGCTCCTTTGATCCTTCGAGTCTCC

*Fig. 1J*

Human Calb2 Promoter GenBank Reference No. AC106736.4 Gene ID: 794
CGCTCATGAGATCACTGTCGAGATACTTCCCTTCATTTCCTTCTCTGTGACCTTGAAGGGTCTGGGCTACATCATCT
CCATGTCTCCATCCCATTCCGATATTCTTGAAGATCAAGACCCTGGGTGGCCCATTAAAGGGGAATGGAAGGGAGGT
GGGTAGATTTTGATACGTCTTTGCAAAGAGGTTGACATTCCTGTTGTTGCAGGCTTGGCGGAAGTACGACACAGACA
GGAGTGGCTACATCGAAGCCAATGAGCTCAAGGTAGGATGGGCCTTGGGGAGGGTGTGAGGCCAGAGTGGCGGTGGG
CTTAAGGTGCCTGAGGAGGGAGGAGATGTTGGATGAGGGGCATGAGTTTGCGGGCTGCTTAGGAATACTCAGACCTG
GCACTGAATTGTTGGACTTGTTTAGAGAAGTCAGGGGAAATCAGTAACATAGAGCTGCCAGGCTGTAGATTTCAACG
AAACCCAGCTCTTCTGCACCTCCATGCTCGGGACAGGAGTCCTCCAGGCAATTCCAGAAGATTGGCCTCTGGCTCCT
AGGTCCACCTCCAAATTCCTCTGGCTATCACCCAGTGATTCCCCAGGCACTGCTTAGCTCCGTATACTGGTCTCCCA
GGAGGCAGAGCCAATCTCTAGCGCCTATTCTGTGAGGCAGGGTTGCACCACCAGCTAGTACAGCCTTAAAAGTCACT
CCCCAAGAGTTAGGAATTATGAGGGCCCTGAGTCATAGAACTGGTAGACCTGAAAAACACACACACACACATTGAGA
GACTGTCTGAATGAGCAAGTAAGGAAATGAATGAGGGACCGAATGCACGAGTCAGGAGTACTAAAGAGGCCTTTTGT
GTTGCAGGGATTCCTGTCAGACCTGCTGAAGAAGGCGAACCGGCCGTACGATGAGCCCAAGCTCCAGGAATACACCC
AAACCATAGTGAGTGAACAGAAGTGTCCCTCTCCCCAGGGTGCAGGACTTGTGCCCCAAGCCACTTGGGCTCTGGT
GTGCAGGGTCCCTTGTTTGCTGATTCTTCAGGCCCAAGGGAAGTGATTCACAGTGGCAGCTGGCAAAAAGGGATGCT
ACTTCGTGGCTTCACATACCCTTTGAGGTCCTGGGTGTGAGCTGACTCGTGGGCCAATGTGATTGTCTGTCTCCATG
GCAACCTCTGCAGCTCTAGGAGAGGATGATCTTGGAGAGAGTGGGCCTTTAGTGCCGGCCTGCTGTGCCTCAGCTGC
CCCTGTCCCTGAGGAGGGGAGAGAGGAGCAGTGAACGAGTCCCTGTGGTCCACCCAGGGGACCCCCGTGACTGATTT
AGCCCATGTTGGTTCTTGGCCCCTACGGACCTCAGAGGAAGCATGAGCACGTGTCACCCGTCCTCCTTCCCATCCTC
TCCAGTAAAAGGGGATGTCAGGTCAGAGAAATTCACAGCAAATAACCCAGGCACCTTTCTGTCCCCAACAGCTACGG
ATGTTTGACTTGAACGGGGATGGCAAATTGGGCCTCTCAGAGATGTCCCGGTAAGCACCTCACCCCCGGGGTCACTG
ATACTGGCTCCCACAGGTCATTCCTGTGTTATCCGTCTCTGAGATCCATTGGTGGGAAAGTGACAGGTGCGGGTGTC
AAGAAGCTCAAGACAAAGCAAGATAGAATTGTGACCGTCAACACCTCACCTTGTCTGTCTCCCTCGTTTTTGAACTT
CCCACTGATTCATTATGTGTGAAGTGCTCAGAAATCATTTCTGTAACTGCAGGCACCGCCTCTGCCTTCCCCTCTCC
CGCTTGCCCTTGCCTGTGCAGTCTCCTCATCTCTGCTCTAACATTTTCTCCCCAGACTCCTGCCTGTCCAGGAAAAC
TTCCTGCTTAAATTTCAGGTAAAACTTTGCTTTCCTTCCTTCCCCCTTCCCTCATCCCTCTGAGCCTGGCCCTGCAC
CCTCCTTCCCCAACGCACCACACACAACACACTACACACACCCACACACACCACACACACACAAAACACACCACAC
ACACAACACACACAGATCACACACACAAAACACACACAGACCACACACACCACATACACAACACACGCAGACCACAC
ACACTACATATCACACGCACACACCCCACATACACAGAGACATCACACACACCACACAGACCACACACCACACACAC
AACACACACATCACACATGCACACACCACACACATAAACACACACACAAACGCACACCCACACACACACCACTGC
GCTTCTGCTTCTGTCTTTAATACCCTGGTTCTTGCAGGGCATGAAGCTGACCTCAGAGGAGTTTAACGCGATCTTCA
CATTTTACGACAAGGTAAGAGAGGGAGTTGGCATGGCAGGGAAAATCAGAAGCCCATCAGCCCGTCCAGAAGGGCTC
AGCTTCATCCCTGGGAAGAGACAGCTTTCCAGGGGTGGCCTGGGCCGTGTGGTTTCTTCCTGCCGCATCTTCTGCTG
TATGAGAAGGCAAATGTCATTCTCCACCGGTGGCCTATGGAGCCCAAGGGGTTGGTTTCTGCAGAGTGCAGCCGAGA
ATCGTTGGGGGAGGACTATGCTTAGAACTAGGGTGTGACCACGCTGTCGGGAGCCAAAGGGAAGAGACACTCAGAAC
TGCCCTGGTGCCAGATCACAATTCTGCCCAGGGCCAAGTCTTTCTCTGGGAAGTTGGAAGTTAGATGATCTCCATAC
CCACCCCTCCCTGGGCTGTCCCCTGCCCACATGACTCCGGTGGTTTTCTTCATAACCAGTGTTGGAGGTAAACTTTA
AATAGCCCCCGGACTCAGGGAGTTAACCAAATGCTTCTTGAATCTCACTTAAATTTTCAACGCACATGAAAAGCACC
ACAATGAAAGGCTACCCAAAGCTTGCACCCACTGCCACCTTCCTGCCATGACTGGTTAAGGCAGAAGGGACACATTA
TTTTGTCATTACACGATCTGAACACCCCCTTTTGCACAGAGTAATGGAGAGGCTAGACTCTTAGACATCCCTGG

*Fig. 1K*

Mouse CCK Promoter (2441 bp) (GenBank Reference No. AC131660.4 Gene ID: 12424
GAATTCCCAGGGAAGATCCCAGGGAAGATGAAGAAACCATGGCTACAATATTTTATTAAATAAAGAGTCCATTGTGC
CACCTTCTTCCAGCTTCTAACTGTCCTTGACACCTTTGGCTTCTCCTGGTGGCTTTTCTACTCTGGCCTTTGACCCT
GCCTGTGGTCAGGTGCTGGACCCTTCTCCCGTTCCTTCCTCTGGCTGTCACACCTGGGAATCTGGGCAGAGATGCCT
TTTCTCTTCCCTCGCTTCCCACCTTTTGAGTCTCTTCCTACAGCTTCCAGGTGGGAAGCCACCATCTACAGAAAGAG
TCTTGGGTTGTACCTCCAGTGTCCCTCTGTCCAGGACTTGAGATCACAACCTTCTCTAGCTGTCCACCCATAACCTG
GATTCATCCCCCACGCCCCGCCAGACACACACCAGTTGGTGTGTTTTCTTCTGAACTCCCCCTGTGGCCAATACACT
CCCACCCACCCTTGTCTCTCAGCCCAGAACTTCACAGTCAGCCCCAGACACGGAGTACCTTTGGGTTCTTGAAGAG
CAAGATGCTGCTTCCATGCCTGGAAGTTTCTGCTTATGTCTACTGTTCTAGCTATTCGGATGTTCTATTGTAGGCAC
TTAGGACTCGTATAGTGTCTGCTACATTTCATGATAGTGAATAAATTTCACAAAAGCATATTAGGCTTCCTATAAAT
CTGTCCTCATTCCTCAATGGCCCTCCCATCTCCTGTCTTCCTAACCTGTCCTGGTCTCCCGTGTCTGCCCTAGGGAC
ACCTCCATGTCACCACCAGACTCAGTGGAAATCCTTACTCCGCCCTTGGCTATTAGTGCAGATCTGAACTCAGTTCC
TTGTACTTGCAGGCAAGCACTTCACTGGCTGAGCCGCCTCCCAGTTCCAGCTCCAGGCCCCGGCTCCCAAAGGTGT
TTATTTGTGTGGGTATTTATTTTGTCCAGTCTTGGTCACACCGCATCCTCAGGGGCTGGGCACAGTTCATAAATCTT
GAGGCAAGCGATGGAGGGAAGGAGGCAGCTAAGCGTCCATATCTCAGCCACCGACCCAGGGAAGTCAGCGCCTGTGG
ATTCTGACCATATCGAACAGCCTTGTGCCCAGCTGCTTTATCCACAATTCCGGACATGCTCGATCTGTCACAGATAC
ATTCCCACAACCTGAGCTGTCTTGTGCGGGAAATCACCCCACAGCATTTAATCTGTTGCTGTTTAAAACATGTTGCC
TCTAGGTTGCAGACACCGCTAGAGCCACAACCATGAACCTAAACTCTTGGCATCACTTGCTGTTTCTCATAGTCCCC
CTCAGCCGGAAGTCCCCAAACTGTGTGCCTTTTCTATTTAGAAAGAGTTTCTAACCCTTTCTCCATTCACCCTAGCT
TGACAGGGTTGAGGGCATGGTTGCCCTGGCTGGTGGTGACCCCAAGTTACAAGCTAGCAGCAAGGAGGTTGCTGTGG
GGCTTCCTCAGTATGTGTTCTGTGGAATGGGGTTAGAGGGATTCAGCAAATTCTAGCACCCTGGGCATAGATAATCA
CTTTGTTATGTGAGAACTGGGGGTTGCAGGATTGTGCGCACTACAGCAGAGAGAGCCCCCTCTCTCCTTCTTGCTTG
GTAAGAGTCTTTTCTCAGCCAAGATCCTCATCACCCAGCGAAATCCCATAACTTTAGAGGGACTAGACTGGAAAGG
GTGATCTGAGCTCTTGGGAAGGTGCGAGCCCAGCCCGCATGGCTCAGCCAGCCAGAGCTTGGGAGTGCCTGAGACAC
TCTCTGGCGCCACTTCACGACCAAAAGCATCAGTAGATGATAGGCCCCTGGGAAGTCGTCGTGGAAAGAAATTACAA
ATCTTTTTCCCAGAGGCTTTTCGCAGAAAGGCAGGAGCTGCACCCGATCTTACAATTGTGTAAGAATAGAATCCAGG
ATGCCAACTGCAATTGAGTTCTGAAAAATTGGGAGCCCGATTTCCCTCTCTTACTTGTGAGAGCCCACTCAGGTCTG
AGGTGGTCCCAGAGAACACACCAGGATTACATCTGCTGACACCCAGCCTGTGAGGGTCCCCCAGTTTCCTTGAAGGA
TTTGATCCCCAAAGCTCACTGAACTTGGTCAGCTTCTCCATTGCAGATAAACTCCTGTTTTTCACCGAGAGTGGAGG
TGGCACCCTCCCTGAGGTGGACTCTGCACAGGCGCCGAACAGGTGGGAAGGAAGCTCTTTAGATAAAGAGTAAGACC
CATGCAAAGTGCCCCCCTGGGAGGGGCTATCCTCATTCACTGGGACGCTTCCCTTCTCTCCGGAGGGCCACATCAAT
CGGTGGTCCCTCCAGTGGCTGCCTCTGAGCACGTGTCCTGCTGGACTGCGTCAGCACTGGGTAAACAGATGACTGGC
TGCGAACCGGGAGGAGCTATTTAAGAGCAGTCACCCTCCCGCCTGCCCTCACCT

Mouse Calb2 Promoter Region: Genbank Accession No. U34818.1 Gene ID: 12308
CCATGGCGATGGAAAGCTGACCAGTGCTCCCTCTGATCAAGGAATCCTTTCCAAGCTCACCAGAGAGCACAAGCATA
AAGGACAGGAACACAGACTCATGTAATCCCCAGAACAATCCAAGATGTCAATACCCACACACCCATTTTACAGACTC
GGAAAGCCAAGGCACAGACAGGCTGTGTAAGCCAAACAACGTTGTGGAGGTTTTGTTGTTGTTTGTTTAGGAACTAG
ACCCGAGGAGTTTGATTCTATTGCAACTGTTCTTTAGGACTGAGCCTTCTTGCCTTCTCGAAGGCAAGACTCAGGCT
GGGGGACTCTAGCTTAGTAATTTCTCAGCCCTGGCAGCAAGGAATGCTGGGTTACAGAAGCCCCAACAGTTAGCCTA
TTTTGCTGCGTCTTTCCCAGTCTGTTCTTGTAAACAACCTCAAACTGTGTGCCTGGGCAACACACCAGCAGTTTTGA
AACTTGGGCTCCATGTTGCCCTTTGAGGTTAGCTCCGAGCTACCTCAACCTGACCCCAGGAAACAGCCTGCTCTTCT
CCGCTCCCCCCCTCCCCCCCACCCCACCCCGGGTTCTCCTCTCCCTAGCGACCTGCTTTAGATTCTCACCTCCTT
CTCTTTTGCTCTCCCTTCGAAGGCAGCTCAGCTAACACTCATTAGCACATGTTAATGAGCAGCAATTCAAGTCTCTG
TCCTTCTTTTTAGGGGCAGGGTGCTTGCTGTTGCTCTGAAGGTAAGGTGTCCAAGAAGCAAGCACACACTGCAGACC
TTTAGAGTAGGGAGGATATGGGACGGAGGCTGGCTCTCTGATTGAGGAGACCCCACGGTGTGCTGTGCTTGCTGTCT
GTTTTCTTTAACAGAAGTTCAGCACATCTTTGGGTCAGAGTTTACCGCCATCTACCTACGGGACTACGGGAGGCTCC
AGTCTGCTACTACCTGGATAAAGGTCTAAAAGTCTGCAGGATGTGACAGATACCGGAGGGAAGTGGGTTACTGAACA
GTGGAGTAGTTCCTCCATTCCCATCTGAATCCTCATTGCACCTTGTCGATTCCAGTTGTCCACCTACGGTAAAACCT
TGAGAACCCTGCTTTCCTGCAATCCTGGTACCCCTCGAGGGAGTCACAGGACAGGAAGAGTTCTGGGCTCAAATCTT
AGCTTTGCTACTTGTTAATAATGCTATTGCTGCGACTAGAAACTGGGTGTGCTCAAGATGGACAGAGGGAAGGGAAG
GCAGGAGCTGCCTCTCCCCATTTCCAGCTAAATACCTGCGGTGTCCCCGGAGGGCACCCAGAAGTCTCATTGAACAC
TCTCTCCCGGTCCCCAGGAACCCTGGCAGAGAAGAGCCCCCGCCCGTGCAGCGCCGCGCCCTGCGCGATTCCCTGAG
TGTGCGCGCCCCCTTCCGGCGGCCCGACGCGGCGCAGCTCCGGGCTGCATATAAAGGCAGCGTGGCGCGCAGCCCCA
GCGCGAGAACCAGAGCCAAGCGGCACCGAGTGACAGCGCGCTGAGAGAGAGGCTTAAGATCTCCGGAGCGGCTCGCC
ATGG

*Fig. 1L*

Mouse PRKCG Promoter Region: Genbank Accession No. AC245272.2, Gene ID: 18752
GGACTAGATCCTGGATCCCTGGGTATGAGGAAGGAGGGGAGTTGTGCCTAGATTCCTAGATCCTGAGAGACAAGGGA
CCTGGAGGAGTTCCAAAGGATAGAATCAGAGGCATCCATGTGTGTAAGAAGTTGTATCCAGAAGCTGGCTCCTGTGT
ACTTCGGGAGCTGTTCTGGGACAGTGTGAGCTTCCAGAGGTTAAAGCAAGCCCTTCTGTCTTTCCGTGGGCTTGACC
TTAGCACGACTTTTCTTCGGGGGAAAGTTATGAATAATTCTGTGTTCATCACAGAACACAGGATGATGGGCTGCCGC
GCGGTGGTGGCTACACCTTTAATTACAGCACTCCAAAGACAGAGGCAGGCAGATCTCTTTGAGTTCGAGGCCAGCCA
GCCTGATCTGCATAGTGAGTTCCAGTACAGCCACAACAGAACAAACAAACAAACAAAGATGCAAGGTCAAAGAGACC
AAAGTTAACCCAAGTGCACTGGGTGAGCCAGTGAGTGGACTGGAAATACTTGCAGGGGCATAGAGAAGCCCACCCCA
ACATGGAAGACTCATGGAAGACGCATTTCTGGGGTACACTGCTCAACTTGTAGTCAGCTGGGCAGAAGAGTCTTCCT
GTCCTCTCTTAATTGTTTGCTGCTCATATATTACTTCAGCTTTGGGAGGGGCCTCATAGCACAGCCCTGTAACTTTC
TGAGCCTTGGGGGTTCTATGGTTTGTCTTTCTAACATGTAATTATTGTGTGTGTGCATGTATGTGTACACCCCATAG
CCAGTGTATGGAGGTCAGAGGACAATTTGCAGAATTCCACATGGTCTATCCACCATGTGGGTCTTGGGGACAGAACT
CAGCTTATCATGCTCTGTTGTAAGTCTCTTTCTTTCTTTCTTTCTTTCTTTCTTTCTTTCAATTTATTTATTT
ATTTTCCATATATGAGTACATTGTAGCTATACAGATGGTTGTGAGCCATCATGTGGTTGCTGGGAATTGAACTCAGG
ACCTCTGCTTGCTCCAGCCCTGCTTGCTCCAGCCCAAAGATTTATTTATTATTATATGTACGCTGTACATATAATAA
TAAATACATACATAAGTAATATTATTATTATAATAATAAATAAGTACACTGTAGCTGTTTTCGGACCCACCAGAAGA
GGGTGTCAGATCTCATTACGGATGGTTGTGAGCCACCATGTGGTTGCTGGGATTTGAACTCAGGACCTTCAGAAGAG
CAATCAGTGCTCTTACCTGCTGAGTCATCTCAACAGCCCATGTTGTAAGTATCTTTACCCACTGAGCCATTTAGTTG
GCCCTTAGTCTCTATAGCTTTTGAGTTATTTGAGTCCCTCCCCTCCCTCTATCAGCTGATGTTCAATTCAGAAGAAA
TAACTACAGAACTGACAATAGTAATAAGAAAATTGGACCTGGAAACCACCTTCTCATATCTTTAGTGGCATCAGCCG
AGAGGTCAGACAGTTAACATCCTGAGAAGGGCTCTGGCATTTGGTCCTAGTTCTGAGCCTCTAGGACAAGGAGACAG
AAGCTGTGGTTTGCAGTGTAAAAAAGAGATGTGGCTGGGCAGTGGTGGCACATGCCTTTAATCCCAGCACATGGAA
GGCAGAGGCAGGTGGATCTCTGAGTTCAAGGCCAGCCTGGTCTACAGAGTGAGTTCCAGGCCAGCCATGGCTACACA
GAGAAACCCCGTCTCGAAAAACAAAACAAACAAAAAGATGTTAGTCCTTCCACTCACTTCCCATGTCAGGGTTACA
TGGTACACTAGAAGGCCGAGAGGCCTGTCCTGAGGTCTAGCCCTGCATGACTGATCTCGAAAACTAGAGATTTCAGT
GGACTGCTCAATGAGAATGGAGGGAGTTGAATTTCCTGTACTTGAGGTACCTGTTAGCTGAGTCCCTGGAGGAAGT
GATAAGCTCAGAGATAAGAAAGCAGAAACTGAGCAGTCTTCAATTCTCCAGGTCTGAGGTAGGATTGGGGGTGGGGT
GGGTGAAGCTTGAAAGGAGGGGAGAAAGAAAGCATAATGTTCCTGGTCAGAGATCTCTGGAAGAGGAGTGAGAAGGA
TGCAGGTCCAGTACTCTGGTTAGATGTGGGAGGTGGAATAGAAGATGGAATTTTGAGTGGGTAGGGGCTGCTAAGGT
CTATGTTGCTCTTATGTACACGAAATCTTTTCACAGGGCATAAAGTATGAGGAAGTTAGAGTCTTGGCTATGGAGAA
GTTAGAGATGACTGAGTCGCTGTGGATAAAAGAGGGAACTTTGTACACAGGGCCTGGGGTAAAAAAAAAACCCTAGG
TCACACACAGGAGGAAGTGAAGTACAGGCTAGATCTTAGACCATATCTTTCATTGCTGGGTGGGTGGTTTTGTTGTT
TGTTATAAAACAGGGTTTGTTTGTTTGTTTGTTTGTAATAAAACAGAGTAGCCTTGACCATTCTGGAACTCAC
TCTGTAGACCAGGTTGGCTTTGTTTGTTTAAAGGCAGAACCACATTCTGTAGCCCAAGCTAGCTTGGACTTTATTA
CAGAGCCGAGGCTGGTCTCCATCTCACAGTAGCCTTCCCACTTTAGCCTCCCAATTTCTAAGATCATGGGTGTGCCC
TTCTTGACTTGGTTTGCGTAGTGCAGGGTTCAGATCCAAGGCTTCCTGAATGATATAGACAAGCGTGTTACCAGCTA
AGCCACATCCCCACGGTCAAAGTTGTAGGTGTATGTTTGGGGTGAGTCTGTATGTGTTCGCATGGAGGTCAGAAGTT
GGTTTTTCCTTCCAGGAGTTATGTCCCAGTAAGCCAGCTCTAGTTTTCCAGCATGGCAGCACACACTCCCGTGGAT
AGGATGCTGACTCCCTGGGAAAGGGAAGCAAGAAGTATAGCTTTGAGTGTTTGGATTTTGGGTTTTCTTATGGGTAG
GGCTAGGATGAGCCTAGAACCTAGATGACCAATTCATTTTTATAGTTTATAGACAAGTTCCATATATTAAGACACAT
CCTTTTCAGAA

*Fig. 1M*

Mouse Calb1 Promoter: GenBank Reference No. L42901.1 Gene ID: 12307

```
GATCTTTCAGGAAACACTAGTAGGTAACAGCATGAGTCTCTCCCCAAGAAGGCTTGACTAATCTATTAGAAATCCTA
TGTGTGGACATGTTCATAAGAGAGCATGATGGAATCCTTCATGTGCTTGAACCCATAGTAAAATATCTGAGCATTTT
CTTTTCCCCTTGAAGGCTAAGAAAGCATTCATTCAACCTGAAAGGTTCTGGTTCTCCCATATGCATAGTGATTTGAA
CTGCCATGTCTTAGTCAGGGTGTTTATTCCTGGACAAACATCATGACCAAGAAGCAAGTTGGGGAGGAAAGGGTTTA
TTTGGCTTACACTTCCAGACTGCTGTTATCACCAAGGAAGTCAGGACTGGAACTCAAGCAGGTCAGGAAGCAGGAGC
TGATGCAGAGGCCATGGAGGGATGTTCCTTACTGGCTTGCCTCCCCTGGCTTGCTTAGCCTGCTCTCTTATAGAACC
AAGATTACCAGCCCAGAGATGGTCCCACCCACAAGGGGCCTTTCCCCCTTGATCACTAATTGAGAAAATGCCTTACA
GCTGGATCTCATGGAGGCATTTCCCCAACTGAAGCTCCTTTCTCTGTGATAACTCCAGCTGTGTCAAGTTGACACAA
ACTAGCCAGTACATGCCAGTAGGGCCTAAGTCTAAATACAGATGCAATAATTCAGTAACATGAAATGGGAAAGAGTT
TAATTGTGCTGGAGATTTTTTTCTCCTCTTATGACACGTGGGATCGTGAACCTGTTCACCTGAATGCTGTGTAATG
AGGCCTAAGAGGCAAGTCATAAGAGTGCTTTGCAATGCTTTTGGAAAGTTTAATCTTATGGAACAATCACAGTATTC
AAAGGGTGTGTACTTCTTCCAGAATCCTAGAAGGTGAGAGAGGTTCCTGAATATTTGAAAAATAACACCCTCCCAAT
CTTGGTTAATGAACTGAAAAATTCGGCAGGCAAAAGGCAGAAATAGTTCTTAAGTTACTTCAGAGCTGTAGAACTGA
AACACACACTTGTTTAGTGTCCTTAAACTCAATTTAATTTTGAAGTGACACCAAAAATGTCTAAAAAGAGATGTTGA
TTTTAAATGAGAGTCTAAGACTAATAGTTATTTAAGAGAAAAATGTATTTTATGAAGTTACATTTCTTCTGCTAAAA
AAAATTATCCAGGAAAAAATATTACCTTAGAAAATCAAAATGAAAAAAAAAAGAAAATCAAAATGTAAATTGAAGAA
ATTGAAGACTATAACATTCAAAGATGTTGAGGATGCCATGTTTACAGCTTGTTAATCTGAGTTGATACAAACTAAAA
GAACTAATCTAGAAATGTTCTTTAAATTTTAAATTATATATGCTTTTGTACTAACAATAGTACCCCTATGACCAGGA
AAAAATGTATATCTAAAATAAATATCTGAAGATATTTGTTGCAGCTGTTTGTCACAGTAGAACACTAAAAAAGATGG
AATGTCTACAATTAGGATGGAAAACTATGTTATGTAAACATGGGCTAATGGAGGAAGTGTCTACCGAGGAACAAACT
TTTGTATGAGGATGTGACTTGGGTAGGCTGAGATTCAGTTTTCCCTGGAAATTAAGAGGTATATGAACAAAAGTAAC
TGACGTGTATTGGGTCAAATGCCCCTTTACCTTTGTAAGCCACAGAAGGTAAGGTTAATACGTTTTATTGCACTACT
TGCAGGACCTAGCAAAGTACCTGACCCAAAAGCTGTTGATAAGTGTTCACTGAATGGATGAAAATATAAACAACTGG
GCATGCACATAATCTTTTAAGTAAAAACAATATCCTTGTTATCCTCTCAGAGTTTGGCTTGCTTTGTGTATAATAT
CAGTCTGAGATTTGTGTGAGAATCAGATAAGGTGATGAAAGTCAAAACTTACATCCATGAAAACTTTAGAGTATCAT
GGCTGCAGGACTTGTCTGGAGAAGACAATTGGTTGCCTCACAATCCCACTATTGGAGGAAACACAAATGTGGTGAAT
TCCATATTCTATGACACACGTGAAACCTGTGGCGCTTCATGAGCTCGTTTTGAAAGTTTATACCACACTGGTTTGCT
TTTGTTTACTGTAACCAGACACATAGGGTTCATTTTCAGCAGACCATAAGGTCTCAAAAGATGGACAATTAGATAAC
TTAGAAATACTTACGTAAAAGAAAACCTAAATACAGTATTTGTCATATTAAAATACCAATTGTAACATGTAGCCGGA
TATTTTTCCCACCTCTAATGATTTCCAGTTTCTGGAAAAAAATCCCTCACCTAGAGATAGAAGCAGCGCAGCTGTAA
AATCAGTGAGTGGGGCTGCTACGGAGTCACTGGTTAGCCTGGTGACATTTCTTTCAGTTTCTACTTTGTAAGATGCA
AGTAACTAATGGCATCGATAAAATCACTTCCTTCCTAACATCTTAAATTCTTATAAGTTAATTCTACTACATTCCAA
TAATTCTGCTTCAAGCTCAAAAAGTAACAACAGCAAGAGCAGCAGACTCCTGCATTCTGCTGTCTCTAAGCATAGCT
CACATCTTAAACAGCCACGTGATGGTCTCCATTAGCGCAATATGAAGCATTGTTACAATTAACCACAGCAACGTATG
CATTAATCAAATTAAACTAACACTTGACATCTGATTTGTTCAAATACTCAACTGCCTCGATAAATACTAAGTAGAC
AAAATCTCCACTGACGTGGTTTATCAGTCAGCTTTCCCTTCCATCTGAAAAAAATCAAACAATTCTAGGTATGTTG
CTTTACTCTAACATTCAGGAGTGAAAGCCTCCCTGAACCTGGGGGATGTGAGGAGAAATGAGTCTGAGCAAGGGATC
CCCACCACCTGCTGCTTCCTAGACTCCAAAACTCCAGCTCCAGCTATTTCCTGGGAAGAGAGAAATCGGAGGGGAGG
GGAAGAAGGTTGGTGAGAGCAAGAGGCGGGAGCTAGGAAAAGGAGGCAGGAGGAGGCGTGGCCCGGCCTGGGGCCGG
CGGGATAAATACAGAGAACTGGGTGCGGGGTGCGGAGAACTCCGGAGGACGCCCGAACGGAGCAGCACCGCGGACAG
CGCCCCGCCGCCGCGCCCAGCTCAGCCTGCGCAGCCCTCTCGCCCGAGGTTCGCGCTCCGCGCACTCTCAAACTA
GCCGCTGCACCACG
```

*Fig. 1N*

Mouse Nmu Promoter Region: GenBank Reference No. AC133184.3 Gene ID: 56183
```
TAAAAATAGTAATGGTATTCTTTTAATTGATCTTCAGGGTTTCATTCCTACTACTCTCTGTATTTCCAGTAGCAGCC
CATTCTCCCTAGAACTGCGCAGCTCTTGGGTATGATTTGGCAGTACCTTACCTTTAGTTCCCTAAAGGAAATGCTCC
TCCTACTAAACTGTGATTCCCTCAAAGTACCTGTCTTGCTTATGTTATAGTGGGTCACACATTCATGCCAGATGCCA
GGAAACCGAGGCGAGGAAGAAACCTATGTCCGTGCTCCTTCCCAGGCTAGGTTGTCTGAAGAAAGATAGCAACAGTG
CACTCATATACATAAAATAAATAAATAAATCTAAAAAAGAGAAAAGAAGGAAGGAAGGAAGGAAGGAAGGAAGGAAG
GAAGGAAGGAAGGAAGGAAGAAAAAGATGGAAGGAAGGGAAGAAAGAAAGAGAGAAAGGTTGCTAGGAATTGA
ACTCAGGACCTCAGGAAGAGCACTGACTGCTCTTAGCCGCTGAGCATCATTCCAGCCCCCTCTTTCTTTCTTTCTTT
CTTTCTTTCTTTCTTTCTTTCTTTCTTTCTTTCTTAAAAAGAACTTTACACTGCAGATATGTCATGAATATTA
AATGAAATTGCACGAGAAAGTCCGTGGCTACATGACCCCAAGATGCCCCGTTCAAAAACAGCAATGTGCTTCCGTCC
TGCCCTTTCCTCCGAGCTCCTCGCCTTTCAAAAGGAGGTTAAACAAGATCAGATGCCCTTTTTTCTGCAGAAGGAA
ATTAGAATTGTATTTCTCAGTGTCCTGTTAAGAGGTTGGTTCCTGGAGTGTGGGAATAGCGGAAGTGAGGTTCCAAA
GTAAATTAGAGAGAAGAGCATCCTTCGGGCAGAATGGCCACCTGAGCCTTGGGTGCCCCACCTTCTAACCTCTGCAA
CTGCACCCAATCCCAAGCCCTCCCCATTCCTCAGCACCATTTTACTGCGTCTCTAGGAATGGATTCGGACTTTGCAG
GCATTTGGAGGTTTAGATGGTATCATCTTCACCCACATTGTGGTGGAAGTAGCATCACTCTGATGCCCTGGGCATTG
GGCGTTGTGTTTCCCAGGGAAAGAAGAGAAGTGTGCCTAGACAGCAGGGGGACAAATGGGCCGGCTGGGTATACTGT
GGCATCTCAGGCGACACAAGGGAGAGTGTGGCCACCTCTTCCAACTTGACCACCCTGATCTCAGGCTCTGGGAGGCT
GCTACCCCCTCCGGCTCCCACCCAAGTCCTTCCACAGGTGGGAGTGGACCGCCATGGTTTAATTCCATTCTCCAGCT
CAGAGCCAACTGCGTGGTGTCCTGAGTCAGACACTCGGCCAGGGAGCGCGTGTCCTGCGGGGCGGCAGCAGGTCCG
GGTGACGCCAGGGAGCCAGGGGCGGCGAGGTCACGCGTGAAGACCACGCCAGCCCAGCCCACGTGTGCGCCAGATTT
AAAAGTTGGTGGCGCGCGGAGATGGTCACTTTGGTGTCTGAGCTCAGCAAGAGGAGGCGCACAGGACACGCTGAGGG
ACAGCTAAAACACCCGCACAACACAGGG
```

*Fig. 10*

MRCSPGGVWLALAASLLHVSLQGEFQRKLYKELVKNYNPLERPVANDSQP
LTVYFSLSLLQIMDVDEKNQVLTTNIWLQMSWTDHYLQWNVSEYPGVKTV
RFPDGQIWKPDILLYNSADERFDATFHTNVLVNSSGHCQYLPPGIFKSSC
YIDVRWFPFDVQHCKLKFGSWSYGGWSLDLQMQEADISGYIPNGEWDLVG
IPGKRSERFYECCKEPYPDVTFTV (SEQ ID NO: 21)

MRCSPGGVWLALAASLLHVSLQGEFQRKLYKELVKNYNPLERPVANDSQP
LTVYFSLSLLQIMDVDEKNQVLTTNIWLQMSWTDHYLQWNVSEYPGVKTV
RFPDGQIWKPDILLYNSADERFDATFHTNVLVNSSGHCQYLPPGIFKSSC
YIDVRWFPFDVQHCKLKFGSWSYGGWSLDLQMQEADISGYIPNGEWDLVG
IPGKRSERFYECCKEPYPDVTFTVTMRRR (SEQ ID NO: 22)

MRCSPGGVWLALAASLLHVSLQGEFQRKLYKELVKNYNPLERPVANDSQP
LTVYFSLSLLQIMDVDEKNQVLTTNIWLQMSWTDHYLQWNVSEYPGVKTV
RFPDGQIWKPDILLYNSADERFDATFHTNVLVNSSGHCQYLPPGIFKSSC
YIDVRWFPFDVQHCKLKFGSWSYGGWSLDLQMQEADISGYIPNGEWDLVG
IPGKRSERFYECCKEPYPDVTFTVTMRRRTLYY (SEQ ID NO: 23)

*Fig 2.*

MRCSPGGVWLALAASLLHVSLQGEFQRKLYKELVKNYNPLERPVANDSQPLTVYFSLSLL
QIMDVDEKNQVLTTNIWLQMSWTDHYLQWNVSEYPGVKTVRFPDGQIWKPDILLYNSADE
RFDATFHTNVLVNSSGHCQYLPPGIFKSSCYIDVRWFPFDVQHCKLKFGSWSYGGWSLDL
QMQEADISGYIPNGEWDLVGIPGKRSERFYECCKEPYPDVTFTVIIRRRPLFYAVSLLLP
SIFLMVVDIVGFCLPPDSGERVSFKITLLLGYSVFLIIVSDTLPATIGTPLIGVYFVVCM
ALLVISLAETIFIVRLVHKQDLQRPVPDWLRHLVLDRIAWILCLGEQPMAHRPPATFQAN
KTDDCSGSDLLPAMGNHCSHVGGPQDLEKTPRGRGSPLPPPREASLAVRGLLQELSSIRH
FLEKRDEMREVARDWLRVGYVLDRLLFRIYLLAVLAYSITLVTLWSIWHYS

*Fig. 3A*

MRCSPGGVWLALAASLLHVSLQGEFQRKLYKELVKNYNPLERPVANDSQPLTVYFSLSLL
QIMDVDEKNQVLTTNIWLQMSWTDHYLQWNVSEYPGVKTRFPDGQIWKPDILLYNSADER
FDATFHTNVLVNSSGHCQYLPPGIFKSSCYIDVRWFPFDVQHCKLKFGSWSYGGWSLDLQ
MQEADISGYIPNGEWDLVGIPGKRSERFYECCKEPYPDVTFTVTMRRRMGYYLIQMYIPS
LLIVILSWISFWINMDAAPARVGLGITTVLTMTTQSSGSRASLPKVSYVKAIDIWMAVCL
LFVFSALLEYAAVNFVSRQHKELLRFRRKRRHHKEDEAGEGRFNFSAYGMGPACLQAKDG
ISVKGANNSNTTNPPPAPSKSPEEMRKLFIQRAKKIDKISRIGFPMAFLIFNMFYWIIYK
IVRREDVHNQ

*Fig. 3B*

MRCSPGGVWLALAASLLHVSLQGEFQRKLYKELVKNYNPLERPVANDSQPLTVYFSLSLL
QIMDVDEKNQVLTTNIWLQMSWTDHYLQWNVSEYPGVKTVRFPDGQIWKPDILLYNSADE
RFDATFHTNVLVNSSGHCQYLPPGIFKSSCYIDVRWFPFDVQHCKLKFGSWSYGGWSLDL
QMQEADISGYIPNGEWDLVGIPGKRSERFYECCKEPYPDVTFTVIIRRRPLFYVVSLLLP
SIFLMVMDIVGFYLPPNSGERVSFKITLLLGYSVFLIIVSDTLPATAIGTPLIGVYFVVC
MALLVISLAETIFIVRLVHKQDLQQPVPAWLRHLVLERIAWLLCLREQSTSQRPPATSQA
TKTDDCSAMGNHCSHMGGPQDFEKSPRDRCSPPPPPREASLAVCGLLQELSSIRQFLEKR
DEIREVARDWLRVGSVLDKLLFHIYLLAVLAYSITLVMLWSIWQYA

*Fig. 3C*

MRCSPGGVWLALAASLLHVSLQGEFQRKLYKELVKNYNPLERPVANDSQPLTVYFSLSLL
QIMDVDEKNQVLTTNIWLQMSWTDHYLQWNVSEYPGVKTVRFPDGQIWKPDILLYNSADE
RFDATFHTNVLVNSSGHCQYLPPGIFKSSCYIDVRWFPFDVQHCKLKFGSWSYGGWSLDL
QMQEADISGYIPNGEWDLVGIPGKRSERFYECCKEPYPDVTFTVTMRRRTLYYLLQTYFP
ATLMVMLSWVSFWIDRRAVPARVPLGITTVLTMSTIITGVNASMPRVSYIKAVDIYLWVS
FVFVFLSVLEYAAVNYLTTVQERKEQKLREKLPCTSGLPPPRTAMLDGNYSDGEVNDLDN
YMPENGEKPDRMMVQLTLASERSSPQRKSQRSSYVSMRIDTHAIDKYSRIIFPAAYILFN
LIYWSIFS

*Fig. 3D*

MGGGRGGIWLALAAALLHVSLQGEFQRRLYKELVKNYNPLERPVANDSQPLTVYFSLSLL
QIMDVDEKNQVLTTNIWLQMSWTDHYLQWNMSEYPGVKNVRFPDGQIWKPDILLYNSADE
RFDATFHTNVLVNASGHCQYLPPGIFKSSCYIDVRWFPFDVQQCKLKFGSWSYGGWSLDL
QMQEADISSYIPNGEWDLMGIPGKRNEKFYECCKEPYPDVTYTVTMRRRTLYYGLNLLIP
CVLISALALLVFLLPADSGEKISLGITVLLSLTVFMLLVAEIMPATSDSVPLIAQYFAST
MIIVGLSVVVTVIVLRYHHHDPDGGKMPKWTRIILLNWCAWFLRMKRPGEDKVRPACQHK
PRRCSLASVELSAGAGPPTSNGNLLYIGFRGLEGMHCAPTPDSGVVCGRLACSPTHDEHL
MHGAHPSDGDPDLAKILEEVRYIANRNRCQDESEVICSEWKFAACVVDPLCLMAFSVFTI
ICTIGILMSAPNFVEAVSKDFA

*Fig. 3E*

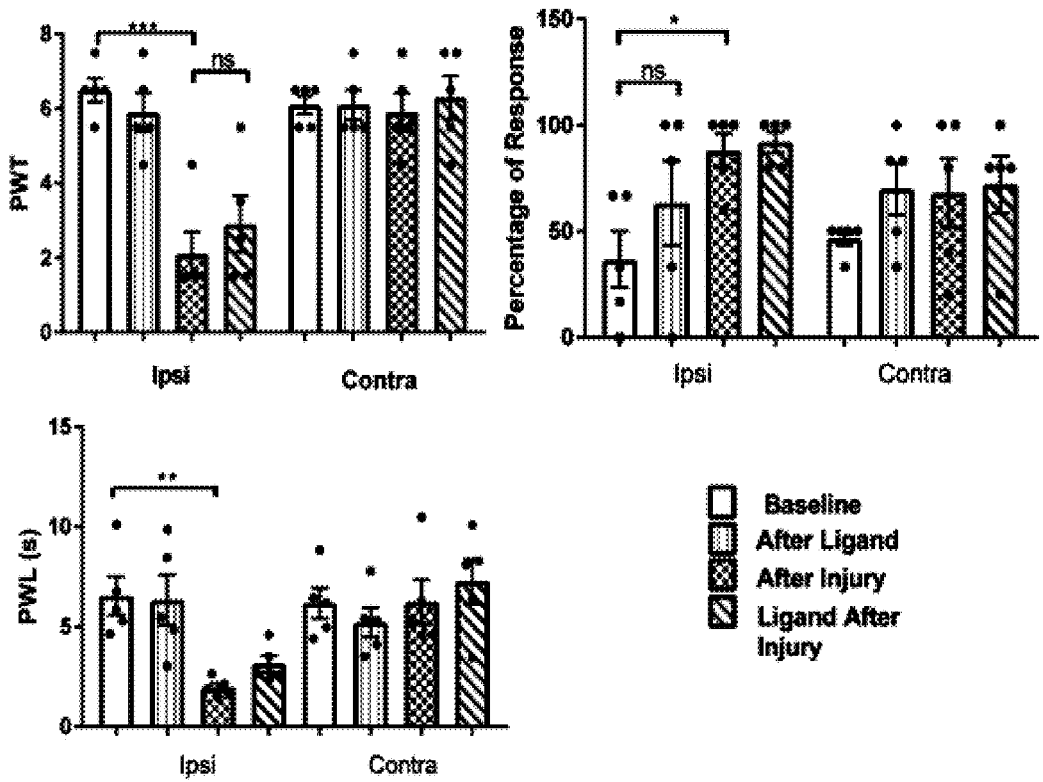
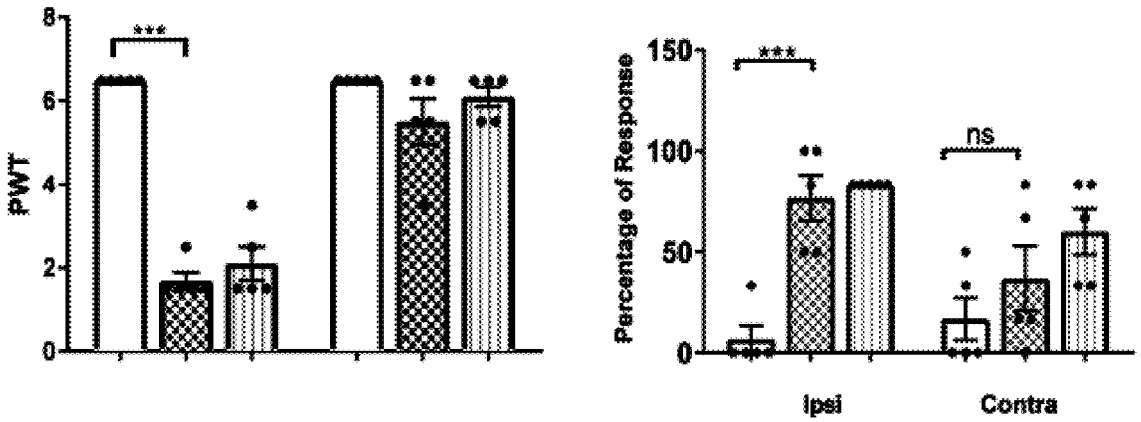
Fig. 13

SEQUENCE LISTING

<160> NUMBER OF SEQ ID NOS: 25

<210> SEQ ID NO 1
<211> LENGTH: 3000
<212> TYPE: DNA
<213> ORGANISM: Homo sapiens

<400> SEQUENCE: 1

| | | | | | |
|---|---|---|---|---|---:|
| ttctaaccga | aagaagaaaa | ataaaacccc | acgagattaa | aaatagtgtg | aaaaaaatat | 60 |
| cctaaaggga | agactccgtg | ggagaaatga | gaaccctggg | gaaagcactt | ttccagatag | 120 |
| ctaacaagct | ttcaatatgg | aaatacagta | aatgatgaaa | aagagaagca | cagtttaaaa | 180 |
| tgtaggagca | ataaataaag | ccgtatttat | aaagtttttc | tcaaagtgta | cgtgggaaat | 240 |
| ggcaataagc | cactacgcag | aacataggca | ggttttaaaa | tcagaaatat | gtgcccagcg | 300 |
| ctcaggcttc | gaaagccccg | tgcattttag | atcgctagtg | gataaaacac | cctcaagttt | 360 |
| ctatccgtaa | agcctcgaaa | ttttctgcag | tatttagaaa | atgaatttaa | atcttaaaac | 420 |
| cctctaatat | tttattagaa | aagattgcaa | agtcccccgc | accgctgtgt | aacagctagc | 480 |
| aaactcaatc | tgcatgcgaa | tcttagcgaa | tgggtagttc | atcccttaat | gatgctggcg | 540 |
| tatgaaaggc | tctaaagcag | ctctacccac | ccagacctca | cttttagacc | cagagccgtt | 600 |
| atttctgact | tcaagaaatg | tctttcgagc | tctcggaggg | aagacacaga | aaatagaaaa | 660 |
| gcataatgga | aatgggcaca | aagctgaaga | cagcatcctt | caaagacaca | cgacacttgg | 720 |
| atcccccgct | gacgaaccga | gggacctacc | ttttggatta | ggacgcagct | ggcttggcgt | 780 |
| ttccaaccgg | agcagcccgg | cagctgagcc | aagttcaggg | aggaccagcg | ggcggctgtc | 840 |
| tcttaaatag | ccccacccgg | cggcgtcggc | cagtcatgta | tttacccaac | gctgacgcag | 900 |
| actggcagta | acacgtgctc | agagggcggc | cactggggcg | acaaccggtt | gaagtggctc | 960 |
| ctgggagaga | gggggaggtg | gtctagtggg | gtggagttaa | tccctcccac | gcgcggtgcc | 1020 |
| gggtgtccgc | ccctctgggt | ccgagaagc | ttccgcccaa | ccctttccag | gtgccgctcc | 1080 |
| cctgcgcatt | ccagagcagt | actctccaag | gtgggaaacc | taggagtttg | gagtctcctc | 1140 |
| cgggatggag | aagctgccgc | tagcttagtt | cgctttgggg | accggagggg | ctagaaagga | 1200 |
| aactggggc | gggggtgggg | ggtggacact | gggcaggact | gagcatcagc | aaggcgtgat | 1260 |
| tctgaaaggg | aggggcgtc | ggcccccctac | cccggagcgt | ccgaggcgct | ggtcttcata | 1320 |
| cctgtgtcgg | ctctttcgaa | ggagagagga | ggagtcgggg | tcttcacttt | cttctcagcc | 1380 |
| gcattaaaag | ccctcgcagt | tctccaggtt | tccgagggcc | agtgttctgg | gtcagtgaaa | 1440 |
| gggctctggc | cacagctggc | tcttggtgtc | ctgggcctct | cttgacgcag | ctgtaaaatg | 1500 |
| cggatgacac | catctggttt | tgctcagagg | aatccggttt | gggaaaggga | tgtgttttct | 1560 |
| tcccgggcca | agttaccacc | acccgcggcc | cccactgttc | cccgttgtcg | acaagcggcg | 1620 |
| ccagcgaggg | tcctggggaa | cttgaccacc | gcaccccgc | aagctcgggt | agaccacggc | 1680 |
| atccgcccct | cgcacctttc | ctgagggcc | acacactcac | accccagga | cagtaccttc | 1740 |
| cagaactcag | ctgcgcagcc | tggaggtgag | gacctcaccc | ctagtcagtc | accgtccgg | 1800 |
| tggagggaag | ggaggcaccg | aggctgccgt | gcgcctttcc | ctgcacgcgg | ttactctccc | 1860 |
| ggctccggag | cgggccgacc | tggagcccct | cagtgcgctc | tggtcgtcta | caccctgaaa | 1920 |
| cccttttgagt | tcgagtccgc | ttgctggtgc | ttgagttcgc | cgcgtccctg | caaaggcact | 1980 |
| gccaaccccca | tttcacagac | cgcaaaccga | ggcgcgagga | agagcagcgc | cttgccaagg | 2040 |
| ctccacaaca | cgcccctcgc | cctctccgtg | caccgaggcc | gcccagcctg | ggacctggag | 2100 |

```
atcaccaggc cttgaacctt gggacctcaa ctcctctccc tttctttccc ccacccgtct     2160
tagatgcaag gagaaagatt tagaagcgct tattttaaaa tcggaatccg tattccgctc     2220
tggaattccc tctggaatgg agggactgtg gcaacgccag tgtgagggtg gagtgggcga     2280
ggcggggtgg gggggttggg ggggcggccc agagacgcct ccggttgctg ctccactttc     2340
taatcctgag aggcagctgc gtttctgcaa cctatgggca acatgtttga aagagctgaa     2400
gctgattaaa tgctttccag tggtttcgcc acgagcctgc taaggtttgt gtagttcagt     2460
tgcgaaaaag agtcttattt gtgattgtgg caagacatgt ctggaaacat aaacttgtta     2520
tcgaaatacc cccagagctt ctaattcagt aggtctgagg aagggcccaa gaatccgaat     2580
tccttccttc cttccttcct tccttccttc cttccttcct tcctttcttc ctccttccct     2640
ccttccctcc ctccctccct tccttcctcc ctccctccct cccttcctcc ctccttccct     2700
ccctctctcc ccttccctct ttccctctct cccttccttc cttccttcct tccttccttc     2760
cttccttcct tccctccctc cttccttcct tccttcccnc ctccctccct ccgtctctcc     2820
ttctccctct ttccctcttt ctctctctct ttctttcttt cttctttatt tctttctttc     2880
tttcttcatt tccttccttc cttccttcct tccttccttc cttccttcct tccttccttc     2940
ctttccttgc ctttccttct ttgagacaga gtctcactct gtcgcccagg ctggagtaca     3000

<210> SEQ ID NO 2
<211> LENGTH: 3000
<212> TYPE: DNA
<213> ORGANISM: Homo sapiens

<400> SEQUENCE: 2
aaacataggt cataaatatt tagaaaaaaa tgcatccgtg ctaaacacat acagactttt       60
tccctttgtg ttattcccca cataatacag tataacaact atttacactg cctttatatt      120
atattaagta tcataagtaa tctagagatt atttaaaata tatgagacga tgtgcatagg      180
ttatattcaa ataccacacc attttgcatc agggacttga gcatccacag gttttgatac      240
ctacaggagg tcctacagcc aatcccctat gcatactgag tgatgactgt atgtcaaatg      300
tgtttaaatc caggaagtca taataatcct aattttttaa agtgggtctt attaaaaggt      360
gttaatttac caattcatta ttttcaaaat tggtagagag acataatcaa gcatttatcc      420
catctttcct atattaataa tgctttagaa taactagttg ctgagaaaca tgaaagaaac      480
aagtctgcct accagacaaa taatgaatga taaaatcaac atagcactgt tttgaaaata      540
ctaatgaatt aatagatcta gaaaatgata gtcaatggct gctaacaact caaaggaga      600 aacaaccaca tatcatgtgc ttcctaccag aacaacacaa cacatgtgaa gtagtctcat      660
caaaaaaaaa aaaaagaaa aagaaaagga aaagaaaaa aatgtacaga ggatcaaact      720
tctagataca actaccaatt aacaggaaat aatcgaaaca gagaaacaag ttaaaaggca      780
atcagcaaag tccagaatgc ggtacactct cctgacctgt cttatcaata aactacaata      840
gagagagaaa gagagagcga attacagatt cagggagatt taagaaacat gcagtagaag      900
gaatgttcgt gtccctccaa aatgcatgtg ttgaaatcgt aacccctaag gttatggtat      960
taggaagtgg ggtctttgga agataattag atcatgatgg tgcagctctt atgaatgaga     1020
tcagtgcccc gataaaaggg actttgaaga gctctctcat tctttcctgc catgtgagga     1080
tataacaagg agacaatatg acagtctgta acctggaaga gggccttaaa cacaaccaga     1140
ccatgctgac accacgatct cagacttcca accttcgaaa ctgtgagaaa taaatttctg     1200
```

```
ttgtttacgt cacccagacc atggtacttt cttacagcag cctgaactaa caaaaccaat    1260
tgtaatgtat ggacttcatt ataattctga tttcaagtag taaactgtgt gggccggaat    1320
taggaagcaa tgagaaatat ttgaatgcta actggatatt taatgtaagg aattattta     1380
tgttgtttta ggtgggataa tggcgtggat atgtttttat ttttttttaat tcctacccttt  1440
atacagacat gctgaaatat ttacagttga aatgattaac tgtctgggat tttttttcaaa   1500
ataatctcag tgcagaggaa actggaaggg ttgtagatga aacttggaag tggatgtttc    1560
tctctacttt tggatatgct tataattttc catataaaag ttctgaaaac ggaaaataaa    1620
atgctcacat tgtgaggcta aggccaaaag aaatcagaga tgcatgagaa tttccaaatt    1680
caggattatt taagaacaac atagagaaaa aaatacttct ggtttgagtt gcaaaaattt    1740
atttcttta tgcaatatac taaaaaatca taattaattg aaaaatataa tacttcatat     1800
gtaaagggga gaaaactact ccaccaaaga tgtcacatct tttaattcat ttggagatca    1860
aagaaatgtg tctgccaggc aaccaagggc tcatggaaag gtgtggtttc tgtacaaatg    1920
ctatttgtct aatattttgt gctgttaatg actgtcccat tagcatcttc actcacttca    1980
ctttcataga aaggagaaac atgatttata gagccctta gtgacaaggg tgaggatcct     2040
acacactatg ttgctggttt cctagtcttc agcaagaaag tgtaggagag aagcaaaaaa    2100
cgtcctgttc aacccctgct cctggatgtg gcaaggaaga ggagttaccc ggcttgaaac    2160
aaagagaatc ctaagtctga cacacaatgt catgtttaaa ttccccttc tccaaaatgt     2220
aaaataaatc tgcttccatc ttctaaaata ctatgggact aaacatcctt tgttatgct    2280
aaggaaaagc cagtattcgc gttgatttag aagagggatg ttctggttat agaacgatgc    2340
tgtgtctcag aaacacttaa atactattaa gctagaaata gaagggaaaa taatgcttcc    2400
ccgcatctcc cctcaagtgt agtcctcttt ttttagcctg atttccgacg aaatgtctga   2460
atgcctacag ttatttggcc atcctgaaaa gtgcaactta tcctgacgtc tcgagggacg    2520
gaaaagttac cgaagtccaa ggaatgagtc actttgctca aatttgatga gtaatatcag    2580
gtgtcatgaa acccagtttc gaaggagagg ggaggggggcg tcagatctgc agacggaagc    2640
aggccgctcc ggattggatg gcgagacctc gatttttccta aaattgcgtc atttagaacc   2700
caattgggtc cagatgttat gggcatcgac gagttaccgt ctcggaaact ctcaatcacg    2760
caagcgaaag gagaggaggc ggctaattaa atattgagca gaaagtcgcg tggggagaat    2820
gtcacgtggg tctggaggct caaggaggct gggataaata ccgcaaggca ctgagcaggc    2880
gaaagagcgc gctcggacct ccttcccggc ggcagctacc gagagtgcgg agcgaccagc    2940
gtgcgctcgg aggaaccaga gaactcagca ccccgcggga ctgtccgtcg cagtaagtgc    3000
```

<210> SEQ ID NO 3
<211> LENGTH: 3000
<212> TYPE: DNA
<213> ORGANISM: Homo sapiens
<400> SEQUENCE: 3

```
gattattttc agcaattacc taataaaggt ctgacataag taacagtaca agcttagaaa     60
tctacctact ttagagatgt tgtaatcaac aggtacctaa caggtaacat ccacttaaga    120
aggccaacac aggaatatta ttaaaggaca atgcttaaaa tctttatcag atattttaag   180
aactaggtaa ccccttagaag gatctaaggt atgccgggca tggtggctca cgcctgtaat   240
cccagcactt tgggaggccg aggtgggcgg atcatgaggt caagagatcg agaccatcct   300
ggccaacatg gtgaaacccc gtctctacta aaaatacaag aattagctgg gcctggtggt    360
```

```
gtgcctgtag tcccagctac tcgggggget gaggcaggag agttgcttga acccaggagg    420
tggagactgc agtgagccga gatcacacca ctgcactcca gcctggtgac agagagaagc    480
tccatctcaa aaaaaaaaaa aaagaaaaaa gaaaaaggat ctggggtaaa aagcctttaa    540
aataaaaaca gttcacccat ctccatagca aggtgtctac aatcctgcat taaaggcatc    600
atttaggaag ttcgtagggt acttttaag tggaaaaata catacttaac ctttatccct     660
acaacaaatt gttttattgg tttatgtgta gcttgaaggc attagattag agcaagaaac    720
aaaaagccta acacattaaa gaaaatacca attagaggtc aaagtttatc tacatcataa    780
ttttaccaaa gttatacatc ttttttcccc aaaagaaaag tagcatatag catctatttg    840
aatttgaatt atttgacata acttaatgtt tcccctattc ttgaatattt atcacatatc    900
tcaattttca cattaacaac taatatccat gttatatatt taaaatgaat tccattaat    960 tcttctcccc cttttttcta attaattagg gatcaatttt gtcaacatat tgaagaaatc   1020
atctgaggaa aataagaatc acatttcctt tttactatta gactgctatc acacatttta   1080
aaagatcatt ctttgtattt gcaattcaaa agcagagaaa acaactaatt taattatcat   1140
gcaaagtata tataattttc ccgatttgtt aatcaaagtg gctttaagag gattctgtca   1200
caaagatgct ctgatagtaa caggaaagta agcacaaatc ctcactgaga ctctgttaag   1260
tgaaaaccaa gtgtttcaag cttccattgc tcccctaat ggtaggaaag cagaaaacat    1320
ctagacgtat gtatttcaca tttgtcaact aaatacttta cagaaacctt cctccatgtg   1380
agtatgttca atattgtgtt ttatgtaagt tcagaaaaca aactaaaagt aataaatata   1440
tcagttatta ttaaatttct ggtattatat gaaagactcc ttgctattct aagtaattat   1500
taaatgtttg gatttaatcg ctttgcttaa gttttgggta aaggtgaaaa agttaaactc   1560
atagattgta taatataaat caattatcta taggaaccaa tcctattttt tctcaactgt   1620
tactacatga ttgatttatt taaaaattaa acaagactca gacaacttta cattcaaata   1680
ttcacatctc taacagcact gacttgtcaa attaccccat gtatcttgaa atgcttacta   1740
caagaagaaa gttttactct aaaaggcatt ttgaacaatt ttcttttgag aactcagaca   1800
aagaatgggt atcagtgtaa ctcatgaaat acatgaagac tatcatagaa aagtgacttt   1860
ggtgaatggt ggttatttag gattgtctcc tttccaaaag tacaatctct ttttttatgg   1920
tgaaaagagt attataacag ggaaagaaag ccgatgcaat agtaaaaact gttgagaagg   1980
gaattataca aagagtgaga catggcatca agaatgaatt caaaaagagc agaaaaatat   2040
aggcataaaa agagataatg tacagaaaaa aagtcagtga tacaacaaca caaattttta   2100
cctgctagaa tgtaagtaat ttagagctgg attttataaa catgaaattg ttttctaat   2160 acattcaacc aaaagtcagc acacatagtt cagtcatctc tcattactta caataaaata   2220 ttttctatt gttaggaaat aatatcttat tccctggatc tattatttct tttattgat    2280 tttctttcta ttctctaaac ttaattgctt aatttttata actgattctc tgtctctatt   2340
ccatcttatt ccagcatgga ttatttaaaa cctgtattag ttttggaacc actaaacatt   2400
tgctcagaag tttgaattac cagagaagca ccctaactct tcaagaactt ccaagcctaa   2460
ggaatcactg atttcatgca ttcatcctgg agattttcct taaaaattag aataacaga   2520 tctcatgttt cacaaaatca aaatgacaac ttttggagtg ggggaatgag aagtgggaaa   2580
aggatgatac tggggttct tgtcagtat gctgtatgta tgctgtatgt cagtgcagtt    2640
gaatgactcc ttctgtgcgt cagaaatcca agcagcagc agcagcaatt agggaagatc    2700
```

```
gtcactttca ctcaaggttc agaaatgggg gaggagagca ggggggacaa aggaaaaggg    2760
gaggagaaag cagggcaaag aggggaggga tggaggtgaa gatagggcac atcctgcaaa    2820
gataatgtct gtacaatcaa tgacatcatc ctcctgctta tatatatagg ggaatggcca    2880
gagcacctct catagttcac tcactttcaa agccagctga aggaaagagg aagtgctaga    2940
gagagccccc ttcagtgtgc ttctgacttt tacggacttg gcttgttaga aggctgaaag    3000
```

```
<210> SEQ ID NO 4
<211> LENGTH: 944
<212> TYPE: DNA
<213> ORGANISM: Homo sapiens

<400> SEQUENCE: 4
ggatgtatta gctggtgtcc tggaagaggc tgcttcctga acgtttccaa tcaaggaaat      60
aaaggaaagt atagagatgg aaagagggag tcaggtcacg gtagaaatca ggatgcaata     120
gcagcagaaa tgcatagaaa aaggagtttc cttaggcttg gaaatccgta ggataaccag     180
cgctccagac cagttagaaa tgtgtgtgtg tggtcaagcc ccagcagtcc tttcttcttt     240
gtcctttatt aacaggcaac tgcatttccc taagggtctc tgtgattttg caggaatttgg    300 gggagggtcg atagcatcaa catcacagtt gaaccaacac tgccctgata tgcaccaggc    360
attgcgcttg gaactgggga taaaccgggg aacaaaacag aggtgcttcc acagaggtgc    420
gtactagtga ctgccggagc tctggaagag gtgaaggaga aagggtgtcc cacgtagacc    480
caggacacca gagagcgtcg ccactaccaa gtttaaaaac tcagacggcc tggtttgcca    540
tccacaccct gttcccagtc cagtccttcc aaaggtggga atggtgcatt atttaaattc    600
cattctcttt atcccagagc gaaaatgcgt ggtactcggg tcagaaactc aggctagggg   660
gctcgggtcc tgctgcaggg tggggcgcgg gcaggcagcg gggcggggtg aggcgaggta    720
ggccgggggc ggcaggcggc gaggtgacgc gcggcgggga ccgcgcagcc cagcccactt    780
gtgcgcgaga tttaaaagtt ggcggctcgc cgggcgctca gtcctgtgtc cgggccccga   840
ggcacagcca gggcaccagg tggagcacca gctacgcgtg gcgcagcgca gcgtccctag    900
caccgagcct cccgcagccg ccgagatgct gcgaacagag agct                      944
```

```
<210> SEQ ID NO 5
<211> LENGTH: 2996
<212> TYPE: DNA
<213> ORGANISM: Homo sapiens

<400> SEQUENCE: 5
acaaattgaa gcaaataatt tggaaatgtg tattaaaatc taaatatgc attctattaa      60 ctaaaaatac tgcttttggg actctgccct gttgtattca gaaacatgta tagctaatat    120
aaatgtataa aggtgtttat tgcagcattg tgtgtcacag tgtactacta gaaatagatc    180
cgtatatctg taattatagt taattaataa aatattaaac tgtaaaaagt atacattaga    240
tgttgatgtt aatactggag ggatgccctt gaattaataa tagaaagttg aaggataata    300
tacaaaacat agtcccttt ctgtaaaacc agataacaac aacaaaaaaa aaacctttag    360
atatggattt gtatatttcc ataagcatgg ctcttttagt gttgattacc tcatggtagg    420
ggcagcacta aactgcttta gagctccata atctacatta gttccctcaa aagccacttc    480
atataaacat aaaaagaaca cacaaaaaaa actatgtcca aacttgctgt ttggacatag    540
ttccaaggaa gtctcccatt tatttctcac tctctctcaa gtcacagcac ctatacattt    600
ctaaatggaa atttggaagt tgccatagct tcaggaaagt gaataagaaa aaagattact    660
```

```
ttcatataaa tatttttaac ttttacaaat tgtcttgtaa tactttttgga agttaagata      720 aaattctaaa aaaccaacaa acagattatg gtgaaaatgt ttaggaattt ttaccacagt      780
gtgtggtctc ttttaggaa gaaaattaat tttaattact ttttaaaata gtagaaatgt       840
tgctcttttt tcatcagttt gttcagtcca tattcctaca tactttttct agcatttttc      900
tttgtctcag aactgtatcc aaagtctaga cattgttagc tctgtcaaga ctagcaaggg      960
tcagagtgat tcttcaagtc attccttagt cactgcattc tcactctctc ttcaaagttt    1020
attctctagc gctggtctcc aagttcacac actatattttt tcacacagcg accctggcca   1080
ctaacatagg accaatagga ccatcagtga gaatcagatg aggtatcata agtaaaaata    1140
atgtatgaac tggaaagtac tatggaagtg aggattccat taagaagatt attgaaatag    1200
gctagcttca aattgatggg tctctgaaaa ggatacttac aaaaaaactc cacaaatata    1260
ataatggata gagccctaat ctcaaaaaca taaatttgag gggtcccaaa ctcaattaca    1320
caaggttaag aatatagagc ttggtaaatt ctctctctct cttttttttt ttggagacag    1380
agtcttgctc tgtcaccagg ctggagtgca gtggcgtgat cttggctcac tgcaacctcc    1440
gcctcccagg ttcaagccat tctcctgcct cagcctccca gtagttcag attacaggtg     1500 cccaccccca tgcccagcta atttttgtat tttagtaga cgggatttt caccatgttg       1560 gccaggatgg tctcgatctc gtgaccttgt gatctgcctg cctcggcctt ccaaagtgct    1620
gggattacag gcgtgagcca ccgcgcccgg ccggtaaatt cattttaatt cactttaagc    1680
ttatattggc tatgtgtaga ttttctcttg ttccttcatt ttgttttagt acaattgtaa    1740
ttagactttt gggatacatt tttagtggac ttcaaggtcc aaaagactca aagccaaata    1800
ctccagaagt acttatgtaa ataagaaata atccaagtat ataattaatt atattaaaat    1860
acataacaca tatacatatg tatatatagt acagaacata tatacatatg tgtgtataca    1920
tacatatata ttacatatat atatatatat atatatatat acataacata gcatacattt    1980
agttagatag cttttccaac tctgatggtg acttccaatt tctgaaaaat tctccagtag    2040
gggttgcttg aaacagaaag aaggagacgt gtgtgttaag gcgactgaat ggggctgtgg    2100
tggtagcact aacgtaccta cttatgaacc tggtcagatc cttcctttct ctttgtttta    2160
gtttactcac tccttctaaa ctgaaaggca gtaaactcta gtatctgtaa gatgacttcc    2220
ttatctaaga ttttaaggtt ttataattta actgtattac tttccaatta taattctact    2280
tcatgctgaa aagaaatcca taatctagct tttttcgtgt tggcaaggtt agttcataga    2340
aaccatctta agaacattg acatgatggc acaaaataga gtgattattg atagcaatca     2400
actcattgta tacattaatc aaattattct aatgcgtgcc aaggtttcac atgctttttt    2460
tttttcaaac aaatactgaa aagtcttgga gaaatcacac aagaatataa taatctttta    2520
tgtgatttta cccgtcatca gctttcccct tctatctgaa catttaaacc tctctagata    2580
acaagagttt tactataata ttcaggaata agattcttcc tggactagga ggatgtaggg    2640
ggaaatgagc ctctgttttc agcatccaat ctctgagcaa aggatctccc accacctgct    2700
gcttccaaca agcccaaact ccgctccagc tagctttcct gggaacagag cagaaaactg    2760
gaagggaggg gaagaaggct ggtgagagca agaggcgggg gtgaggaatg gaggctgga    2820 ggaggcgtgg cccggcttgg ggccgtcggg aaaatactga gaactgggtg cggggtgtag    2880
ggagagaact ctggaggaac gctagctgag cagcaccgag gacagcgccc ggcagcgccc    2940
gcgcccaggt ctcctccgca gccctgactc gcgcacacgc tgagcttttg ctcact        2996
```

<210> SEQ ID NO 6
<211> LENGTH: 3000
<212> TYPE: DNA
<213> ORGANISM: Homo sapiens

<400> SEQUENCE: 6

| | | | | | |
|---|---|---|---|---|---|
| ccaaaggact | tggacctgaa | agtttgtagc | attgcaggga | cagccatctt | gccaccctca | 60 |
| ggggtcaacc | agtttgagag | agtggcacaa | ggtattgctg | agaagtaaga | gaaacagcat | 120 |
| cttcctgaca | gcatttgagt | tctggatcaa | accatgcttg | aaccttcgtg | gacttttcag | 180 |
| ttgcacgagt | tagcaaatcc | cccactgtct | taagccagcc | caagtcagac | tttctcatca | 240 |
| cttacaggca | aaaacagacc | tgactgataa | acccattttc | tggcatcaag | gcccttgtat | 300 |
| aattaaccaa | attaataaaa | tgaagcctgc | ttcaatcagc | acagattcag | agcaaaaaaa | 360 |
| caaacaaaca | aaaaaaaaaa | aaactagatc | atgtttccag | atatatgact | cgggttttag | 420 |
| gacatctcta | ccctacttta | agtattgtag | ggggaaagat | cctccagaat | cagaagtgct | 480 |
| cagtttaaat | cctagctctc | ccacctactt | cctacctgtg | tgaccttagg | taagtcacta | 540 |
| aacctctctg | agattctatt | tcttcgaacg | tctgagataa | agcacataaa | gcactaggta | 600 |
| cgcagtaggt | gctcaataaa | tgcaccccc | ccccaacaca | cacacacaca | cacgatatgg | 660 |
| ttcagcccat | tcagatttgc | ttaattagag | gtacatgaag | aagacctatg | gggacaaaga | 720 |
| ggaaggccat | ctgggctcct | gagaattcac | ccacagtagg | tgctgctccc | gtcttccggt | 780 |
| cttattctgg | aagcaggata | gtgtggtaga | aaggagcaag | tgctttggag | tcagagaacc | 840 |
| ggggctgaaa | tcctacctcc | attctgtgat | cttaggcaag | ttgcccaatc | tctctgagcc | 900 |
| ttgttcttcc | atcattagta | aaaagagag | ggttttgcct | acctcttaag | gggatacaag | 960 |
| aatcaaagtg | cgatgctgtg | cacacagaac | ccagcacact | gttcaacaaa | caagtgtaat | 1020 |
| tattttccca | ggccccagcc | agcgatcttc | ctcaagggtt | catcctcaag | gttctcctgc | 1080 |
| atcccggctc | cctgagctca | gccatgccca | cgacttgacg | agatcaactc | cttgacttct | 1140 |
| ctgatgacaa | agcccccagg | gtccagccct | gacctcactc | cagagttcag | acacatctcc | 1200 |
| gccagggtgt | ccttcaggtc | ccctaaaccc | agcatcagct | cttggctctt | ccactactct | 1260 |
| ctgggggatt | tgggtaagtc | accctggcct | tggtttcttc | atctataaca | tgatgtcatt | 1320 |
| tgtagaagtt | tgtagccgat | caccacggag | gctgtcccag | ccctaacatc | ctaggattca | 1380 |
| acaccactta | ctctatcatc | ccttcgactg | agcactacct | cctccctaca | ctccctgcct | 1440 |
| tcaaagtcaa | caccttcctt | cttcagcaaa | cccccacctg | aatatttagg | gtcagcttgg | 1500 |
| atttgtccct | cttgttcatg | ccacagcccc | aattctggaa | gcttctctcc | aagaggtgct | 1560 |
| cccctatctg | cacactcctt | cctgttgcca | ccaccagcaa | cctagctcag | gccccagcac | 1620 |
| cacacctcaa | ggaggcccca | gtcccagctt | ccccccatgca | gcctgccctc | ggcccttttct | 1680 |
| atccatggag | cttccaaaca | gcctttgcat | ggagcctggg | attcctcgtg | tcactgtgaa | 1740 |
| gaactagacc | ccaccattga | caatcttcgt | gccctggaga | ttcttttcag | gttagggatg | 1800 |
| aggagaggaa | catttcatgg | tggtcagatt | agatattcac | tacgtattta | ttgaattcat | 1860 |
| ttggtcattc | atgcttctca | aaacacatcc | ctcagctggt | cctctccaat | ccaaaacaga | 1920 |
| caatgtcaga | gatctctttg | caaatcatga | agggcttggg | cctttgtgcc | tcaatgtcac | 1980 |
| acgcatacaa | tttcaggggg | tccatcttcc | cctcgcccta | gaccatctat | agggcacagt | 2040 |
| ttacctctga | ttgagctcat | gttacaggtg | gaaagactga | gaaagagaga | ggaagggact | 2100 |
| tgtctgagaa | tatgcggaac | atttccttct | accaggcact | agatcctcgc | acaaaagtgc | 2160 |

| | |
|---|---|
| tgagtccgct cccaacccca ggcccgtggc tttgagcagc aggtcactta acatctaacg | 2220 |
| tctttatgct gtttcctcat ctgtgcgaga gcagctatgt ctacctggca aggctgtagt | 2280 |
| gagagatcat atcagcatag gaatggggct cagccccatg cacagaggac agttcttgtt | 2340 |
| tcattctttt ccttgctgtt tctcttcctt tcctggcaga atatggagga aggaagcatc | 2400 |
| gctgccatct acagtggtca cggaaggctt catggaagag gcgagccctg cctgggcctc | 2460 |
| aattttgggt gctggaggga agcaggggcc aagagttatt aatagtcttg gcctgatggg | 2520 |
| cccagggagg ctgaatgtga tacagacacc cagcaccacg gttggggagt acctgacacc | 2580 |
| ggaaggggag ggggccgggg ctacggggag tgccacctcc caaaatagcc agagcagaag | 2640 |
| cctatatagg tggccatccc acctccaggc tcacttcccg acaggacttc ccaccagccc | 2700 |
| agcctttcag tgcaggctcc agccctccac ccccacccga ggtgagtggc agctaccgag | 2760 |
| gttggaggat agagggatgc agcaggatga gccagctgga agggagagct acatctcccc | 2820 |
| tgtccgtagt gacccgggga gggggtgcg gtggggtgc tggaggcagg gcagctgtgg | 2880 |
| aatgtagggc tgagagcatg cattcctgct tctccaccca gactcctggt gtggcctggg | 2940 |
| gcaaactccc cccacccacc gcccccgtg gctgggcctc agattcccca gccttagaac | 3000 |

<210> SEQ ID NO 7
<211> LENGTH: 3000
<212> TYPE: DNA
<213> ORGANISM: Homo sapiens

<400> SEQUENCE: 7

| | |
|---|---|
| cttggcctcc caaagtgctg ggattacagg catgagccac cgcacccggc ctgaaattta | 60 |
| ttttctttt tttcctttct ctttcctcac tttccttcct tctctttct tcttctcctt | 120 |
| ctcctcctcg tcctcctcct tcttcttctt ctttcttctt cttcccttct ctctctctct | 180 |
| ctctctctct ccctccctcc ctccttcttt ctttcttgac agagacttgc tctgttgcct | 240 |
| atgctggagt gcaggcttga tcgtggctca ctgtagcctc aacctcctgg gctcaggtga | 300 |
| tcctcccacc tcagcctcct gagctgagta gctgggacta caggcacgtg ccatcatgct | 360 |
| tggctgattt ttaaaaaata tttatttatt tattttagt agagatgagg ccttgctatg | 420 |
| ttgccccagc tggtcttgga ctccagggct caagtgatct atctactcac ctcagcctcc | 480 |
| caaaatgctg ggattacaag cgtgagccac tgcgcccagt ctgaagtttc tttgaaagca | 540 |
| aaaaaggaaa caaaaagagt acataggccc aaatgaagac agctgaaagt ttaatgtacc | 600 |
| tcaaattcca gccatgact aagggatgga cttttgagtct cttttcgaat ccatctcaag | 660 |
| gatttaggtt tagagtttgt gctcctttaa acagactaag agcctctgtg acaaagtaaa | 720 |
| tagagaaaat aagtgtagtc aagctctggc aggatttgga aggggcccta acgtggaaga | 780 |
| aaggagaagg ctggaattga ctaagatgtg ctatgcactg ggctggattt gttctcagca | 840 |
| gaaagcaaga aagagctctg ggatggtagc agggctccca ctaccaccgg ggccaaagg | 900 |
| ttgcagtatt tctcaggtag ccaagaggca cccatgagcc cagcccctgc ccactccctg | 960 |
| atgtcatcta gacacaagga catggggcat gagaggacat cattgtcact tctctgcaga | 1020 |
| gtcacaggaa cgtgccctct gctcctccgc ctctcggctg tccttctgcc cacggctggc | 1080 |
| ccagactctc atggcgactc actgtctccc acgcccccac tcccggcagg aaaccacttc | 1140 |
| aggggtttact gtgggctccg aaatcagcct gtgagtccta gttagggtcc cctgtgcctg | 1200 |
| actctcctct ccccaggctg caagaaatag ggatgaccag aagtcaaact gtgcccttgg | 1260 |

| | |
|---|---|
| gaacaccca cccctcacca ctgtcgtgcc aggagtctgt tcctaagacc cctccccaag | 1320 |
| tcctgtctcc tcctcttcct cccataaacc acagcagaca ctcagccacc aggctgcagc | 1380 |
| cctgcaccttt ctccagcagc cgctggcctt cgccagagtt cttgaaagcc cagttgtcct | 1440 |
| tccccagcca cgtggaggca gacggatctc tcctgggggc agcctgtagc tgtctgtgca | 1500 |
| aaggttccca agactaaagt gtagaggaca ggtaagatga cactgtcatg atcatcattc | 1560 |
| gtcctgtgcc ctgtggacat caacccacag atgtgacatc aacccatctg atattgagcc | 1620 |
| cagtgggtgg ggagatccta acccagctgc tgctgttgag gacttgggtg gtgtctggcc | 1680 |
| agtgggaggg gaggtcaggc gagttttcag cagatgaccc cgtgctcttc ggaagcccgg | 1740 |
| aggtgccaca ctgtacaagt gtgatgcctg ggatcctgtg ctcccctgat gcctgggaat | 1800 |
| ggggtgaagg aacagcctag gcttgggttc tctcctgggt tgtttcggga cttggcccca | 1860 |
| gctcaggaag ggtttgtgga ggagccaagg agggccttgt tcctgtggga tgtcttttgcc | 1920 |
| ttgggcacaa ggacagcctc ttgctgctgc tctgcccacc gcccacccct tggcggcctc | 1980 |
| tgggagtctg ggctgctctc cctctggacc taaccagttg cccaatggct ggacctgctt | 2040 |
| aagctccctc ttacaactgg accaggcagc caggggaggc actgagaggc cgagcttctg | 2100 |
| agctggtgcc tgtggatgct cgacggtccc gcagctccca caatgggatg ccaagcaga | 2160 |
| ccctgagatc cacagccccc ctttagtgaa acaggaggga ggtcgctggg cacagggagc | 2220 |
| cgggaacgcc tgccctcccc gccatcgacg gctcccgagg cctgaacctt cgctccagcc | 2280 |
| ccagcacaag ccggccaggg cgcagggcca agtgttgccc gccattcccc gggtacccca | 2340 |
| tgacctccca gctggggctg gctcggactg aggagtcgtc cctgcccgtc accctctggg | 2400 |
| gtctccagtg ctgcggagct cagctggctt ttgcagcggt aggggctggg aggagaagct | 2460 |
| gcagggagac cgcaggcgtg ggacgttgtg ggggtcagg cttgctctgg ggctgggacc | 2520 |
| ccgggggag cagtggggtt gacgccacag cgatgacttg gccacgggt ctgggggctc | 2580 |
| tcccgcgggg cgattgggct ctgtctttcg ggattagggt ctctcccaca gggtttgggg | 2640 |
| ttctctctgc agatttgggg gagtctctcc cgcgggatga ggggggctc tccgccgcac | 2700 |
| ccgcctatga tggcccagag gacccgagct cgggtcactc ccgtcgccct cggggctcgg | 2760 |
| cgagggtgca ggaggcgggc gctgagccgg tgacgcgact ccggcggct cccgggtgcg | 2820 |
| ccgcatatat agcagcggcg gcggtggcgg cggccacacc gggcggcgga cacgtggagg | 2880 |
| gacccggccc gcgccttctg cccctgctgc cggccgcgcc atgcggtgag cgccccaggc | 2940 |
| cgccagagcc cacccgaccc ggcccgacgc ccggacctgc cgcccagacc cgccaccgca | 3000 |

<210> SEQ ID NO 8
<211> LENGTH: 3002
<212> TYPE: DNA
<213> ORGANISM: Homo sapiens

<400> SEQUENCE: 8

| | |
|---|---|
| aggtataagg tgcaaaatac actggatagg attggcagta atcagatatt acagaagaaa | 60 |
| acattagtga actcacagac atagcaatag agactatcca aaataaaata tgaaggaaaa | 120 |
| aatgagcaaa acagaagcaa aaacagatca ccaacaaact gtgggccaat atacactcac | 180 |
| cgtctgactc agccattctg gttttaagta ttttccaaga gaattaaagg ctttatgtcc | 240 |
| atacaaagac ttgcatatga atgtcaaggc agctttattc gtaaaagttt caagtgaaaa | 300 |
| taaccaaaaa ttcatgagca gtagaattga ttaaaaattt tgaagtatat catataatga | 360 |
| aatactgccc agcaataaaa aagaataaac tattgctaca tttaacaatg tgagtggatt | 420 |

```
caaaaataat gatgctaagt gaaagaagtc agacaaagag tacctaccgt ggaactatat    480
ttatgtgcaa ttctagaaaa cgcaaacaaa tctctagtga tagcagatca atggaggagg    540
gggtgaggaa gaggcaaaag gaaggaatta caaaggtaca tgtggaaatt tggggaagtg    600
atgtataatc ttcattttct tggtttcagt gatggcttcc tgagcatata acacacatgc    660
atatgtgtaa gaatatatcc aattgaatat tttacacatt tgtagctttg tatatattca    720
gcagtatcta ttcattcctt ctgcttcttt accttaggtt tagtcatgaa accactgggt    780
ttcatgtggt ccaggttcta tctgaatcaa gctatgaacc tgctatcagt aagacctcct    840
aattgcaaac cacatggacc tttaccggtt atttgacttc tctcggtcat taccttctct    900
agtctccact gattcacctc cttttgaatc tcaacaagct caacagtatc tcaatgttat    960
cttaacaaag ctgttagaaa taaacaactt gactttgaaa caaggagag aaatggctca   1020 gcagctagga gaagatgcag ggttgagttg ccaacagttg gttttgtttg tattttggcc   1080
aggggatgtg gcttggactg gagagaaagg agataaggat gtaagcacat gtagggcata   1140 tcaccccta tttttattc tctgaatcct taaccctcag aataagttct tattcttgag    1200
aatcaatgac attatcttaa gctaaattaa tcaagcctcc acagtgttct tctctcaata   1260
gtggtgtggg ccttcctaga agtaatttt cccaaattca gtgatacatt ttaagttcag   1320
attttaattg atatgaatct gtgatacact ctaaaataag attattttat tgaaaagtgg   1380
actgtaactt tcccttatc taggaagagc tctaagttag aagatgtttt gcacttttac    1440
cgaaggctgt gtcttgtaag cacccccgag caactctgag agccttgatt tttgtgtcct   1500
cagcatatgt ttgtgtaata cagaaagaga agcagttgcc aagtgaaagg gatgttggtc   1560
tccaaaatta tagtttgatc ccacaaacac acaaacacat acatgcaaag gattgtttgc   1620
ttcacggttt ttgatattta attcaatgct gttggaacag cacaaaaact aagtgtcagt   1680
ttaacagaat cacttgtcct tttagcatta aaataacatg gaacttaatg ctttaatttc    1740
ccaacatgcc tttttattta gaaagattca gacttatatt tcatttagaa ataaaatgcc   1800 atttattta gaaagataca ggagcattca ttcacggaac tttcagatct cagtccactg     1860
cataaaatct tgatcctgta ataatagttt ctgtatcttg catattcatt caacaggttt    1920
aacgcgatga gcaaattaat gttcatcgtt tttaacatgt ttcatcttaa tcagaaccca   1980
cattctcaac gttaattgaa cgtacatagg actatacaag ggttagtaaa taagacagaa   2040
actgttgttc atttaaccac cgtcactttg gaccaaaaaa gaaaaatat atatttttaa    2100 aattgagctt aaaagagtct ctagaagctg gaagcgtggc tcttttttcag caaactgggg   2160 gaataggttt accgtgttcc ccctctgggg aattttgagt cgccacactc atgtctcgac    2220
cgagcctggc tcgctgcgtc tgagcgagta cttgaggaag gctgatctag aaaaaccagc   2280
tgagagaagg ggcagaagcc cctgaaacca cgggcggggg tgggtgggg agcgcagctt    2340 tgggaccctc tagccggaga cttccggcag ctgcctccga cttgttctaa gtacaggaaa   2400
aatctgtgcg cccagttgcc tcactccaac agcgcgcagt tgtgcccggc gaggatgccg   2460
cgctagtcgt ggagatgccc caccacaaag aggattcagg tgcttcctac tccggcaccc   2520
agtgggttgg tagtcctgtt ggcaggagac aagaatcgtc tgggctgctc ctatctctgg    2580
caggactaga cggggcgtga aggaaagaag gaaagaagga aagcagggat cgggcactgc   2640
ccgagggcag atacttgggc tttggtgttg tccagcgcgc tcggagtgcg ctgcctcgct    2700
cacgcggtcc caggccccgc ttcttcaggc agtgcctggg gcgggagggt tggggtgtgg   2760
```

-continued

| | |
|---|---:|
| gtggctccct aagtcgacac tcgtgcggct gcggttccag ccccctcccc ccgccactca | 2820 |
| ggggcgggaa gtggcgggtg ggagtcaccc aagcgtgact gcccgaggcc cctcctgccg | 2880 |
| cggcgaggaa gctccataaa agccctgtcg cgacccgctc tctgcacccc atccgctggc | 2940 |
| tctcacccct cggagacgct cgcccgacag catagtactt gccgcccagc cacgcccgcg | 3000 |
| cg | 3002 |

<210> SEQ ID NO 9
<211> LENGTH: 3000
<212> TYPE: DNA
<213> ORGANISM: Homo sapiens

<400> SEQUENCE: 9

| | |
|---|---:|
| cctgcctgtg tgccctcttg taaggcactg aaggtctcag gacctcagtt tcctcctctg | 60 |
| tgaggtggga atagcatgcc ctgaagtgtt ggatgagaaa gtgttttgtg agcaacagag | 120 |
| gactgggtaa ggattcctag tgagtttggt tggtctgggc aatagcgtcc ccaatacaac | 180 |
| cacaaaacac tttacccttc cagctttgag acttgggaga gatgccctgg ggttgatta | 240 |
| cagaaggctc aggttgggaa agtttgaagt gcttcatgct aaaccaacct ttaagctata | 300 |
| actggccatg gagggcttaa gggagaattt atgtcccttt ttgtcctggc ttctctgata | 360 |
| agtggttctc agactcataa ctctccagga gttataaaac aacaaaagca aaaccccttaa | 420 |
| gtcatctcat ttcagcttc agctcttcag cagggtatga gggaagcaac tgtttactat | 480 |
| tcataagtag atacttaaac agatagacat catgaggttt tttgtttgtt tgttttttggt | 540 |
| gagaagcagt tgaggaggga agaagaaaga aagaggaga gaaagagag ggagagatgt | 600 |
| cttgaggcag agactgggat aggcactggc taagcagggt gagaaggcag ggaaagagcc | 660 |
| gggctgaccc aaaccaaagt cagaaaatga ttgagaagag caagaaaaac aaggaatga | 720 |
| ggatacagag tcaagagagg agacaaaaga aggattgagt gaggaaaatt ctgaaacata | 780 |
| aatttgcaga aaggttaagg aaaaggagga ataagaagga ggagaaagtg tagagggaga | 840 |
| gcacaaggat gtggaaggag gggagcaagc gtctgggaa ggagacagaa gagatcctag | 900 |
| agcacagggg aagatgggga gctgctatt gttcttcggc tggctcctgc tttggaaaaa | 960 |
| tcctcgtttc ctactcagtg ggtatgccaa agaccacatc ctgggtacag agatatgag | 1020 |
| atcatttgga ggtacctaga gacagtcaca gtgatagaaac taaactctga gtccttagag | 1080 |
| gccagagaga gttgcaagat ttagagaata taacatgtat ttcctaggac tgggttccac | 1140 |
| agctccagat tcattgatct cttagactac tccaacacat gtgaatgact ttttaatgcc | 1200 |
| ccactttgtg cttagtcttg gctggccttg tcaagacctg gaaactttaa cacttcttgc | 1260 |
| tgtgcatttc cgctttgcct tggattacaa gcacaaaaag aaatagtgac aattattcaa | 1320 |
| gccattcagg atacttccca aacccttctg cctctcaaca ctgtggttcg ggtctaagta | 1380 |
| ctgagaatat tttaatacct aatatgagct tcgcatggtt tccagagatg cagcatatct | 1440 |
| ttttagctaa tattggcttt tttgaagctc ataagataac agctcttaaa gatcctgtag | 1500 |
| ggatcatctc gtccatgcta ggaaattagc tggtccttcc tcagtaagga actatttaga | 1560 |
| taaaagcagt cagaactctg gcctgaacag taaacattta accagagttc aatcagaatt | 1620 |
| caaggacagg ttttcttaaa ctttctttgt ttctaggaga tcaggcagag ctgaatttaa | 1680 |
| ccaagaatct tttgatcctt tccacatata gatatacaat agtggtcaca tatgttctgg | 1740 |
| gagttcctag accttatatg tctaaactgg ggcttcctga cataaaacta tgcttaccgg | 1800 |
| ccaggaatct gttagaaaac tcagagctca gtagaaggaa cactggcttt ggaatgtgga | 1860 |

-continued

```
ggtctggttt tgctcaaagt gtgcagtatg tgaaggagaa caatttactg accattactc    1920
tgccttactg attcaaattc tgaggtttat tgaataattt cttagattgc cttccagctc    1980
taaatttctc agcaccaaaa tgaagtccat ttcaatctct ctctctctct ttccctcccg    2040
tacatataca cacactcata catatatatg gtcacaatag aaaggcaggt agatcagaag    2100
tctcagttgc tgagaaagag ggagggaggg tgagccagag gtaccttctc ccccattgta    2160
gagaaaagtg aagttctttt agagccccgt tacatcttca aggcttttta tgagataatg    2220
gaggaaataa agagggctca gtccttctac tgtccatatt tcattctcaa atctgttatt    2280
agaggaatga ttctgatctc cacctaccat acacatgccc tgttgcttgt tgggccttcc    2340
taaaatgtta gagtatgatg acagatggag ttgtctgggt acatttgtgt gcatttaagg    2400
gtgatagtgt atttgctctt taagagctga gtgtttgagc ctctgtttgt gtgtaattga    2460
gtgtgcatgt gtgggagtga aattgtggaa tgtgtatgct catagcactg agtgaaaata    2520
aaagattgta taaatcgtgg ggcatgtgga attgtgtgtg cctgtgcgtg tgcagtattt    2580
tttttttttt aagtaagcca ctttagatct tgtcacctcc cctgtcttct gtgattgatt    2640
ttgcgaggct aatggtgcgt aaaagggctg gtgagatctg ggggcgcctc ctagcctgac    2700
gtcagagaga gagtttaaaa cagagggaga cggttgagag cacacaagcc gctttaggag    2760
cgaggttcgg agccatcgct gctgcctgct gatccgcgcc tagagtttga ccagccactc    2820
tccagctcgg ctttcgcggc gccgagatgc tgtcctgccg cctccagtgc gcgctggctg    2880
cgctgtccat cgtcctggcc ctgggctgtg tcaccggcgc tccctcggac cccagactcc    2940
gtcagtttct gcagaagtcc ctggctgctg ccgcggggaa gcaggtaagg agactccctc    3000
```

<210> SEQ ID NO 10
<211> LENGTH: 4050
<212> TYPE: DNA
<213> ORGANISM: Homo sapiens

<400> SEQUENCE: 10

```
gcctgaagcc aaattcagcc tttccctcca gaagcttccc ttttgacctt gctcatagcc     60
agtgggaaga ggctttgtct ccacactctg tggtcccatt gaatctacct gttctcctaa    120
attctatcaa gtcactgttg cccaccctcat gttagagccc cacagaaaat ccagtctttt    180
ggaaagatga aaaggtgac tctattgact gaaatagaaa cagaagtgac aaccctgtcc    240
caacacataa gaaagatgc tgagtcatac tccaattcta ttcagaaatt ggactccctg    300
gggacagaga ttttatatta catttgttcc atgtcatgtt cacatgtcag aggcatctca    360
tgttcaccag taaataaaaa gctaagcaaa tgtctgaata cgtttggtgt ttggtgttcc    420
ggctctgccg gaaggtgaca cataatggta gggatgaaaa gagtcattat agttaattag    480
ttgaaatgac atagaaatta tggaattagc tttttttttt ttttttttt ttttgagagg    540 gagtcttgct ctgtcgcaca ggctggagtg cagtggcacg atctcggctc actgcaagct    600
ctgcctcctg ggttcacgcc attctcctgc ctcagcctcc caagtagctg ggactacagg    660
tgcccatcac cacgcttggt taattttttg tattttagt acagacgggg tttcactgtg    720
ttagccagga tggtctcgat ctcctgacct catgatccac cgcctcggc ctcccaaagt    780 gctgggatta catgcgtgag ccaccgcacc tggcccgaat tagcttttta aagcatcctt    840
gatccccgaa atattagat gtcaaacctc aacgcacctt tactcctaaa ataccattag    900
aagaatctat agtgctgtgg aacacataat gctaacacca gctatgagaa atcaatatct    960
```

```
atcagcatcc ccttaactta cattggaaga aacactaacc acccaattag atttaagtag    1020
tgaggctgac tcagcacaca ggggtgtcta agaaataaa gggaaacaac atccagaagt    1080
tctctttgtg aaccaaaaat atgccttta gaccaaactt cttagcaaga atacaagatc    1140
catcacaatc tcacccaaac ctgcttctag ctgcatttca cgctgttctt tttccacccc    1200
tgtcttccaa tctgggtgac cctctggatt tatagatgtc cctctgctca atgtcatgct    1260 ctttcctta tgccttgatc ctaggcacat atgattttct tcattcaaaa gaccttgtca    1320
acacttaacc tttaaagata tcgtctttc tggagaaaag gtagttgctt cactccagag    1380
aggggttggg gtctaaagag ctgtgagagt acacatcttc atgctatttt tctcagcctc    1440
ttgctcagtg cctggcaact ggtagatgtt tgataaattt ttttcaagta aataaaggag    1500
ttgctaattc actcgtatga gtgcttgcct attgatctga ggtcaatcac tcttctgaac    1560
tcattgggct tttccaaagt aagcctttcc ccctcaatct aataatgata ataataataa    1620
gtgctaatat taattgagca cttactatgt gccaaatact atgcaatctt aacatgaatc    1680
atttcatcta acttcataag ttctcctcac cctgcagatg aggaacctga agcttaagac    1740
actaagtaac ttgccataat tataaatgag ggagccagga ttgaagcaga gcctgtgtac    1800
tgtatcatta agctatattg ctggcaacta atcaacacca ctgggctcat ggctattggc    1860
tggttactgg tgctactgat ctctgccgag aagctcttcc acctctagcc atgcagcatc    1920
agtctccctc ctgctggcag agagggcgc tgagcctttc atatttacat agaaagcatg    1980
gcagcagcct cagtgttgga acctgccact ggaaatgtcc ataacaacac agttggggc    2040 tttctttgtg ggccctggca tggtaagtgc aagtttgtt attccttatg ggttctgaaa    2100
aatgagactt cacctgttag tgactggctt cacgtcatgt acctggagga gctggcttca    2160
catacgtcat aaagatgcac tctaataatg tatttagaag ttgttggcta aaggtctaag    2220
cctgattcta atagcacttc ctcaattaag cttttctag cactccttca acgataactt    2280
acttctttta ccacccactc aattcctcag tattgtatct atcacgcttt tatagttctt    2340 tatttccac acagggctat aaagaggata tttgctataa acatggcaa acattcaatt    2400 aaaatgcaa atagctgcat caaaatgccg attcataaaa ttttagatc agatgagaaa    2460 agacccattt ttctggaaaa gactattgat cattgagagt taagaataca gctggttccc    2520
aatttaattt ctccctggta aacagaatag gaatggcttg gcaaatctac aggaaagaac    2580
atgtgtgcat tgtgcttctg gcttttccag atgtcagttg ctgaaggttt aaggtgtgag    2640
tctgtgcatg tgtttctgag gatcagtccc tgttcaaaga ggcagtggga agactgagtg    2700
ggataactca cacatggaca ccctgtgcat cagtgtgcgt ttaattcaaa gacagacctc    2760
atttgatagc aatattgaca tgtcattcta atgaattaga aaaaatgaga aaatgggatg    2820
taaatcccca tctggattca tggggatagt atcagaaaga ttttcagtgc ctttgcagaa    2880
tgctagcaac attttattaaa tacctaccct aggtgctatg tgcttacatg agaagccaaa    2940
ggtatctgtt aagctaggta ggaactgcag tcggctggtt gcttctcatc tggagaaagc    3000
ctacacatgc tgctgccagc ggccagctga tctctaggtg tttaggccta agagaccaac    3060
cagctccaaa tcacttaaag cctaaacgtt ccctgtctct actaaaaata caaacattag    3120
ccacgcatgg tggcgggcgc ctgtaatccc agctacttgg gaggctgagg gaggagaatc    3180
gcttgaacct gggaggtgga ggttgcagtg agcagagatt gcccattgc actctagtct    3240 gggcgacaga gtgagacaca cagacacaca cacacacaca cacacacaca cacacacaca    3300
cacacacaca cacacacacg cctaaacatt caaggccagg atgcttgaca gatgttgatt    3360
```

```
cataaaaatg acaaaaagca caaaatccaa aatctcgtat aagctcagtg gctgtggcag    3420
cgaggttgaa gagcaaaggc aggccgggca cctggctgat gatgtgtgga cccgttgcac    3480
agcagggccc cgcagtgcgg tgtgggtgtg ggtgggccag tctctgccgc tcaccctatt    3540
ccagggacac agtctgcttg gctcttctgg actgagccat cctcatcacc gagatcctcc    3600
ctgaattcag cccacgacag ccaccccggc cgttttcctt gttctgtgtg gggagggagg    3660
cagcgcggtg gttatcaacc tcaccctgca gaggaggcac ctgaggccca gagacgagga    3720
gggatgggtc taacccagaa ccacagatgg ctctgagccg ggggcctgtc caccctccca    3780
ggccgacgtc agtggccgca ggactgcctg ggccctgcta ggcctgctca cctctgaggc    3840
ctctggggtg agaggttcag tcctggaaac acttcagttc taggggctg ggggcagcag    3900 caagttggag ttttggggta ccctgcttca cagggccctt ggcaaggagg caggtgggg    3960 tctaaggaca agcagtcctt actttgggag tcaaccccgg cgtggtggct gctgcaggtt    4020
gcacactggg ccacagagga tccagcaagg                                      4050
```

<210> SEQ ID NO 11
<211> LENGTH: 2999
<212> TYPE: DNA
<213> ORGANISM: Homo sapiens

<400> SEQUENCE: 11

```
cccgcccagc ctcgcggggc acgccgggag gcggagttct cggtcgtgtc ccgagagtgg      60
ctggtccgca ggctcggact accagtccca gaatgcactg cgcccgcagc ccggggcggg     120
ccgtggttgc ccctggcaac agagagggct cccgggagcg gggactggga agcgctcccg     180
agccggggag gcgcagagcc cgaccagaga gaggcgggga cgcgggtaga gcgaccaaga     240
ggtgtggagg ccggaagaga ctgaccgcgc cggcccttgg agagacccct ttcctgagag     300
ggggcgcaca gagaggatgc cgaagccagc gagatctaga gagagggaga cagggattga     360
atcacagaga cacttagagg gagggagaga cctcaaagac agagagattc acagggccag     420
agagacacgt agagtgggtc agagaagagg acagaggaca gagacataga aaagacagga     480
gggagagaga ctgaatcaca gagacacagg gagagaggga gagacctcag agatggagag     540
agactcacag ggccagatag acacatggag tgggtcagag aaggggacag agagagagac     600
acagaaaagg gaagagggag agagactgaa tcacagagac acagagggg aagtctctat     660 ctagagaccc tcgacagaga ttcctagagc cagagacaga gattcagaga gccagagaca     720
cagagagatt catagagaca tatagagaga ttcagagagc ctgaatcaca gagattcaca     780
gagccaacga gacaaacaga gagattcata gagccagaga cacagattcg gagagtcaga     840
gagacataga aagattcata gagccagaga cacagagatt cagagagtca gagagacata     900
gagagacatt catagagcca gagacacaga gagattcata gacatataga gagattcaga     960
gagcctgaat cacagagatt cacagagcca aagacaaaa cagagagatt catagagcca    1020
gagacacaga gggattcgga gagtcagaga gacatagaaa gagattcata gagccagaga    1080
cacagagatt catagagaca tagagattca tagagccaga gacacagaga ttcagagagt    1140
cagagagaca tagaaagaca ttcatagagc cagagacaca gagagattca gagtcagaga    1200
aacatagaga ttcatagagc cagagacaca gagagattca gagtcagaga gacatagaga    1260
gacattcata gagccggaga cacagagaga ttcagagtca gagagacata gatttataga    1320
gccagagaca cagattcagg gagtcagaga gacatagaga gacattcata gagccggaga    1380
```

-continued

| | |
|---|---|
| cacagattca gagtcagaga gacatagaca ttcatagagc cagagacaca gattcagaga | 1440 |
| gtcagagaga tgaatagatt cagagagcca gagacacagg gagagtgaat cacagacaca | 1500 |
| gagggacggg gagatcccca gaaacagaaa gagattcata gagccagaga gacaaataga | 1560 |
| gattgggtca gagagaaagg gacagagaca gagacagaga agagaagagg gagagagatt | 1620 |
| gggtcagaga gaaagggaca gagacagaga agagaagagg gagagagaga ctgagtcata | 1680 |
| gacaggagag agacccccct agcatcagag agagagagag agatcaacag agccagagag | 1740 |
| ggacaagtac agagaaacag atggaaccag agagatatag gaagagacaa acaaaaacag | 1800 |
| agacggagtt gcagaaccgg aggaaggag agagacagag acaaaggcat ttataaagac | 1860 |
| gggtggaggt gaggagagag agggagagac aggggcaagc atttagagag tgactcccag | 1920 |
| agaggaagac agagacggac tcccaaagag atcaagttgc agagggaggg ggagacagag | 1980 |
| tcacagcctg agagagaata gagattcaca gagccagaga gacaaagaca gggaaagaaa | 2040 |
| caaactcagg gagacagagg cggaagaatt tatcagacgt agagggagag acagagggag | 2100 |
| actgattcac agtgaggcag accaagaccc cgagaagaac cacgacacca gacccagag | 2160 |
| atggcgacag atacagatgg agacacacag cagaggaaat agagaaatag aaagaaatag | 2220 |
| aaacagcatt tctcggagac agggaaaaga aaacagatcc actgagaggc agaaacagag | 2280 |
| acacatcgag aaagctcgct ccaggaatag agggagaggg acagaggtca caagaaagac | 2340 |
| acacgcaggc agagagctac acaaataatg gagaggccag ggggaggaaat aaagactcag | 2400 |
| ccggcatcgg agaaagtgag aaccttagcg ccctgcctgt ccactgctgg acccctagcg | 2460 |
| tggagcataa agtttgttga aggaaggaga ggggcagggt cagacacagg gaccccaggg | 2520 |
| cgcccacagg acacacgagg caccctagtg ggggaggaac gcggggcagg atgacagatt | 2580 |
| gcagggtggt gggggggagc caggctcaga ggatgcccct ccctccagcc agcccccgga | 2640 |
| gtgggtgtgt gcacgtgtgg ggggcgggga gggaggacat ttgtcccgtg tctccgggag | 2700 |
| gggagcgcct ttaagccgaa accccgcccct ctcggtcgtc ctggcaacgc ctcccccaac | 2760 |
| ccggggctcc cacatttcag caggtgccgg agctggagct cccaccgccg ccgcccgtgc | 2820 |
| ctccggctgc cggcgcccct gccttttggct cttcctcccc actcgcccgc tccccctggc | 2880 |
| ggagccggcg cgcccggggt gccgctccct gcctggcgcg ctccgcacct ggaggtgcct | 2940 |
| tgcccctctc ctgcccacct cggaatttcc ctgtggctcc tttgatcctt cgagtctcc | 2999 |

<210> SEQ ID NO 12
<211> LENGTH: 3000
<212> TYPE: DNA
<213> ORGANISM: Homo sapiens

<400> SEQUENCE: 12

| | |
|---|---|
| cgctcatgag atcactgtcg agatacttcc cttcatttcc ttctctgtga ccttgaaggg | 60 |
| tctgggctac atcatctcca tgtctccatc ccattccgat attcttgaag atcaagaccc | 120 |
| tgggtggccc attaaagggg aatggaaggg aggtgggtag attttgatac gtctttgcaa | 180 |
| agaggttgac attcctgttg ttgcaggctt ggcggaagta cgacacagac aggagtggct | 240 |
| acatcgaagc caatgagctc aaggtaggat gggccttggg gagggtgtga ggccagagtg | 300 |
| gcggtgggct taaggtgcct gaggagggag gagatgttgg atgaggggca tgagtttgcg | 360 |
| ggctgcttag gaatactcag acctggcact gaattgttgg acttgtttag agaagtcagg | 420 |
| ggaaatcagt aacatagagc tgccaggctg tagatttcaa cgaaacccag ctcttctgca | 480 |
| cctccatgct cgggacagga gtcctccagg caattccaga agattggcct ctggctccta | 540 |

```
ggtccacctc caaattcctc tggctatcac ccagtgattc cccaggcact gcttagctcc    600
gtatactggt ctcccaggag gcagagccaa tctctagcgc ctattctgtg aggcagggtt    660
gcaccaccag ctagtacagc cttaaaagtc actccccaag agttaggaat tatgagggcc    720
ctgagtcata gaactggtag acctgaaaaa cacacacaca cacattgaga gactgtctga    780
atgagcaagt aaggaaatga atgagggacc gaatgcacga gtcaggagta ctaaagaggc    840
cttttgtgtt gcagggattc ctgtcagacc tgctgaagaa ggcgaaccgg ccgtacgatg    900
agcccaagct ccaggaatac acccaaacca tagtgagtga acagaagtgt ccctctcccc    960
cagggtgcag gacttgtgcc ccaagccact tgggctctgg tgtgcagggt ccttgtttg    1020
ctgattcttc aggcccaagg gaagtgattc acagtggcag ctggcaaaaa gggatgctac   1080
ttcgtggctt cacataccct ttgaggtcct gggtgtgagc tgactcgtgg gccaatgtga   1140
ttgtctgtct ccatggcaac ctctgcagct ctaggagagg atgatcttgg agagagtggg   1200
cctttagtgc cggcctgctg tgcctcagct gcccctgtcc ctgaggaggg gagagaggag   1260
cagtgaacga gtccctgtgg tccacccagg gaccccccgt gactgattta gcccatgttg   1320
gttcttggcc cctacggacc tcagaggaag catgagcacg tgtcacccgt cctccttccc   1380
atcctctcca gtaaaagggg atgtcaggtc agagaaattc acagcaaata acccaggcac   1440
cttcctgtcc ccaacagcta cggatgtttg acttgaacgg ggatggcaaa ttgggcctct   1500
cagagatgtc ccggtaagca cctcaccccc ggggtcactg atactggctc ccacaggtca   1560
ttcctgtgtt atccgtctct gagatccatt ggtgggaaag tgacaggtgc gggtgtcaag   1620
aagctcaaga caaagcaaga tagaattgtg accgtcaaca cctcaccttg tctgtctccc   1680
tcgtttttga acttcccact gattcattat gtgtgaagtg ctcagaaatc atttctgtaa   1740
ctgcaggcac cgcctctgcc ttcccctctc ccgcttgccc ttgcctgtgc agtctcctca   1800
tctctgctct aacattttct ccccagactc ctgcctgtcc aggaaaactt cctgcttaaa   1860
tttcaggtaa aactttgctt tccttccttc ccccttccct catccctctg agcctggccc   1920
tgcaccctcc ttcccccaac gcaccacaca caacacacta cacacaccca cacacaccac   1980
acacacacaa aacacaccac acacacaaca cacagatc acacacacaa aacacacaca    2040
gaccacacac accacataca caacacacgc agaccacaca cactacatat cacacgcaca   2100
caccccacat acacagagac atcacacaca ccacacagac cacacaccac acacacaaca   2160
cacacatcac acatgcacac accacacaca taaacacaca cacacaaacg cacacccaca   2220
cacacaccac tgcgcttctg cttctgtctt taatacccctg gttcttgcag ggcatgaagc   2280
tgacctcaga ggagtttaac gcgatcttca cattttacga caaggtaaga gagggagttg   2340
gcatggcagg gaaaatcaga agcccatcag cccgtccaga agggctcagc ttcatccctg   2400
ggaagagaca gctttccagg ggtggcctgg gccgtgtggt ttcttcctgc cgcatcttct   2460
gctgtatgag aaggcaaatg tcattctcca ccggtggcct atggagccca aggggttggt   2520
ttctgcagag tgcagccgag aatcgttggg ggaggactat gcttagaact agggtgtgac   2580
cacgctgtcg ggagccaaag ggaagagaca ctcagaactg ccctggtgcc agatcacaat   2640
tctgcccagg gccaagtctt tctctgggaa gttggaagtt agatgatctc catacccacc   2700
cctccctggg ctgtcccctg cccacatgac tccggtggtt ttcttcataa ccagtgttgg   2760
aggtaaactt taaatagccc ccggactcag ggagttaacc aaatgcttct tgaatctcac   2820
ttaaattttc aacgcacatg aaaagcacca caatgaaagg ctacccaaag cttgcaccca   2880
```

| | |
|---|---:|
| ctgccacctt cctgccatga ctggttaagg cagaagggac acattatttt gtcattacac | 2940 |
| gatctgaaca ccccctttg cacagagtaa tggagaggct agactcttag acatccctgg | 3000 |

<210> SEQ ID NO 13
<211> LENGTH: 2441
<212> TYPE: DNA
<213> ORGANISM: Mus musculus

<400> SEQUENCE: 13

| | |
|---|---:|
| gaattcccag ggaagatccc agggaagatg aagaaaccat ggctacaata ttttattaaa | 60 |
| taaagagtcc attgtgccac cttcttccag cttctaactg tccttgacac ctttggcttc | 120 |
| tcctggtggc ttttctactc tggcctttga ccctgcctgt ggtcaggtgc tggaccctc | 180 |
| tcccgttcct tcctctggct gtcacacctg ggaatctggg cagagatgcc ttttctcttc | 240 |
| cctcgcttcc cacctttga gtctcttcct acagcttcca ggtgggaagc caccatctac | 300 |
| agaaagagtc ttgggttgta cctccagtgt ccctctgtcc aggacttgag atcacaacct | 360 |
| tctctagctg tccacccata acctggattc atccccacg cccgccaga cacacaccag | 420 |
| ttggtgtgtt ttcttctgaa ctccccctgt ggccaataca ctcccaccca cccttgtctc | 480 |
| tcagcccaga acttcacagt cagccccaga cacggagtac ctttgggttt cttgaagagc | 540 |
| aagatgctgc ttccatgcct ggaagtttct gcttatgtct actgttctag ctattcggat | 600 |
| gttctattgt aggcacttag gactcgtata gtgtctgcta catttcatga tagtgaataa | 660 |
| atttcacaaa agcatattag gcttcctata aatctgtcct cattcctcaa tggccctccc | 720 |
| atctcctgtc ttcctaacct gtcctggtct cccgtgtctg ccctagggac acctccatgt | 780 |
| caccaccaga ctcagtggaa atccttactc cgcccttggc tattagtgca gatctgaact | 840 |
| cagttccttg tacttgcagg caagcacttc actggctgag ccgcctccca gttccagctc | 900 |
| caggcccccg gctcccaaag gtgtttattt gtgtgggtat ttattttgtc cagtcttggt | 960 |
| cacaccgcat cctcagggc tgggcacagt tcataaatct tgaggcaagc gatggaggga | 1020 |
| aggaggcagc taagcgtcca tatctcagcc accgacccag ggaagtcagc gcctgtggat | 1080 |
| tctgaccata tcgaacagcc ttgtgcccag ctgctttatc cacaattccg gacatgctcg | 1140 |
| atctgtcaca gatacattcc cacaacctga gctgtcttgt gcgggaaatc accccacagc | 1200 |
| atttaatctg ttgctgttta aaacatgttg cctctaggtt gcagacaccg ctagagccac | 1260 |
| aaccatgaac ctaaactctt ggcatcactt gctgtttctc atagtccccc tcagccggaa | 1320 |
| gtccccaaac tgtgtgcctt ttctatttag aaagagtttc taacccttc tccattcacc | 1380 |
| ctagcttgac agggttgagg gcatggttgc cctggctggt ggtgacccca agttacaagc | 1440 |
| tagcagcaag gaggttgctg tggggcttcc tcagtatgtg ttctgtggaa tggggttaga | 1500 |
| gggattcagc aaattctagc accctgggca tagataatca ctttgttatg tgagaactgg | 1560 |
| gggttgcagg attgtgcgca ctacagcaga gagagccccc tctctccttc ttgcttggta | 1620 |
| agagtctttt tctcagccaa gatcctcatc acccagcgaa atcccataac tttagaggga | 1680 |
| ctagactgga aagggtgatc tgagctcttg ggaaggtgcg agcccagccc gcatggctca | 1740 |
| gccagccaga gcttgggagt gcctgagaca ctctctggcg ccacttcacg accaaaagca | 1800 |
| tcagtagatg ataggcccct gggaagtcgt cgtggaaaga aattacaaat cttttttcca | 1860 |
| gaggcttttc gcagaaaggc aggagctgca cccgatctta caattgtgta agaatagaat | 1920 |
| ccaggatgcc aactgcaatt gagttctgaa aaattgggag cccgatttcc ctctcttact | 1980 |
| tgtgagagcc cactcaggtc tgaggtggtc ccagagaaca caccaggatt acatctgctg | 2040 |

```
acacccagcc tgtgagggtc ccccagtttc cttgaaggat ttgatcccca aagctcactg    2100
aacttggtca gcttctccat tgcagataaa ctcctgtttt tcaccgagag tggaggtggc    2160
accctccctg aggtggactc tgcacaggcg ccgaacaggt gggaaggaag ctctttagat    2220
aaagagtaag acccatgcaa agtgccccc tgggagggggc tatcctcatt cactgggacg    2280
cttcccttct ctccggaggg ccacatcaat cggtggtccc tccagtggct gcctctgagc    2340
acgtgtcctg ctggactgcg tcagcactgg gtaaacagat gactggctgc gaaccgggag    2400
gagctattta agagcagtca ccctcccgcc tgccctcacc t                         2441

<210> SEQ ID NO 14
<211> LENGTH: 1544
<212> TYPE: DNA
<213> ORGANISM: Mus musculus

<400> SEQUENCE: 14
ccatggcgat ggaaagctga ccagtgctcc ctctgatcaa ggaatccttt ccaagctcac       60
cagagagcac aagcataaag gacaggaaca cagactcatg taatcccag aacaatccaa      120 gatgtcaata cccacacacc cattttacag actcggaaag ccaaggcaca gacaggctgt      180
gtaagccaaa caacgttgtg gaggttttgt tgttgtttgt ttaggaacta gacccgagga      240
gtttgattct attgcaactg ttctttagga ctgagccttc ttgccttctc gaaggcaaga      300
ctcaggctgg gggactctag cttagtaatt tctcagccct ggcagcaagg aatgctgggt      360
tacagaagcc ccaacagtta gcctattttg ctgcgtcttt cccagtctgt tcttgtaaac      420
aacctcaaac tgtgtgcctg ggcaacacac cagcagtttt gaaacttggg ctccatgttg      480 cccttttgagg ttagctccga gctacctcaa cctgacccca ggaaacagcc tgctcttctc      540 cgctccccc cctccccccc accccacccc gggttctcct ctcccctagc gacctgcttt      600
agattctcac ctccttctct tttgctctcc cttcgaaggc agctcagcta acactcatta      660
gcacatgtta atgagcagca attcaagtct ctgtccttct ttttaggggc agggtgcttg      720
ctgttgctct gaaggtaagg tgtccaagaa gcaagcacac actgcagacc tttagagtag      780
ggaggatatg ggacggaggc tggctctctg attgaggaga ccccacggtg tgctgtgctt      840
gctgtctgtt ttcttttaaca gaagttcagc acatctttgg gtcagagttt accgccatct      900 acctacgggga ctacggagg ctccagtctg ctactacctg gataaaggtc taaaagtctg      960
caggatgtga cagataccgg agggaagtgg gttactgaac agtggagtag ttcctccatt     1020
cccatctgaa tcctcattgc accttgtcga ttccagttgt ccacctacgg taaaaccttg     1080
agaaccctgc tttcctgcaa tcctggtacc cctcgaggga gtcacaggac aggaagagtt     1140
ctgggctcaa atcttagctt tgctacttgt taataatgct attgctgcga ctagaaactg     1200
ggtgtgctca agatggacag agggaaggga aggcaggagc tgcctctccc catttccagc     1260
taaatacctg cggtgtcccc ggagggcacc cagaagtctc attgaacact ctctcccggt     1320
ccccaggaac cctggcagag aagagcccc gcccgtgcag cgccgcgccc tgcgcgattc     1380
cctgagtgtg cgcgcccct tccggcggcc cgacgcggcg cagctccggg ctgcatataa     1440
aggcagcgtg gcgcgcagcc ccagcgcgag aaccagagcc aagcggcacc gagtgacagc     1500
gcgctgagag agaggcttaa gatctccgga gcggctcgcc atgg                       1544

<210> SEQ ID NO 15
<211> LENGTH: 3014
<212> TYPE: DNA
```

<213> ORGANISM: Mus musculus

<400> SEQUENCE: 15

```
ggactagatc ctggatccct gggtatgagg aaggagggga gttgtgccta gattcctaga      60
tcctgagaga caagggacct ggaggagttc caaaggatag aatcagaggc atccatgtgt     120
gtaagaagtt gtatccagaa gctggctcct gtgtacttcg ggagctgttc tgggacagtg     180
tgagcttcca gaggttaaag caagcccttc tgtctttccg tgggcttgac cttagcacga     240
cttttcttcg ggggaaagtt atgaataatt ctgtgttcat cacagaacac aggatgatgg     300
gctgccgcgc ggtggtggct acaccttaa ttacagcact ccaagacag aggcaggcag      360
atctctttga gttcgaggcc agccagcctg atctgcatag tgagttccag tacagccaca     420
acagaacaaa caaacaaaca aagatgcaag gtcaaagaga ccaaagttaa cccaagtgca     480
ctgggtgagc cagtgagtgg actggaaata cttgcagggg catagagaag cccaccccaa     540
catggaagac tcatggaaga cgcatttctg gggtacactg ctcaacttgt agtcagctgg     600
gcagaagagt cttcctgtcc tctcttaatt gtttgctgct catatattac ttcagctttg     660
ggaggggcct catagcacag ccctgtaact ttctgagcct tggggttct atggtttgtc      720
tttctaacat gtaattattg tgtgtgtgca tgtatgtgta cacccatag ccagtgtatg      780
gaggtcagag gacaatttgc agaattccac atggtctatc caccatgtgg gtcttgggga     840
cagaactcag cttatcatgc tctgttgtaa gtctctttct ttctttcttt ctttcttttct    900
ttctttcttt caatttattt atttattttc catatatgag tacattgtag ctatacagat     960
ggttgtgagc catcatgtgg ttgctgggaa ttgaactcag gacctctgct tgctccagcc    1020
ctgcttgctc cagcccaaag atttatttat tattatatgt acgctgtaca tataataata    1080
aatacataca taagtaatat tattattata ataataaata agtacactgt agctgttttc    1140
ggacccacca aagagggtg tcagatctca ttacggatgg ttgtgagcca ccatgtggtt     1200
gctgggattt gaactcagga ccttcagaag agcaatcagt gctcttacct gctgagtcat    1260
ctcaacagcc catgttgtaa gtatctttac ccactgagcc atttagttgg cccttagtct    1320
ctatagcttt tgagttattt gagtcccctcc cctccctcta tcagctgatg ttcaattcag    1380
aagaaataac tacagaactg acaatagtaa taagaaaatt ggacctggaa accaccttct    1440
catatctttta gtggcatcag ccgagaggtc agacagttaa catcctgaga agggctctgg   1500
catttggtcc tagttctgag cctctaggac aaggagacag aagctgtggt ttgcagtgta    1560
aaaaaagaga tgtggctggg cagtggtggc acatgccttt aatcccagca catggaaggc    1620
agaggcaggt ggatctctga gttcaaggcc agcctggtct acagagtgag ttccaggcca    1680
gccatggcta cacagagaaa ccccgtctcg aaaaaacaaa acaaacaaaa agatgttagt    1740
ccttccactc acttcccatg tcagggttac atggtacact agaaggccga gaggcctgtc    1800
ctgaggtcta gccctgcatg actgatctcg aaaactagag atttcagtgg actgctcaat    1860
gagaatggag ggagttgaat tttcctgtac ttgaggtacc tgttagctga gtccctggag   1920
gaagtgataa gctcagagat aagaaagcag aaactgagca gtcttcaatt ctccaggtct   1980
gaggtaggat tggggtggg gtgggtgaag cttgaaagga gggagaaaag aaagcataat    2040
gttcctggtc agagatctct ggaagaggag tgagaaggat gcaggtccag tactctggtt    2100
agatgtggga ggtggaatag aagatggaat tttgagtggg taggggctgc taaggtctat    2160
gttgctctta tgtacacgaa atcttttcac agggcataaa gtatgaggaa gttagagtct    2220
tggctatgga gaagttagag atgactgagt cgctgtggat aaaagaggga actttgtaca    2280
```

```
cagggcctgg ggtaaaaaaa aaaccctagg tcacacacag gaggaagtga agtacaggct    2340
agatcttaga ccatatcttt cattgctggg tgggtggttt tgttgtttgt tataaaacag    2400
ggtttgtttg tttgtttgtt tgtttgtaat aaaacagagt agccttgacc attctggaac    2460
tcactctgta gaccaggttg gctttgtttg ttttaaaggc agaaccacat tctgtagccc    2520
aagctagctt ggactttatt acagagccga ggctggtctc catctcacag tagccttccc    2580
actttagcct cccaatttct aagatcatgg gtgtgccctt cttgacttgg tttgcgtagt    2640
gcagggttca gatccaaggc ttcctgaatg atatagacaa gcgtgttacc agctaagcca    2700
catccccacg gtcaaagttg taggtgtatg tttggggtga gtctgtatgt gttcgcatgg    2760
aggtcagaag ttggtttttt ccttccagga gttatgtccc agtaagccag ctctagtttt    2820
ccagcatggc agcacacact cccgtggata ggatgctgac tccctgggaa agggaagcaa    2880
gaagtatagc tttgagtgtt tggattttgg gttttcttat gggtagggct aggatgagcc    2940
tagaacctag atgaccaatt cattttttata gtttatagac aagttccata tattaagaca    3000
catccttttc agaa                                                      3014

<210> SEQ ID NO 16
<211> LENGTH: 3171
<212> TYPE: DNA
<213> ORGANISM: Mus musculus

<400> SEQUENCE: 16
gatctttcag gaaacactag taggtaacag catgagtctc tccccaagaa ggcttgacta      60
atctattaga aatcctatgt gtggacatgt tcataagaga gcatgatgga atccttcatg     120
tgcttgaacc catagtaaaa tatctgagca ttttcttttc cccttgaagg ctaagaaagc     180
attcattcaa cctgaaaggt tctggttctc ccatatgcat agtgatttga actgccatgt     240
cttagtcagg gtgtttattc ctggacaaac atcatgacca agaagcaagt tggggaggaa     300
agggtttatt tggcttacac ttccagactg ctgttatcac caaggaagtc aggactggaa     360
ctcaagcagg tcaggaagca ggagctgatg cagaggccat ggaggatgt tccttactgg     420 cttgcctccc ctggcttgct tagcctgctc tcttatagaa ccaagattac cagcccagag     480
atggtcccac ccacaagggg cctttccccc ttgatcacta attgagaaaa tgccttacag     540
ctggatctca tggaggcatt tccccaactg aagctccttt ctctgtgata actccagctg     600
tgtcaagttg acacaaacta gccagtacat gccagtaggg cctaagtcta aatacagatg     660
caataattca gtaacatgaa atgggaagga gtttaattgt gctggagatt ttttttctcc     720
tcttatgaca cgtgggatcg tgaacctgtt cacctgaatg ctgtgtaatg aggcctaaga     780
ggcaagtcat aagagtgctt tgcaatgctt ttggaaagtt taatcttatg gaacaatcac     840
agtattcaaa gggtgtgtac ttcttccaga atcctagaag gtgagagagg ttcctgaata     900
tttgaaaaat aacaccctcc caatcttggt taatgaactg aaaaattcgg caggcaaaag     960
gcagaaatag ttcttaagtt acttcagagc tgtagaactg aaacacacac ttgtttagtg    1020
tccttaaact caatttaatt ttgaagtgac accaaaaatg tctaaaaaga gatgttgatt    1080
ttaaatgaga gtcaagact aatagttatt taagagaaaa atgtattta tgaagttaca    1140 tttcttctgc taaaaaaaat tatccaggaa aaatattac cttagaaaat caaaatgaaa    1200
aaaaaaagaa aatcaaaatg taaattgaag aaattgaaga ctataacatt caaagatgtt    1260
gaggatgcca tgtttacagc ttgttaatct gagttgatac aaactaaaag aactaatcta    1320
```

| | |
|---|---|
| gaaatgttct ttaaattta aattatatat gcttttgtac taacaatagt acccctatga | 1380 |
| ccaggaaaaa atgtatatct aaaataaata tctgaagata tttgttgcag ctgtttgtca | 1440 |
| cagtagaaca ctaaaaaaga tggaatgtct acaattagga tggaaaacta tgttatgtaa | 1500 |
| acatgggcta atggaggaag tgtctaccga ggaacaaact tttgtatgag gatgtgactt | 1560 |
| gggtaggctg agattcagtt ttccctggaa attaagaggt atatgaacaa aagtaactga | 1620 |
| cgtgtattgg gtcaaatgcc cctttacctt tgtaagccac agaaggtaag gttaatacgt | 1680 |
| tttattgcac tacttgcagg acctagcaaa gtacctgacc caaaagctgt tgataagtgt | 1740 |
| tcactgaatg gatgaaaata taaacaactg ggcatgcaca taatctttt aagtaaaaac | 1800 |
| aatatccttg ttatcctctc agagtttggc ttgctttgtg tataatatca gtctgagatt | 1860 |
| tgtgtgagaa tcagataagg tgatgaaagt caaaacttac atccatgaaa actttagagt | 1920 |
| atcatggctg caggacttgt ctggagaaga caattggttg cctcacaatc ccactattgg | 1980 |
| aggaaacaca aatgtggtga attccatatt ctatgacaca cgtgaaacct gtggcgcttc | 2040 |
| atgagctcgt tttgaaagtt tataccacac tggtttgctt ttgtttactg taaccagaca | 2100 |
| catagggttc attttcagca gaccataagg tctcaaaaga tggacaatta gataacttag | 2160 |
| aaatacttac gtaaaagaaa acctaaatac agtatttgtc atattaaaat accaattgta | 2220 |
| acatgtagcc ggatattttt cccacctcta atgatttcca gtttctggaa aaaaatccct | 2280 |
| cacctagaga tagaagcagc gcagctgtaa atcagtgag tgggctgct acggagtcac | 2340 |
| tggttagcct ggtgacattt ctttcagttt ctactttgta agatgcaagt aactaatggc | 2400 |
| atcgataaaa tcacttcctt cctaacatct taaattctta taagttaatt ctactacatt | 2460 |
| ccaataattc tgcttcaagc tcaaaaagta acaacagcaa gagcagcaga ctcctgcatt | 2520 |
| ctgctgtctc taagcatagc tcacatctta aacagccacg tgatggtctc cattagcgca | 2580 |
| atatgaagca ttgttacaat taaccacagc aacgtatgca ttaatcaaat taaactaaca | 2640 |
| cttgacatct gattttgttc aaatactcaa ctgcctcgat aaatactaag tagacaaaat | 2700 |
| ctccactgac gtggtttatc agtcagcttt cccttccatc tgaaaaaaa tcaaacaatt | 2760 |
| ctaggtatgt tgctttactc taacattcag gagtgaaagc ctccctgaac ctggggatg | 2820 |
| tgaggagaaa tgagtctgag caagggatcc ccaccacctg ctgcttccta gactccaaaa | 2880 |
| ctccagctcc agctatttcc tgggaagaga gaaatcggag gggaggggaa gaaggttggt | 2940 |
| gagagcaaga ggcgggagct aggaaaagga ggcaggagga ggcgtggccc ggcctggggc | 3000 |
| cggcgggata aatacagaga actgggtgcg gggtgcggga actccggag gacgcccgaa | 3060 |
| cggagcagca ccgcggacag cgccccgccg cgccgcgccc agctcagcct gcgcagccct | 3120 |
| ctcgcccgag gttcgcgctc cgcgcactct caaactagcc gctgcaccac g | 3171 |

<210> SEQ ID NO 17
<211> LENGTH: 1568
<212> TYPE: DNA
<213> ORGANISM: Mus musculus

<400> SEQUENCE: 17

| | |
|---|---|
| taaaaatagt aatggtattc ttttaattga tcttcagggt ttcattccta ctactctctg | 60 |
| tatttccagt agcagcccat tctccctaga actgcgcagc tcttgggtat gatttggcag | 120 |
| taccttacct ttagttccct aaaggaaatg ctcctcctac taaactgtga ttccctcaaa | 180 |
| gtacctgtct tgcttatgtt atagtgggtc acacattcat gccagatgcc aggaaaccga | 240 |
| ggcgaggaag aaacctatgt ccgtgctcct tcccaggcta ggttgtctga agaaagatag | 300 |

```
caacagtgca ctcatataca taaaataaat aaataaatct aaaaaagaga aagaaggaa    360 ggaaggaagg aaggaaggaa ggaaggaagg aaggaaggaa ggaaggaaga aaaagatgga    420
aggaagggaa gaaagaaaga gagaaaggtt gctaggaatt gaactcagga cctcaggaag    480
agcactgact gctcttagcc gctgagcatc attccagccc cctctttctt tctttctttc    540
tttctttctt tctttctttc tttctttctt tctttcttaa aaagaacttt acactgcaga    600
tatgtcatga atattaaatg aaattgcacg agaaagtccg tggctacatg accccaagat    660
gccccgttca aaacagcaa tgtgcttccg tcctgccctt tcctccgagc tcctcgcctt    720
tcaaaaggag gttaaacaag atcagatgcc cttttttct gcagaaggaa attagaattg    780
tatttctcag tgtcctgtta agaggttggt tcctggagtg tgggaatagc ggaagtgagg    840
ttccaaagta aattagagag aagagcatcc ttcgggcaga atggccacct gagccttggg    900
tgccccacct tctaacctct gcaactgcac ccaatcccaa gccctcccca ttcctcagca    960
ccattttact gcgtctctag gaatggattc ggactttgca ggcatttgga ggtttagatg   1020
gtatcatctt cacccacatt gtggtggaag tagcatcact ctgatgccct gggcattggg   1080
cgttgtgttt cccagggaaa gaagagaagt gtgcctagac agcaggggga caaatgggcc   1140
ggctgggtat actgtggcat ctcaggcgac acaagggaga gtgtggccac ctcttccaac   1200
ttgaccaccc tgatctcagg ctctgggagg ctgctacccc ctccggctcc cacccaagtc   1260
cttccacagg tgggagtgga ccgccatggt ttaattccat tctccagctc agagccaact   1320
gcgtggtgtc ctgagtcaga cactcggcca gggagcgcgt gtcctgcggg gcggcagca    1380 ggtccgggtg acgccaggga gccaggggcg gcgaggtcac gcgtgaagac cacgccagcc   1440
cagcccacgt gtgcgccaga tttaaaagtt ggtggcgcgc ggagatggtc actttggtgt   1500
ctgagctcag caagaggagg cgcacaggac acgctgaggg acagctaaaa caccgcaca   1560 acacaggg                                                          1568
```

<210> SEQ ID NO 18
<211> LENGTH: 224
<212> TYPE: PRT
<213> ORGANISM: Homo sapiens

<400> SEQUENCE: 18

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Ser Ser Gly His Cys Gln Tyr Leu Pro Pro Gly
    130                 135                 140

```
Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
    210                 215                 220
```

<210> SEQ ID NO 19
<211> LENGTH: 229
<212> TYPE: PRT
<213> ORGANISM: Homo sapiens

<400> SEQUENCE: 19

```
Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
                20                  25                  30

Leu Val Lys Asn Tyr Asn Pro Leu Glu Arg Pro Val Ala Asn Asp Ser
            35                  40                  45

Gln Pro Leu Thr Val Tyr Phe Ser Leu Ser Leu Leu Gln Ile Met Asp
        50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Ser Ser Gly His Cys Gln Tyr Leu Pro Pro Gly
    130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
    210                 215                 220

Thr Met Arg Arg Arg
225
```

<210> SEQ ID NO 20
<211> LENGTH: 233
<212> TYPE: PRT
<213> ORGANISM: Homo sapiens

<400> SEQUENCE: 20

```
Met Arg Cys Ser Pro Gly Gly Val Trp Leu Ala Leu Ala Ala Ser Leu
1               5                   10                  15
```

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Ser Ser Gly His Cys Gln Tyr Leu Pro Pro Gly
    130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
    210                 215                 220

Thr Met Arg Arg Arg Thr Leu Tyr Tyr
225                 230

<210> SEQ ID NO 21
<211> LENGTH: 471
<212> TYPE: PRT
<213> ORGANISM: Artificial Sequence
<220> FEATURE:
<223> OTHER INFORMATION: alpha7-5HT3 chimeric receptor

<400> SEQUENCE: 21

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Ser Ser Gly His Cys Gln Tyr Leu Pro Pro Gly
    130                 135                 140

```
Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
            165                 170                 175

Ser Leu Asp Leu Gln Met Gln Glu Ala Asp Ile Ser Gly Tyr Ile Pro
        180                 185                 190

Asn Gly Glu Trp Asp Leu Val Gly Ile Pro Gly Lys Arg Ser Glu Arg
    195                 200                 205

Phe Tyr Glu Cys Cys Lys Glu Pro Tyr Pro Asp Val Thr Phe Thr Val
210                 215                 220

Ile Ile Arg Arg Arg Pro Leu Phe Tyr Ala Val Ser Leu Leu Leu Pro
225                 230                 235                 240

Ser Ile Phe Leu Met Val Val Asp Ile Val Gly Phe Cys Leu Pro Pro
            245                 250                 255

Asp Ser Gly Glu Arg Val Ser Phe Lys Ile Thr Leu Leu Leu Gly Tyr
        260                 265                 270

Ser Val Phe Leu Ile Ile Val Ser Asp Thr Leu Pro Ala Thr Ile Gly
    275                 280                 285

Thr Pro Leu Ile Gly Val Tyr Phe Val Val Cys Met Ala Leu Leu Val
290                 295                 300

Ile Ser Leu Ala Glu Thr Ile Phe Ile Val Arg Leu Val His Lys Gln
305                 310                 315                 320

Asp Leu Gln Arg Pro Val Pro Asp Trp Leu Arg His Leu Val Leu Asp
            325                 330                 335

Arg Ile Ala Trp Ile Leu Cys Leu Gly Glu Gln Pro Met Ala His Arg
        340                 345                 350

Pro Pro Ala Thr Phe Gln Ala Asn Lys Thr Asp Asp Cys Ser Gly Ser
    355                 360                 365

Asp Leu Leu Pro Ala Met Gly Asn His Cys Ser His Val Gly Gly Pro
370                 375                 380

Gln Asp Leu Glu Lys Thr Pro Arg Gly Arg Gly Ser Pro Leu Pro Pro
385                 390                 395                 400

Pro Arg Glu Ala Ser Leu Ala Val Arg Gly Leu Leu Gln Glu Leu Ser
            405                 410                 415

Ser Ile Arg His Phe Leu Glu Lys Arg Asp Glu Met Arg Glu Val Ala
        420                 425                 430

Arg Asp Trp Leu Arg Val Gly Tyr Val Leu Asp Arg Leu Leu Phe Arg
    435                 440                 445

Ile Tyr Leu Leu Ala Val Leu Ala Tyr Ser Ile Thr Leu Val Thr Leu
450                 455                 460

Trp Ser Ile Trp His Tyr Ser
465                 470

<210> SEQ ID NO 22
<211> LENGTH: 430
<212> TYPE: PRT
<213> ORGANISM: Artificial Sequence
<220> FEATURE:
<223> OTHER INFORMATION: Alpha7-GlyR chimeric receptor

<400> SEQUENCE: 22

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30
```

Leu Val Lys Asn Tyr Asn Pro Leu Glu Arg Pro Val Ala Asn Asp Ser
                35                  40                  45

Gln Pro Leu Thr Val Tyr Phe Ser Leu Ser Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Arg Phe Pro Asp Gly Gln Ile Trp Lys Pro Asp Ile Leu
                100                 105                 110

Leu Tyr Asn Ser Ala Asp Glu Arg Phe Asp Ala Thr Phe His Thr Asn
                115                 120                 125

Val Leu Val Asn Ser Ser Gly His Cys Gln Tyr Leu Pro Pro Gly Ile
                130                 135                 140

Phe Lys Ser Ser Cys Tyr Ile Asp Val Arg Trp Phe Pro Phe Asp Val
145                 150                 155                 160

Gln His Cys Lys Leu Lys Phe Gly Ser Trp Ser Tyr Gly Gly Trp Ser
                165                 170                 175

Leu Asp Leu Gln Met Gln Glu Ala Asp Ile Ser Gly Tyr Ile Pro Asn
                180                 185                 190

Gly Glu Trp Asp Leu Val Gly Ile Pro Gly Lys Arg Ser Glu Arg Phe
                195                 200                 205

Tyr Glu Cys Cys Lys Glu Pro Tyr Pro Asp Val Thr Phe Thr Val Thr
                210                 215                 220

Met Arg Arg Arg Met Gly Tyr Tyr Leu Ile Gln Met Tyr Ile Pro Ser
225                 230                 235                 240

Leu Leu Ile Val Ile Leu Ser Trp Ile Ser Phe Trp Ile Asn Met Asp
                245                 250                 255

Ala Ala Pro Ala Arg Val Gly Leu Gly Ile Thr Thr Val Leu Thr Met
                260                 265                 270

Thr Thr Gln Ser Ser Gly Ser Arg Ala Ser Leu Pro Lys Val Ser Tyr
                275                 280                 285

Val Lys Ala Ile Asp Ile Trp Met Ala Val Cys Leu Leu Phe Val Phe
                290                 295                 300

Ser Ala Leu Leu Glu Tyr Ala Ala Val Asn Phe Val Ser Arg Gln His
305                 310                 315                 320

Lys Glu Leu Leu Arg Phe Arg Arg Lys Arg Arg His His Lys Glu Asp
                325                 330                 335

Glu Ala Gly Glu Gly Arg Phe Asn Phe Ser Ala Tyr Gly Met Gly Pro
                340                 345                 350

Ala Cys Leu Gln Ala Lys Asp Gly Ile Ser Val Lys Gly Ala Asn Asn
                355                 360                 365

Ser Asn Thr Thr Asn Pro Pro Pro Ala Pro Ser Lys Ser Pro Glu Glu
                370                 375                 380

Met Arg Lys Leu Phe Ile Gln Arg Ala Lys Lys Ile Asp Lys Ile Ser
385                 390                 395                 400

Arg Ile Gly Phe Pro Met Ala Phe Leu Ile Phe Asn Met Phe Tyr Trp
                405                 410                 415

Ile Ile Tyr Lys Ile Val Arg Arg Glu Asp Val His Asn Gln
                420                 425                 430

<210> SEQ ID NO 23
<211> LENGTH: 466

<212> TYPE: PRT
<213> ORGANISM: Artificial Sequence
<220> FEATURE:
<223> OTHER INFORMATION: alpha7-5HT3 chimeric receptor

<400> SEQUENCE: 23

```
Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Ser Ser Gly His Cys Gln Tyr Leu Pro Pro Gly
    130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
    210                 215                 220

Ile Ile Arg Arg Arg Pro Leu Phe Tyr Val Val Ser Leu Leu Leu Pro
225                 230                 235                 240

Ser Ile Phe Leu Met Val Met Asp Ile Val Gly Phe Tyr Leu Pro Pro
                245                 250                 255

Asn Ser Gly Glu Arg Val Ser Phe Lys Ile Thr Leu Leu Leu Gly Tyr
            260                 265                 270

Ser Val Phe Leu Ile Ile Val Ser Asp Thr Leu Pro Ala Thr Ala Ile
        275                 280                 285

Gly Thr Pro Leu Ile Gly Val Tyr Phe Val Val Cys Met Ala Leu Leu
    290                 295                 300

Val Ile Ser Leu Ala Glu Thr Ile Phe Ile Val Arg Leu Val His Lys
305                 310                 315                 320

Gln Asp Leu Gln Gln Pro Val Pro Ala Trp Leu Arg His Leu Val Leu
                325                 330                 335

Glu Arg Ile Ala Trp Leu Leu Cys Leu Arg Glu Gln Ser Thr Ser Gln
            340                 345                 350

Arg Pro Pro Ala Thr Ser Gln Ala Thr Lys Thr Asp Asp Cys Ser Ala
        355                 360                 365

Met Gly Asn His Cys Ser His Met Gly Gly Pro Gln Asp Phe Glu Lys
    370                 375                 380
```

```
Ser Pro Arg Asp Arg Cys Ser Pro Pro Pro Arg Glu Ala Ser
385                 390                 395                 400

Leu Ala Val Cys Gly Leu Leu Gln Glu Leu Ser Ser Ile Arg Gln Phe
            405                 410                 415

Leu Glu Lys Arg Asp Glu Ile Arg Glu Val Ala Arg Asp Trp Leu Arg
            420                 425                 430

Val Gly Ser Val Leu Asp Lys Leu Leu Phe His Ile Tyr Leu Leu Ala
            435                 440                 445

Val Leu Ala Tyr Ser Ile Thr Leu Val Met Leu Trp Ser Ile Trp Gln
            450                 455                 460

Tyr Ala
465

<210> SEQ ID NO 24
<211> LENGTH: 428
<212> TYPE: PRT
<213> ORGANISM: Artificial Sequence
<220> FEATURE:
<223> OTHER INFORMATION: alpha7-GABAc chimeric receptor

<400> SEQUENCE: 24

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
            35                  40                  45

Gln Pro Leu Thr Val Tyr Phe Ser Leu Ser Leu Leu Gln Ile Met Asp
50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
            115                 120                 125

Asn Val Leu Val Asn Ser Ser Gly His Cys Gln Tyr Leu Pro Pro Gly
130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
            195                 200                 205

Phe Tyr Glu Cys Cys Lys Glu Pro Tyr Pro Asp Val Thr Phe Thr Val
            210                 215                 220

Thr Met Arg Arg Arg Thr Leu Tyr Tyr Leu Leu Gln Thr Tyr Phe Pro
225                 230                 235                 240

Ala Thr Leu Met Val Met Leu Ser Trp Val Ser Phe Trp Ile Asp Arg
                245                 250                 255

Arg Ala Val Pro Ala Arg Val Pro Leu Gly Ile Thr Thr Val Leu Thr
            260                 265                 270
```

-continued

```
Met Ser Thr Ile Ile Thr Gly Val Asn Ala Ser Met Pro Arg Val Ser
            275                 280                 285

Tyr Ile Lys Ala Val Asp Ile Tyr Leu Trp Val Ser Phe Val Phe Val
        290                 295                 300

Phe Leu Ser Val Leu Glu Tyr Ala Ala Val Asn Tyr Leu Thr Thr Val
305                 310                 315                 320

Gln Glu Arg Lys Glu Gln Lys Leu Arg Glu Lys Leu Pro Cys Thr Ser
                325                 330                 335

Gly Leu Pro Pro Arg Thr Ala Met Leu Asp Gly Asn Tyr Ser Asp
            340                 345                 350

Gly Glu Val Asn Asp Leu Asp Asn Tyr Met Pro Glu Asn Gly Glu Lys
        355                 360                 365

Pro Asp Arg Met Met Val Gln Leu Thr Leu Ala Ser Glu Arg Ser Ser
370                 375                 380

Pro Gln Arg Lys Ser Gln Arg Ser Ser Tyr Val Ser Met Arg Ile Asp
385                 390                 395                 400

Thr His Ala Ile Asp Lys Tyr Ser Arg Ile Ile Phe Pro Ala Ala Tyr
                405                 410                 415

Ile Leu Phe Asn Leu Ile Tyr Trp Ser Ile Phe Ser
            420                 425

<210> SEQ ID NO 25
<211> LENGTH: 502
<212> TYPE: PRT
<213> ORGANISM: Rattus norvegicus

<400> SEQUENCE: 25

Met Gly Gly Gly Arg Gly Gly Ile Trp Leu Ala Leu Ala Ala Leu
1               5                   10                  15

Leu His Val Ser Leu Gln Gly Glu Phe Gln Arg Arg Leu Tyr Lys Glu
                20                  25                  30

Leu Val Lys Asn Tyr Asn Pro Leu Glu Arg Pro Val Ala Asn Asp Ser
            35                  40                  45

Gln Pro Leu Thr Val Tyr Phe Ser Leu Ser Leu Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Met Ser Glu Tyr Pro Gly
                85                  90                  95

Val Lys Asn Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Ala Ser Gly His Cys Gln Tyr Leu Pro Pro Gly
    130                 135                 140

Ile Phe Lys Ser Ser Cys Tyr Ile Asp Val Arg Trp Phe Pro Phe Asp
145                 150                 155                 160

Val Gln Gln Cys Lys Leu Lys Phe Gly Ser Trp Ser Tyr Gly Gly Trp
                165                 170                 175

Ser Leu Asp Leu Gln Met Gln Glu Ala Asp Ile Ser Ser Tyr Ile Pro
            180                 185                 190

Asn Gly Glu Trp Asp Leu Met Gly Ile Pro Gly Lys Arg Asn Glu Lys
        195                 200                 205

Phe Tyr Glu Cys Cys Lys Glu Pro Tyr Pro Asp Val Thr Tyr Thr Val
    210                 215                 220
```

-continued

```
Thr Met Arg Arg Arg Thr Leu Tyr Tyr Gly Leu Asn Leu Leu Ile Pro
225                 230                 235                 240

Cys Val Leu Ile Ser Ala Leu Ala Leu Leu Val Phe Leu Leu Pro Ala
                245                 250                 255

Asp Ser Gly Glu Lys Ile Ser Leu Gly Ile Thr Val Leu Leu Ser Leu
            260                 265                 270

Thr Val Phe Met Leu Leu Val Ala Glu Ile Met Pro Ala Thr Ser Asp
            275                 280                 285

Ser Val Pro Leu Ile Ala Gln Tyr Phe Ala Ser Thr Met Ile Ile Val
        290                 295                 300

Gly Leu Ser Val Val Val Thr Val Ile Val Leu Arg Tyr His His His
305                 310                 315                 320

Asp Pro Asp Gly Gly Lys Met Pro Lys Trp Thr Arg Ile Ile Leu Leu
                325                 330                 335

Asn Trp Cys Ala Trp Phe Leu Arg Met Lys Arg Pro Gly Glu Asp Lys
            340                 345                 350

Val Arg Pro Ala Cys Gln His Lys Pro Arg Arg Cys Ser Leu Ala Ser
        355                 360                 365

Val Glu Leu Ser Ala Gly Ala Gly Pro Pro Thr Ser Asn Gly Asn Leu
    370                 375                 380

Leu Tyr Ile Gly Phe Arg Gly Leu Glu Gly Met His Cys Ala Pro Thr
385                 390                 395                 400

Pro Asp Ser Gly Val Val Cys Gly Arg Leu Ala Cys Ser Pro Thr His
                405                 410                 415

Asp Glu His Leu Met His Gly Ala His Pro Ser Asp Gly Asp Pro Asp
            420                 425                 430

Leu Ala Lys Ile Leu Glu Glu Val Arg Tyr Ile Ala Asn Arg Asn Arg
        435                 440                 445

Cys Gln Asp Glu Ser Glu Val Ile Cys Ser Glu Trp Lys Phe Ala Ala
    450                 455                 460

Cys Val Val Asp Pro Leu Cys Leu Met Ala Phe Ser Val Phe Thr Ile
465                 470                 475                 480

Ile Cys Thr Ile Gly Ile Leu Met Ser Ala Pro Asn Phe Val Glu Ala
            485                 490                 495

Val Ser Lys Asp Phe Ala
            500
```

US 11,713,470 B2

TARGETED GENE THERAPIES FOR PAIN AND OTHER NEURO-RELATED DISORDERS

CROSS REFERENCE TO RELATED APPLICATIONS

This application is the United States national phase of International Application No. PCT/US2018/023364 filed Mar. 20, 2018, and claims the benefit of U.S. Provisional Patent Application No. 62/473,630 filed Mar. 20, 2017, which is incorporated herein by reference in its entirety.

SEQUENCE LISTING

The Sequence Listing associated with this application is filed in electronic format via EFS-Web and is hereby incorporated by reference into the specification in its entirety. The name of the text file containing the Sequence Listing is 1905261_ST25.txt. The size of the text file is 88,884 bytes, and the text file was created on Aug. 8, 2019.

Provided herein are compositions and related methods useful for treatment of pain, especially chronic pain.

Over 100 million people in the U.S. suffer from debilitating pain caused by disease and trauma. Current therapies are focused on opioids and NSAIDs, but these treatments lose efficacy or produce serious side effects. Addiction to opioid-based prescription painkillers has led to an epidemic level rise in opioid-related overdose deaths. Because of the lack of adequate treatment options, pain continues to be a major clinical problem. Therapeutic solutions to the lack of adequate pain treatment, especially for chronic pain, are needed.

SUMMARY

Provided herein are nucleic acids for tissue-specific delivery of modified ligand-gated ion channels (LGICs) that can be selectively activated with tailored compound ligands. Such LGICs, once delivered to the neurons of interest by gene therapy methods, would render those neurons sensitive to a ligand selective for such novel LGICs and would obviate the need for local delivery of the ligand, since the tailored ligand would have no effect on native LGICs. Furthermore, selective activation of those tissue-targeted LGICs would eliminate the non-specific effects arising from activation of neighboring populations of neurons that inevitably occur due to the ubiquitous expression of native LGICs. This provides specificity for control of neuron activity that can be used therapeutically to treat neurological diseases and conditions, such as chronic pain or itch. Therefore, development of novel tissue-targeted LGICs with unique pharmacology has therapeutic utility. Related methods also are provided.

According to a first aspect of the invention, a nucleic acid is provided, comprising a gene for expressing a modified ligand-gated ion channel. The gene comprises an open reading frame encoding a modified ligand-gated ion channel under transcriptional control of transcriptional control elements governing cell-specific expression in CNS neurons, such as dorsal horn neurons, spinal cord cells, or brain cells, or in inhibitory neurons or nerve cells. Examples of transcription control elements include: a CCK promoter, a Tac1 promoter, an NTS promoter, an NMU promoter, a Calb1 promoter, an SST promoter, a GRPR promoter, a parvalbumin promoter, a Gal promoter, an NPY promoter, a PKCγ promoter, or a Calb2 promoter. The modified ligand-gated ion channel comprises a modified ligand binding domain activatable by an exogenous ligand, and optionally selective to the exogenous ligand, and an ion pore domain.

In another aspect of the invention, a method is provided of modulating (increasing or decreasing) the membrane potential of an excitable cell or a secretory cell. The method comprises expressing in the cell a genetic construct comprising a gene for expressing a modified ligand-gated ion channel, comprising an open reading frame encoding a modified ligand-gated ion channel under transcriptional control of transcriptional control elements governing cell-specific expression in CNS neurons, such as dorsal horn neurons, spinal cord cells, or brain cells, or in inhibitory neurons or nerve cells, such as a CCK promoter, a Tac1 promoter, an NTS promoter, an NMU promoter, a Calb1 promoter, an SST promoter, a GRPR promoter, a parvalbumin promoter, a Gal promoter, an NPY promoter, a PKCγ promoter, or Calb2 promoter and a modified ligand-gated ion channel comprising a modified ligand binding domain activatable by an exogenous ligand, and optionally selective to the exogenous ligand, and an ion pore domain, and contacting the cell with an amount of the exogenous ligand effective to activate the modified ligand gated ion channel thereby modulating the membrane potential of the cell.

In a further aspect of the invention, a method is provided of treating a disease or disorder associated with the nervous system in a patient. The method comprises delivering a nucleic acid as described below, and administering the exogenous ligand to the patient in an amount effective to activate a modified ligand gated ion channel in a patient thereby treating the disease or disorder associated with the nervous system in the patient. The nucleic acid comprises a gene for expressing the modified ligand-gated ion channel. The gene comprises an open reading frame encoding the modified ligand-gated ion channel under transcriptional control of transcriptional control elements governing cell-specific expression in CNS neurons, such as dorsal horn neurons, spinal cord cells, or brain cells, or in inhibitory neurons or nerve cells. Examples of transcription control elements include: a CCK promoter, a Tac1 promoter, an NTS promoter, an NMU promoter, a Calb1 promoter, an SST promoter, a GRPR promoter, a parvalbumin promoter, a Gal promoter, an NPY promoter, a PKCγ promoter, or a Calb2 promoter. The modified ligand-gated ion channel comprises a modified ligand binding domain activatable by an exogenous ligand, and optionally selective to the exogenous ligand, and an ion pore domain.

BRIEF DESCRIPTION OF THE DRAWINGS

FIGS. 1A-1O depict exemplary nucleic acid sequences, continuous over FIGS. 1A-1O, comprising promoter sequences useful in the genetic constructs described herein, as follows: Human CCK Promoter (SEQ ID NO: 1), Human Tac1 Promoter (SEQ ID NO: 2), Human Nts Promoter (SEQ ID NO: 3), Human Nmu Promoter (SEQ ID NO: 4), Human Calb1 Promoter (SEQ ID NO: 5), Human Parvalbumin Promoter (SEQ ID NO: 6), Human Gal Promoter (SEQ ID NO: 7), Human NPY Promoter (SEQ ID NO: 8), Human SST Promoter (SEQ ID NO: 9), Human GRPR Promoter (SEQ ID NO: 10), Human PRKCG Promoter (SEQ ID NO: 11), Human Calb2 Promoter (SEQ ID NO: 12), Mouse CCK Promoter (SEQ ID NO: 13), Mouse Calb2 Promoter (SEQ ID NO: 14), Mouse PRKCG Promoter (SEQ ID NO: 15), Mouse Calb1 Promoter (SEQ ID NO: 16), and Mouse NMU Promoter (SEQ ID NO: 17).

FIG. 2 provides amino acid sequences of exemplary α7-nicotinic acetylcholine receptor ligand binding domains (SEQ ID NOs: 18-20 as indicated in the figure).

FIGS. 3A-3E provide exemplary amino acid sequences for chimeric LGICs. FIG. 3A provides an exemplary amino acid sequence of an α7-5HT3 chimeric receptor (SEQ ID NO: 21), including a human α7 nAChR LBD and a murine 5HT3 IPD components. FIG. 3B provides an exemplary amino acid sequence of α7-GlyR chimeric receptor (SEQ ID NO: 22) including a human α7 nAChR LBD) and a human GlyR IPD components. FIG. 3C provides an exemplary amino acid sequence of α7-5HT3 chimeric receptor (SEQ ID NO: 23, including human α7 nAChR LBD and a human 5HT3 IPD components. FIG. 3D provides an exemplary amino acid sequence of α7-GABAC chimeric receptor (SEQ ID NO: 24), including a human α7 nAChR LBD and a human GABAC IPD components. FIG. 3E provides an exemplary amino acid sequence of rat nAChR sequence (SEQ ID NO: 25).

FIG. 13. Varenicline has no effect on baseline mechanical and heat sensitivity or CFA or sural SNI induced hypersensitivity in mice lacking PSAM4. PWT, frequency of response and PWL were tested in adult wildtype C57Bl/6 mice (not expressing PSAM4) before and after injection of varenicline (0.1 mpk, i.p) at baseline and 3 and 7 days after injection of CFA or sural-SNI surgery, respectively. Data are mean±SEM. N=5 mice. *p<0.05, p<0.01, *P<0.001; ns=not significant (i.e. p>0.05).

DETAILED DESCRIPTION

Figure 4:
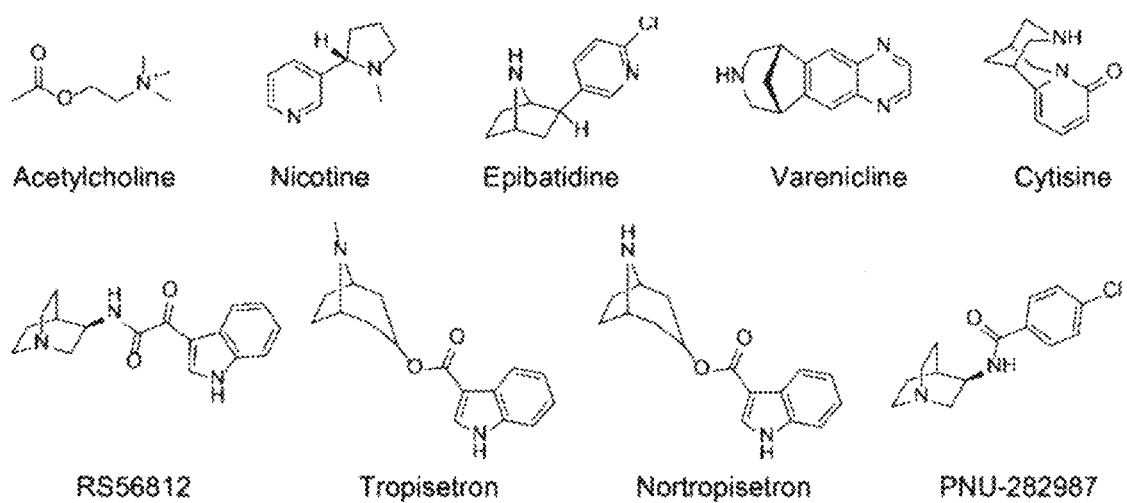
FIG. 4 provides exemplary exogenous ligands (US 2018/0009862 A1).

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

As used herein, the term "comprising" is open-ended and may be synonymous with "including", "containing", or "characterized by". The term "consisting essentially of" limits the scope of a claim to the specified materials or steps and those that do not materially affect the basic and novel characteristic(s) of the claimed invention. The term "consisting of" excludes any element, step, or ingredient not specified in the claim. As used herein, embodiments "comprising" one or more stated elements or steps also include, but are not limited to embodiments "consisting essentially of" and "consisting of" these stated elements or steps.

A "patient" is a human or animal, e.g., vertebrates or mammals, including rat, mouse, rabbit, pig, monkey, chimpanzee, cat, dog, horse, goat, guinea pig, and birds, and does not imply or require a doctor-patient or veterinarian-patient relationship.

The terms "transfect", "transfection", "transfected", and like terms refer to the introduction of a gene into a eukaryotic cell, such as a keratinocyte, and includes "transduction," which is viral-mediated gene transfer, for example, by use of recombinant AAV, adenovirus (Ad), retrovirus (e.g., lentivirus), or any other applicable viral-mediated gene transfer platform.

By "expression" or "gene expression," it is meant the overall flow of information from a gene. A "gene" is a functional genetic unit for producing a gene product, such as RNA or a protein in a cell, or other expression system encoded on a nucleic acid and generally comprising: a transcriptional control sequence, such as a promoter and other cis-acting elements, such as transcriptional response elements (TREs) and/or enhancers; an expressed sequence that typically encodes a protein (referred to as an open-reading frame or ORF) or functional/structural RNA; and a polyadenylation sequence). A gene produces a gene product (typically a protein, optionally post-translationally modified or a functional/structural RNA) when transcribed. By "expression of genes under transcriptional control of," or alternately "subject to control by," a designated sequence such as a promotor, it is meant gene expression from a gene containing the designated sequence operably linked (functionally attached, typically in cis) to the gene. A gene that is "under transcriptional control" of a promotor or transcription control element, is a gene that is transcribed at detectably different levels in the presence of a transcription factor, e.g., in specific cells, as further described below, and in the context of the present disclosure, produces a difference in transcription levels when expressed in a specific cell type (e.g., where the promoter is a CCK promoter, the gene is preferentially expressed in cells that express CCK natively. A "gene for expression of" a stated gene product is a gene capable of expressing that stated gene product when placed in a suitable environment, that is, for example, when transformed, transfected, transduced, etc. into a cell, and subjected to suitable conditions for expression. In the case of a constitutive promoter "suitable conditions" means that the gene typically need only be introduced into a host cell. In the case of an inducible promoter, such as the tissue specific promoters described herein, "suitable conditions" means when factors that regulate transcription, such as DNA-binding proteins, are present or absent, for example, an amount of the respective inducer is available to the expression system (e.g., cell), or factors causing suppression of a gene are unavailable or displaced—effective to cause expression of the gene.

Transcriptional control elements include promoters, enhancers, transcription factor-responsive elements (TREs, e.g., transcription factor binding sequences), suppressors, introns, etc., as are broadly-known. Additional transcription control elements, such as a WPRE (woodchuck hepatitis virus post-transcriptional regulatory element), or an intron, e.g., as shown below, which can increase expression from certain viral vectors, can be included in the gene.

Exemplary tissue specific promoters, specific to excitable cells or secretory cells, e.g. of the central nervous system (CNS), such as, without limitation, neurons, sensory neurons, dorsal horn cells, spinal cord cells, brain cells, and inhibitory neurons, include, for example and without limitation, those promoter sequences depicted in FIGS. 1A-1L, and described in Table 1.

TABLE 1

| Promoter | Location for Expression | Inhibitory or excitatory LGIC | Physiological Effect |
|---|---|---|---|
| Cholecystokinin (CCK) | Dorsal horn neuron | inhibitory | Blocks persistent pain |
| Tachykinin (Tac1) | Dorsal horn neuron | inhibitory | Blocks persistent pain |
| PKCγ (PRKCG) | Dorsal horn neuron | inhibitory | Blocks persistent pain |
| Neurotensin (NTS) | Dorsal horn neuron | inhibitory | Blocks persistent pain |
| Neuromedin U (NMU) | Dorsal horn neuron | inhibitory | Blocks persistent pain |
| Calbindin 1 (Calb1) | Dorsal horn neuron | inhibitory | Blocks persistent pain |

TABLE 1-continued

| Promoter | Location for Expression | Inhibitory or excitatory LGIC | Physiological Effect |
|---|---|---|---|
| Calbindin 2 (Calb2) | Dorsal horn neuron | inhibitory | Blocks persistent pain |
| Somatostatin (SST) | Dorsal horn neuron | inhibitory | Blocks persistent pain |
| Gastrin related peptide receptor (GRPR) | Dorsal horn neuron | inhibitory | Blocks itch |
| Galanin (GAL) | Dorsal horn neuron | Excitatory | Blocks persistent pain or itch |
| Neuropeptide Y (NPY) | Dorsal horn neuron | Excitatory | Blocks persistent pain or itch |
| Parvalbumin (PV) | Dorsal horn neuron | Excitatory | Blocks persistent pain or itch |

A promoter is "specific" to specified excitable cells or secretory cells if it causes gene expression in those cells of a gene to a sufficient extent for production of useful or therapeutically effective amounts of the described modified LGICs described herein in the specified excitable cells or secretory cells, and insignificant expression elsewhere in the context of the use, e.g. therapeutic use.

Although these are human sequences and consensus sequences, there is conservation among species and many promoter sequences that function in human cells will also be expected to do so in mice, or any mammal or vertebrate, and many promoter sequences that function in mice, or any mammal or vertebrate will also be expected to do so in human cells. The sequences also may be modified, e.g., shortened, for virion packaging purposes and optimal expression, so long as tissue-specificity of the construct remains.

One of the advantages of using highly circumscribed cell-type specific promoters described herein, for example, Calb2 or CCK to drive expression of PSAM4 or another LGIC (e.g., an inhibitory LGIC in Calb2 or CCK expressing dorsal horn neurons), is that baseline mechanical or heat sensitivity are not affected (see, Examples 1 and 2, below) with exogenous ligand-mediated activation of the LGIC. These promoters provide an important advantage over pan neuronal or pan excitatory neuron or pan inhibitory neuron promoters, or also primary afferent promoters such as TRPV1 (those neurons fibers are required for all heat sensation), which will negatively impact acute pain or touch in the area innervated by the targeted neurons with exogenous ligand-mediated activation of the LGIC. The ability to feel acute pain is important to protect the patient from bodily harm.

Production of useful nucleic acid constructs, such as recombinant viral vectors for production of nucleic acids, such as the genetic constructs and recombinant viral genomes described herein, is routine, in that molecular cloning and gene assembly methods are routine. Further, a number of companies can custom-synthesize and verify multi-kilobase genes, making the production of genes or genomes as described herein, such as rAAV or scAAV genomes, routine (See, e.g., Gene Synthesis Handbook, 2d Edition, 2014, GenScript USA, Inc.).

AAV (adeno-associated virus), is a virus belonging to the genus Dependoparvovirus, and family Parvoviridae. The virus is a small replication-defective, non-enveloped virus. AAV is not currently known to cause any disease by itself. AAV requires a helper virus, such as adenovirus or herpes simplex virus, to facilitate productive infection and replication. In the absence of helper virus, AAVs establish a latent infection within the cell, either by site-specific integration into the host genome or by persisting in episomal forms. Gene therapy vectors using AAV can infect both dividing and quiescent cells. Furthermore, AAV serotypes have different tropism and can infect cells of multiple diverse tissue types. While eleven serotypes of AAV have been identified to date, AAV2 was among the first to be identified and has been consistently used for the generation of recombinant AAV vectors. Further certain natural or modified AAVs transduce specific organs or cell populations. In one example, AAV-PHP.eB and AAV-PHP.S, capsids efficiently transduce the central and peripheral nervous systems, respectively, when administered intravenously (Chan, K. Y., et al. Engineered AAVs for efficient noninvasive gene delivery to the central and peripheral nervous systems (2017) Nat. Neurosci 20(8):1172-1179). For example, compared to AAV9, AAV-PHP.B delivers genes to the brain and spinal cord at least 40 times more efficiently. See also, Tervo, D G, et al. A Designer AAV Variant Permits Efficient Retrograde Access to Projection Neurons (2016) Neuron 92, 372-382, describing engineered AAV variants, e.g., rAAV2-retro, which permit robust retrograde access to projection neurons with efficiency comparable to classical synthetic retrograde tracers, and enable sufficient sensor/effector expression for functional circuit interrogation and in vivo genome editing in targeted neuronal populations.

The AAV virion shell is approximately 25 nm in diameter and encapsulates a single-stranded DNA genome that consists of two large open reading frames (ORFs) flanked by inverted terminal repeats (ITR). The ITRs are the only cis-acting elements required for genome replication and packaging. In wild-type AAV, the left ORF encodes four replication proteins responsible for site-specific integration, nicking, and helicase activity, as well as regulation of promoters within the AAV genome. AAV possesses a 4.7 kb genome, and as such, efficient packaging of recombinant AAV (rAAV) vectors can be performed with constructs ranging from 4.1 kb to 4.9 kb in size (see, e.g., Samulski, R J, et al., AAV-Mediated Gene Therapy for Research and Therapeutic Purposes, *Annu. Rev. Virol.* 2014. 1:427-51).

Helper-free production of the rAAV requires transfection of the following components into host cells, typically 293 cells (HEK293 cells), which are broadly available, or similar cell lines: (1) an rAAV vector containing the transgene expression cassette flanked by the two ITRs; (2) expression of Rep and Cap proteins, typically provided by a helper plasmid in trans; and (3) adenovirus genes encoding E1, E2A, E4, and virus-associated RNA, also provided, at least in part by another helper plasmid in trans (293 cells produce the Ad E1 gene in trans). Rep and Cap proteins, which are necessary for viral packaging, are replication proteins and capsid proteins, respectively. Rep proteins consist of rep 78, 68, 52 and 40. They specifically are involved with the replication of AAV. Cap proteins are comprised of three proteins, VP1, VP2 and VP3, with molecular weight of 87, 72 and 62 kDa, respectively. These capsid proteins assemble into a near-spherical protein shell of 60 subunits. Helper-free AAV packaging systems are broadly available, for example, from Clontech of Mountain View, Calif., from Cell Biolabs, Inc. of San Diego, Calif., and see, e.g., U.S. Pat. Nos. 6,093,570, 6,458,587, 6,951,758, and 7,439,065. In scAAV (self-complementary AAV), the right ITR contains a deletion of D-sequence (the packaging signal) and a terminal resolution site mutation ($\Delta$trs), which prevent Rep-mediated nicking and force packaging of dimer or self-complementary genomes (see FIG. 8). Making dsAAV from scAAV vector renders much improved transduction both in vitro and in vivo (see, e.g., pscAAV-MCS Expression vector, Product Data Sheet, Cell Biolabs, Inc., San Diego, Calif. (2012-2016)).

Preparation of rAAV transducing particles, such as scAAV transducing particles is routine. Since the transfection method is often considered unsuitable for large-scale production, the infection of cell lines stably expressing Rep and Cap with adenovirus carrying a vector genome has afforded the ability to scale-up. Another option includes infection of proviral cell lines with adenovirus or herpes simplex virus vector carrying an AAV Rep and Cap expression cassette. These methods still require the complete elimination of adenovirus (or herpesvirus) during the production process. However, in baculovirus expression vector systems for rAAV vector production in insect SF9 cells, the components of AAV production, including Rep and Cap proteins, as well as vector genomes are provided by separate recombinant baculoviruses. Ayuso, E., "Manufacturing of recombinant adeno-associated viral vectors: new technologies are welcome", *Molecular Therapy—Methods & Clinical Development* (2016) 3, 15049; doi:10.1038/mtm.2015.49, and Merten, O-W, et al., describe numerous robust current rAAV production methods, though commercial scale-up and validation needs improvement. High viral titers ($\sim 10^{12}$-$10^{13}$ vp/mL) may be required for certain uses described herein. Protocols are available in the literature for concentration and purification of AAV vectors, allowing production of virus at these high concentrations (see, e.g., Gray S J, et al. (2011) Production of recombinant adeno-associated viral vectors and use in in vitro and in vivo administration. *Curr Protoc Neurosci*. doi:10.1002/0471142301.ns0417s57 and Guo P, et al. (2012) Rapid and simplified purification of recombinant adeno-associated virus. *J Virol Methods* 183(2):139-146).

Once the virus has been produced in the, e.g., 293 cells, the cells are collected, lysed, and the resultant virus is purified. Density gradient ultracentrifugation, e.g., in cesium chloride or nonionic iodixanol (VISIPAQ™) gradients and column chromatography, such as ion-exchange, heparin-affinity, or mucin-affinity column chromatography, depending on the AAV serotype. Once the rAAV has been purified and concentrated to a suitable concentration, the virus can be used for in vitro cell transduction or for in vivo animal injection at an appropriate MOI (Multiplicity of Infection).

Numerous rAAV vectors have been made containing genes for expressing fluorescent proteins, and are commercially available. A "gene" is a genetic element for production of a gene product such as a protein or RNA. A gene for production of a protein product includes, from 5' to 3' according to convention: one or more regulatory elements (transcription control elements) such as promoters, transcription response elements (TREs), repressors, enhancers; an open-reading frame (ORF) encoding a protein or a sequence encoding a functional RNA; and a polyadenylation (pA) site. Due to size limitations, genes for use in rAAV vectors typically do not include introns. rAAV vectors also include the 5' ITR and 3' ITR flanking the gene, which is referred to as a transgene. Thus a typical rAAV genome has the following structure, in order from 5' to 3' on the sense strand: ITR—promoter—transgene ORF—pA—ITR, and in one aspect of the present invention, the promoter includes a TRE and the transgene ORF is that of a colorimetric, e.g., fluorescent protein. Methods of molecular cloning of rAAV transgene constructs, preparation of rAAV particles, and storage and use thereof are broadly-known and further technical details are unnecessary for one of ordinary skill in the art to be able to construct useful rAAV vectors, and produce and use rAAV particles as described herein. As indicated above, so long as the gene sequence is less than the packaging limit of rAAV or scAAV, it is useful for production of a transduction particle as described herein.

AAV is but one of many robust and well-characterized viral vectors suited for gene therapy, which also includes, without limitation, gammaretroviruses, lentiviruses, adenovirus, and herpes simplex virus. While AAV is likely preferred in many instances, other safe and effective viral transducing particles can be developed based on the genes described herein for use in the devices, systems and methods described herein.

Likewise, DNA, such as plasmid or other forms of DNA, optionally combined with suitable transfection reagents, such as liposomes.

In aspects, compositions and methods are provided for delivery of a gene to excitable cells or secretory cells, such as nerve cells or neurons, e.g., to sensory neurons, or inhibitory neurons or nerve cells, that encodes a protein comprising a ligand binding domain fused to a functional or effector domain (transmembrane ion channel or ion pore domain). As described in further detail below, the protein may be a mutated native (non-chimeric) protein, such as a mutated GlyR or α7-nicotinic acetylcholine receptor, or a chimeric protein, such as a protein comprising a mutated α7-nicotinic acetylcholine receptor ligand binding domain (LBD) and a GlyR transmembrane ion channel domain.

In all instances, ligand-gated ion channels and their respective LBDs and transmembrane domains, are broadly-known, and their nucleotide and amino acid sequences, including a large number of mutated sequences that selectively bind exogenous ligands, and transcription control elements, such as promoters, are broadly-available in the literature and free databases and sources, such as GenBank, UniProt, Addgene, EPD (eukaryotic promoter database), see, U.S. Pat. No. 8,435,762 and U.S. Patent Application Publication No. 2018/0009862, etc., among many other literature and on-line sources, and do not need to be recited herein. Likewise, methods of preparing genes encoding such proteins and for expressing such proteins in a tissue-specific manner is routine and need not be described beyond what is provided herein. Nevertheless, exemplary nucleic acid constructs, nucleic acid and amino acid sequences, recombinant virus particles, and related methods and reagents are provided herein for illustrative purposes, and as proof of concept.

Excitable cells or secretory cells include, for example and without limitation, sensory nerves and neurons including, without limitation, CNS neurons, such as spinal cord cells, such as dorsal horn cells and/or brain cells, including and without limitation a brainstem, hindbrain, midbrain or forebrain excitatory or inhibitory cell population.

The functional domain of the modified LGICs described herein is a transmembrane ion channel that can be cationic-selective or anion-selective. Cationic-selective (e.g., $Na^+$—$Ca^{2+}$—, and $K^+$-selective) channels, such as that of the 5HT3 receptor (also, 5-HT3 receptor, or 5-hydroxytryptamine type 3 receptor), and the α7-nicotinic acetylcholine receptor, have an excitatory, depolarizing effect on a neuron, while anion-selective (e.g., $Cl^-$-selective) channels, such as that of the glycine receptor (e.g., GlyR) or GABA A receptor, have an inhibitory, hyperpolarizing effect on the neuron. In one aspect, for pain management, the ion channel is hyperpolarizing, that is, when active, that is, when bound to the agonist ligand, the ion channel decreases a neuron's membrane potential to values more negative (e.g., −90 millivolts (mV)) than resting potential (e.g., −70 mV). In aspects, a hyperpolarizing ion channel is permeable to Cl⁻ or K⁺ ions, and thereby decreases neuron membrane potential when active. GlyR is permeable to Cl⁻, and therefore, when active, transfers Cl⁻ ions into the neuron. Suitable ion channels include transmembrane domains of members of the Cys-loop family of receptors. Non-limiting examples of suitable hyperpolarizing ion channels include: Glycine receptors; GABA receptors, such as $GABA_A$ and $GABA_C$ receptors; Glutamate-gated chloride receptors.

In another aspect, for pain management, the ion channel is depolarizing, and the cell is an inhibitory neuron. For example, as indicated in Table 1, NPPY, Gal, or PV promoters can be used to effectively target inhibitory neurons in the dorsal horn.

In one aspect, the protein is a mutated ligand-gated ion channel, such as GlyR, $GABA_A$, α7-nicotinic acetylcholine receptor, or 5HT3 receptor, having mutations in the protein causing enhanced selectivity of binding to exogenous ligands (ligands not naturally found in the cell in which the protein is expressed). In reference to binding of a ligand, by "selective to" it is meant either exclusive to or substantially or sufficiently exclusive binding to a ligand, such that the effect of the other ligand is insignificant or below a suitable or acceptable threshold level to achieve a desired purpose. For example, an LGIC having a mutated α7-nicotinic acetylcholine LBD can be selective to an exogenous small molecule compound, such as varenicline, such that the LGIC is activated by the exogenous small molecule compound, and not to any clinically-relevant or physiologically-relevant extent by acetylcholine. Selective binding to an exogenous ligand is, compared to binding to an endogenous ligand, at least about 4-fold to at least about 200-fold enhanced potency as an agonist to the LGIC, including increments there between (see, e.g., U.S. 2018/0009862). Optionally, though preferably in many instances, the LGIC exhibits reduced binding to endogenous ligands (native ligands), such as in the case of the α7-nicotinic acetylcholine ligand binding domain, reduced, negligible, or no binding to acetylcholine, but enhanced binding to exogenous ligands, such as, for example and without limitation, varenicline (e.g., CHANTIX®).

Methods of modification or mutation of ligand-gated ion channel proteins, including production of chimeric proteins, able to bind selectively to exogenous ligands, and examples of such proteins are broadly-known, and well within the skill of an ordinary artisan (see, e.g., U.S. Pat. No. 8,435,762; U.S. Patent Application Publication No. 2018/0009862; U.S. Pat. No. 8,957,036, incorporated herein by reference in its entirety; International Patent Publication No. 2017/049252, incorporated herein by reference for its description of additional modified LGICs; Weir et al., Using an engineered glutamate-gated chloride channel to silence sensory neurons and treat neuropathic pain at the source (2017) Brain 140; 2570-2585; Kynagh, T., et al., An Improved Ivermectin-activated Chloride Channel Receptor for Inhibiting Electrical Activity in Defined Neuronal Populations (2010) J. Biol. Chem. 285(20):14890-14897; and Sternson, S. M, et al. Chemogenetic Tools to Interrogate Brain Functions (2014) 37:387-407).

Chimeric ligand-gated ion channel proteins have ligand-binding domains and transmembrane ion channel domains from different proteins, either from the same or different species. In aspects, the protein is a chimeric protein comprising a LBD of a nicotinic acetylcholine receptor, such as a mutated ligand binding domain from the α7 nicotinic acetylcholine receptor. In one aspect, the chimeric protein is a chimeric protein described in one of U.S. Pat. No. 8,435, 762, or U.S. Patent Application Publication No. 2018/0009862, or International Patent Publication No. 2017/049252, each of which is incorporated herein by reference in its entirety for its technical disclosure of suitable chimeric proteins (modified LGICs) e.g., comprising a mutated α7 nicotinic acetylcholine receptor binding domain (ligand binding domain, LBD) fused to an ion pore domain (IPD), e.g., from a 5HT3, a GlyR, or a $GABA_C$ receptor, as well as for disclosure of other modified LGICs. Non-limiting examples of LGICs include, without limitation, Cys-loop receptors, e.g., AChR such as a nAChR, e.g., a muscle-type nAChR or a neuronal-type nAChR, gamma-aminobutyric acid (GABA; such as $GABA_A$ and $GABA_{A-p}$ (also referred to as $GABA_C$) receptors, GlyR, GluCl receptors, and 5HT3 receptors), ionotropic glutamate receptors (iGluR; such as AMPA receptors, kainate receptors, NMDA receptors, and delta receptors), ATP-gated channels (e.g., P2X), and phosphatidylinositol 4,5-bisphosphate (PIP2)-gated channels, and the modified LGIC can comprise sequences of any appropriate combination of LBD and ion channel of the preceding, modified be selective for an exogenous ligand. LBD sequences and transmembrane ion channel sequences may be obtained from any species, such as human, mouse, rat, sheep, cow, pig, or simian species, so long as it is functional for the intended use, for example, in humans, when used to produce a modified LGIC. The LGIC may be homomeric, or multimeric, comprising one or more LGIC subunits that can be the same or different.

In some aspects, a modified LGIC subunit described herein can include a LBD from a α7 nAChR. Exemplary amino acid sequences for α7-nicotinic acetylcholine receptor LBDs are provided in FIG. 2 (obtained from U.S. Patent Application Publication No. 2018/0009862). In various aspects, an α7-nicotinic acetylcholine receptor LBD is a homolog, orthologue, or paralog of the human an α7-nicotinic acetylcholine receptor LBD set forth in SEQ ID NO: 18, SEQ ID NO: 19, or SEQ ID NO: 20. In various aspects, an α7-nicotinic acetylcholine receptor LBD has at least 75 percent sequence identity (e.g., at least 80%, at least 82%, at least 85%, at least 88%, at least 90%, at least 93%, at least 95%, at least 97% or at least 99% sequence identity) to SEQ ID NO: 18, SEQ ID NO: 19, or SEQ ID NO: 20. Exemplary amino acid sequences for chimeric LGICs are provided in FIGS. 3A-3E (obtained from U.S. Patent Application Publication No. 2018/0009862). In various aspects, a modified LGIC has a sequence set forth in SEQ ID NO: 21, SEQ ID NO: 22, SEQ ID NO: 23, or SEQ ID NO: 24. In aspects, a modified LGIC has an amino acid sequence having at least 75 percent sequence identity (e.g., at least 80%, at least 82%, at least 85%, at least 88%, at least 90%, at least 93%, at least 95%, at least 97% or at least 99% sequence identity) to SEQ ID NO: 21, SEQ ID NO: 22, SEQ ID NO: 23, or SEQ ID NO: 24.

For purposes of generating a genetic construct for expressing these, or any amino acids, the nucleotide sequence of the ORF used can have any suitable sequence that can be translated to the desired amino acid sequence. Due to codon degeneracy, the nucleotide sequence can vary greatly, but codon usage may be the same or different from the natural gene, and can be optimized for increased, or optimal, expression.

In calculating percent sequence identity, two sequences are aligned and the number of identical matches of amino acid residues between the two sequences is determined. The number of identical matches is divided by the length of the aligned region (i.e., the number of aligned amino acid residues) and multiplied by 100 to arrive at a percent sequence identity value. The length of the aligned region can be a portion of one or both sequences up to the full-length size of the shortest sequence. Alignment of two or more sequences to determine percent sequence identity can be performed using the computer program ClustalW2 (EMBL-EBI) and default parameters, which calculates the best match between a query and one or more subject sequences, and aligns them.

FIGS. 3A-3E (excerpted from U.S. Patent Application Publication No. 2018/0009862) show exemplary amino acid sequences of chimeric LGICs. Mutation of amino acid residue 77 (e.g., W77F or W77Y) resulted in sensitivity to granisetron and tropisetron. Mutation of amino acid residue 79 (e.g., Q79G) was most effective for several agonists. Mutations of amino acid residue 131 (e.g., L131G, L131A, L131M, or L131N) altered sensitivity to varenicline, tropisetron, granisetron, and ACh. Potency was considerably enhanced when LBD mutations were combined with mutation at amino acid residue 298 in the GlyR or GABAC IPD. Potency was also enhanced when α7nAChR LBD mutations were combined with mutation at amino acid residue G175 and P216.

Specific, and non-limiting examples of modified LBDs of LGICs (relative to SEQ ID NOs: 18, 19, and 20) that change ligand binding specificity include, amino acid substitution at one or more of amino acid residues 77, 79, 115, 131, 139, 141, 175, 210, 216, 217, and 219, including, without limitation: W77F, W77Y, W77M, Q79A, Q79G, Q79C, Q79D, Q79E, Q79H, Q79L, Q79P, Q79R, Q79S, Q79T, Q79W, Y115F, Q139A, Q139C, Q139D, Q139F, Q139G, Q139H, Q1391, Q139K, Q139L, Q139M, Q139N, Q139R, Q139S, Q139V, Q139W, Q139Y, L141A, L141F, L141P, L141G, L141H, L141I, L141M, L141N, L141Q, L141S, L141V, L141W, G175K, G175A, G175F, G175H, G175M, G175R, G175S, G175V, P216I, and Y217F. In one aspect, the modified LBDs has the following combinations of point mutations: L131G and Q139L; L131G, Q139L, and Y217F; Q79G and L131G; L131G and Y217F; Q79S and L131G; or Q79S, L131G, and Q139L.

Point mutations that reduce binding to acetylcholine include Y115F, Q79R, Q139G, Q139V, Q139W, Q139Y, L141A, L141Q, L141S, can be combined with any of the selectivity-inducing mutations as described herein, such as Q79G and L141F. These modifications can be combined with amino acid substitutions to the ion channel domain that can alter conductance (See, U.S. Pat. No. 8,435,762 and U.S. Patent Application Publication No. 2018/0009862).

Various synthetic ligands, and the modified LGICs they bind to and activate, e.g., LGICs including modified α7nAChR LBDs are provided in, see, U.S. Pat. No. 8,435,762 and U.S. Patent Application Publication 2018/0009862 A1, as well in the priority application to the present application, U.S. Provisional Patent Application No. 62/473,630 filed Mar. 20, 2017, which is incorporated herein by reference in its entirety.

The exogenous LGIC ligand can be a synthetic exogenous LGIC ligand selected from the group consisting of a quinuclidine, a tropane, a 9-azabicyclo[3.3.1]nonane, a 6,7,8,9-tetrahydro-6,10-methano-6H-pyrazino(2,3-h)benzazepine, and a 1,4-diazabicyclo[3.2.2]nonane. When the synthetic exogenous LGIC ligand is a tropane, the tropane can be tropisetron, pseudo-tropisetron, nortropisetron, compound 723, compound 725, compound 737, or compound 745. When the synthetic exogenous LGIC ligand is a quinuclidine, the quinuclidine can be PNU-282987, PHA-543613, compound 0456, compound 0434, compound 0436, compound 0354, compound 0353, compound 0295, compound 0296, compound 0536, compound 0676, or compound 702. When the synthetic exogenous LGIC ligand is a 6,7,8,9-tetrahydro-6,10-methano-6H-pyrazino(2,3-h)benzazepine, the ligand can be compound 765 or compound 770. When the synthetic exogenous LGIC ligand is a 1,4-diazabicyclo[3.2.2]nonane, the ligand can be compound 773 or compound 774 (US 2018/0009862 A1).

Certain LGIC agonists associate increased potency with specific LBD substitutions in modified LGICs. FIG. 4A (from U.S. 2018/0009862 A1) shows LGIC agonists that exhibit enhanced potency with substituted α7nAChR LBD having a Q79G amino acid substitution. Additional LGIC agonists are shown in FIG. 4B (also excerpted from U.S. 2018/0009862 A1). For example, $\alpha7^{Q79G}$-GlyR$^{A298G}$ can be controlled by tropisetron, and $\alpha7^{L131G,Q139L,Y217F}$-GlyR can be controlled by varenicline. Further examples of modified LGICs include the ivermectin-responsive glutamate-gated chloride channels described in Weir et al., which were administered in AAV9 transducing particles intrathecally to mouse spinal cords (Weir et al., (2017) *Brain* 140; 2570-2585, see, also, Kynagh, T., et al., (2010) *J. Biol. Chem.* 285(20):14890-14897), and the ivermectin-responsive GlyR LGIC described in U.S. Pat. No. 8,957,036. Additional examples of the large number of known, specific modified LGICs and their specific agonists is beyond the scope of this disclosure, and is unnecessary.

According to one aspect of the invention, a method of modulating activity of excitable cells or secretory cells, such as nerve cells or neurons, e.g., to sensory neurons, e.g., depolarization or hyperpolarization of a neuron, in a patient is provided, comprising administering to an excitable cell or a secretory cell, such as a nerve cell or neuron of the patient a nucleic acid comprising a gene for expressing a modified LGIC that selectively binds, and is gated by an exogenous ligand to the cell, and where expression of the gene is under transcriptional control of a promoter specific to an excitable cell or a secretory cell, e.g., a sensory nerve cell or neuron, thereby expressing the modified LGIC in the cell, and administering the exogenous ligand to the patient, thereby activating the LGIC. The LGIC comprises an LBD and a transmembrane ion channel domain, for example and without limitation, according to any aspect described herein. Where hyperpolarization is desired, the modified LGIC comprises a transmembrane ion channel domain that is selective for Cl− or K+ ions, such as a GlyR or $GABA_A$ or $GABA_C$ ion channel domain. Where depolarization is desired, the modified LGIC comprises a transmembrane ion channel domain that is selective for $Na^+$ or $Ca^{2+}$ ions. In aspects, the LBD is an α7-nicotinic acetylcholine receptor LBD according to any aspect provided herein.

According to another aspect of the invention, a method of treating a disease or disorder associated with the nervous system in a patient. In one aspect, the disease or disorder associated with the nervous system is pain, such as chronic pain. In another aspect, the disease or disorder associated with the nervous system is itch. The method comprises administering to an excitable cell or a secretory cell of the patient, such as a nerve cell or neuron, e.g., to CNS cells, such as spinal cord cells or brain cells, such as a dorsal horn cell or a supraspinal cell, a nucleic acid comprising a gene for expressing a modified LGIC that selectively binds, and is gated by an exogenous ligand to the cell, and where expression of the gene is under transcriptional control of a promoter specific to a sensory neuron, thereby expressing the modified LGIC in the sensory neuron, and administering the exogenous ligand to the patent, thereby activating the LGIC. he LGIC comprises an LBD and a hyperpolarizing transmembrane ion channel domain introduced into an excitatory cell, or a depolarizing, excitatory transmembrane ion channel domain that is administered to inhibitory neurons. For example and without limitation, inhibitory ion channel domains according to any aspect described herein, include a transmembrane ion channel domain that is selective for Cl⁻ or K⁺ ions, such as a GlyR or $GABA_A$ or $GABA_C$ ion channel domain. For example and without limitation, excitatory ion channel domains according to any aspect described herein, include a transmembrane ion channel domain that is selective for Na⁺ or Ca⁺² ions, such as a 5HT3 ion channel domain. In aspects, the LBD is an α7-nicotinic acetylcholine receptor LBD according to any aspect provided herein. In aspects, the pain is localized chronic pain in a patient, such as from osteoarthritic conditions, surgical implants, wounds, scarring, fibrotic conditions, nerve damage, or disease, visceral pain, muscle or deep tissue damage, spinal cord injury, post herpetic neuralgia, metabolic disease such as diabetes, chemotherapeutic neuropathy, idiopathic peripheral neuropathy.

In methods of delivering nucleic acids encoding modified LGICs, according to any aspect described herein to a cell or to a patient, the nucleic acid may be delivered by any useful method, in any useful form, as is recognized by those of ordinary skill in the field of genetic therapies. The nucleic acid may be naked nucleic acid, such as a plasmid, deposited, for example and without limitation, by a colloidal drug delivery method, such as liposomes, e.g., cationic liposomes, or nanoparticles, or as part of a recombinant viral genome, as are broadly-known. In aspects, liposomes or nanoparticles comprising the nucleic acid are injected at a desired site, such as in or adjacent to specific neuronal tissue. In other aspects, a recombinant viral particle (transducing particle), is delivered, for example, injected, at a desired site, such as in or adjacent to, or otherwise targeting specific neuronal tissue. In one aspect, the nucleic acid comprising a gene for expressing the modified LGIC is an AAV (Adeno-Associated Virus) genome. In another aspect, the nucleic acid is injected into or adjacent to a tissue containing the target excitable or secretory cell, such as a CNS cell, e.g., a dorsal horn cell, a spinal cord cell, a brain cell, or a supraspinal cell. In another aspect, the nucleic acid is administered systemically, e.g., intravenously, and optionally in a delivery vehicle, such as an AAV particle that has a tropism to excitable or secretory cells, such as, for example and without limitation, AAV9, AAV-PHP.eB, AAV-PHP.S, or rAAV2-retro particles mentioned above, selective to brain, peripheral and/or spinal cord tissue. The nucleic acid may be injected once or more than once in order to establish sufficient expression of the modified LGIC in the target neuron cells. Suitable carriers or excipients for use in delivery of the nucleic acid, as are known in the related arts, may be included in the dosage form for delivery of the nucleic acid, such as in a liposomal or a recombinant viral transducing particle.

An "excipient" is an inactive substance used as a carrier for the active ingredients of a medication. Although "inactive," excipients may facilitate and aid in increasing the delivery, stability or bioavailability of an active ingredient in a drug product. Non-limiting examples of useful excipients include: antiadherents, binders, rheology modifiers, coatings, disintegrants, emulsifiers, oils, buffers, salts, acids, bases, fillers, diluents, solvents, flavors, colorants, glidants, lubricants, preservatives, antioxidants, sorbents, vitamins, sweeteners, etc., as are available in the pharmaceutical/compounding arts. For example, for delivery to a nerve cell by injection, a drug product might comprise the nucleic acid in the form of a viral particle, nanoparticle, or liposome, in a suitable solvent, such as saline or phosphate-buffered saline, and including a rheology modifier or thixotropic agent.

Suitable dosage forms for delivery of exogenous ligands as described herein, include, without limitation, oral, percutaneous, or inhaled dosage forms, the formulation of which is within the skill of an ordinary artisan (see, generally, Troy, D B, Editor, Remington: The Science and Practice of Pharmacy, 21st Ed., Lippincott Williams & Wilkins (2005), pp. 745-849, for descriptions of various compositions, solutions, and dosage forms useful for administration of the described compounds, as well as methods of making such compositions, solutions, and dosage forms). The exogenous ligand is delivered in an amount, and dosage regimen, effective to achieve a desired therapeutic end-point, such as lessening pain. Determination of safe and effective amounts of the exogenous ligand is routine, and within the skill of an ordinary artisan. Further, certain suitable exogenous ligands are approved for use for other indications, such as varenicline, or tropisetron, and as such suitable safe dosage ranges are already established in humans.

Example 1—Calretinin⁺ and CCK⁺ Neurons in the Dorsal Horn are Required for Persistent Pain Methods. Animals: All animals were kept on a standard 12:12 light/dark cycle in micro-isolator caging racks (Allentown Caging) with food and water provided ad libitum. Mouse strains obtained from Jackson Laboratories include C57Bl/6J (JAX #000664), $Calr^{Cre}$ (JAX #010774) and $CCK^{Cre}$ (JAX #012706). Adeno-associated viruses (AAV2/8) used in these experiments: hSyn-Flex-rev-$PSAM^{L141F}$-GlyR-IRES-eGFP ($7^{12}$ vg/ml) and hSyn-Flex-rev-$PSAM^{L141F,Y115F}$-GlyR-IRES-eGFP ($1.7^{13}$ vg/ml) were custom made by UNC Vector core based on plasmid material developed by Scott Sternson and provided by Addgene. The hSyn-Flex-rev-$PSAM^{L141F}$-GlyR-IRES-eGFP ($7^{12}$ vg/ml) was used in all experiments except FIG. 8 (e,f). For these experiments, hSyn-Flex-rev-$PSAM^{L141F,Y115F}$-GlyR-IRES-eGFP ($1.7^{13}$ vg/ml) was used. Methods including: intraspinal virus injections, paw withdrawal threshold to von Frey filaments, to cotton swab, Hargreaves, pinprick and acute pain behaviors licking, guarding, flicking are all as previously described (Peirs, C. et al. Dorsal Horn Circuits for Persistent Mechanical Pain. Neuron 87, 797-812 (2015); Seal, R. P. et al. Injury-induced mechanical hypersensitivity requires C-low threshold mechanoreceptors. Nature 462, 651-655, (2009)); For paw withdrawal threshold to pressure: mice were lightly restrained by hand such that their rear legs were allowed to freely hang. Using a Pressure Application Measurement device (Ugo Basile) the hind paw was grasped between the experimenter's forefinger and thumb (with pressure transducer on the thumb), and force was slowly applied to the paw until the mouse struggled or flicked its limb (paw withdrawal threshold, PWT). The final force in grams was recorded. Each mouse was tested on the left and right paw for three trials with a ten-minute inter-trial interval between applications, and the three results averaged for each paw. Injury Models including incision, complete Freund's adjuvant, spared nerve injury tibial and sural models, carrageenan, methylglyoxal and multi-dose streptozotocin are as previously described (Peirs, C. et al. Dorsal Horn Circuits for Persistent Mechanical Pain. Neuron 87, 797-812 (2015); Seal, R. P. et al. Injury-induced mechanical hypersensitivity requires C-low threshold mechanoreceptors. Nature 462, 651-655, (2009); Decosterd, I. and Woolf, C. J. Spared nerve injury: an animal model of persistent peripheral neuropathic pain. Pain 87, 149-158 (2000); Bierhaus, A. et al. Methylglyoxal modification of Nav1.8 facilitates nociceptive neuron firing and causes hyperalgesia in diabetic neuropathy. Nat Med 18, 926-933 (2012); Cavanaugh, D. J. et al. Distinct subsets of unmyelinated primary sensory fibers mediate behavioral responses to noxious thermal and mechanical stimuli. Proc Natl Acad Sci USA 106, 9075-9080, (2009)). Chemogenetic Activation of PSAM-GlyR Receptor: Behavior thresholds were performed as described above in AAV8-hSyn-DIO-PSAM-GlyR-IRES-GFP injected mice. PSEM$^{89S}$ at 30 mg/kg was injected intraperitoneally 15 minutes prior to testing. Immunohistochemistry was performed as previously described (Peirs, C. et al. Dorsal Horn Circuits for Persistent Mechanical Pain. Neuron 87, 797-812 (2015); Seal, R. P. et al. Injury-induced mechanical hypersensitivity requires C-low threshold mechanoreceptors. Nature 462, 651-655 (2009)). α-bungarotoxin conjugated to Alexa-647 (1:1000; ThermoFisher B35450), α-bungarotoxin conjugated to Alexa-488 (1:1000; ThermoFisher B13422). Imaging: Spinal cord sections were imaged with a confocal laser-scanning microscope (Nikon A1R) and Nikon Elements software using 405-, 488-, 561- and 640 nm excitation laser light. In order to suppress emission crosstalk, the microscope was configured to perform all scanning in sequential mode. Z-series were scanned at 20× magnification with an oil immersion lens and a z-step of 5.0 μm. Quantification and Statistical Analysis: all data are reported as mean±SEM. For acute behaviors, a two-tailed Student's t-test was used. The effect of chemogenetic activation on persistent pain behavior was analyzed by one-way repeated measures ANOVA with Bonferroni's Post hoc test. Significance was considered p<0.05. (*p<0.05, p<0.01, *p<0.001.) All quantitative analysis, graphs and statistical tests were performed on GraphPad Prism 7.0 (GraphPad).

Figure 5:
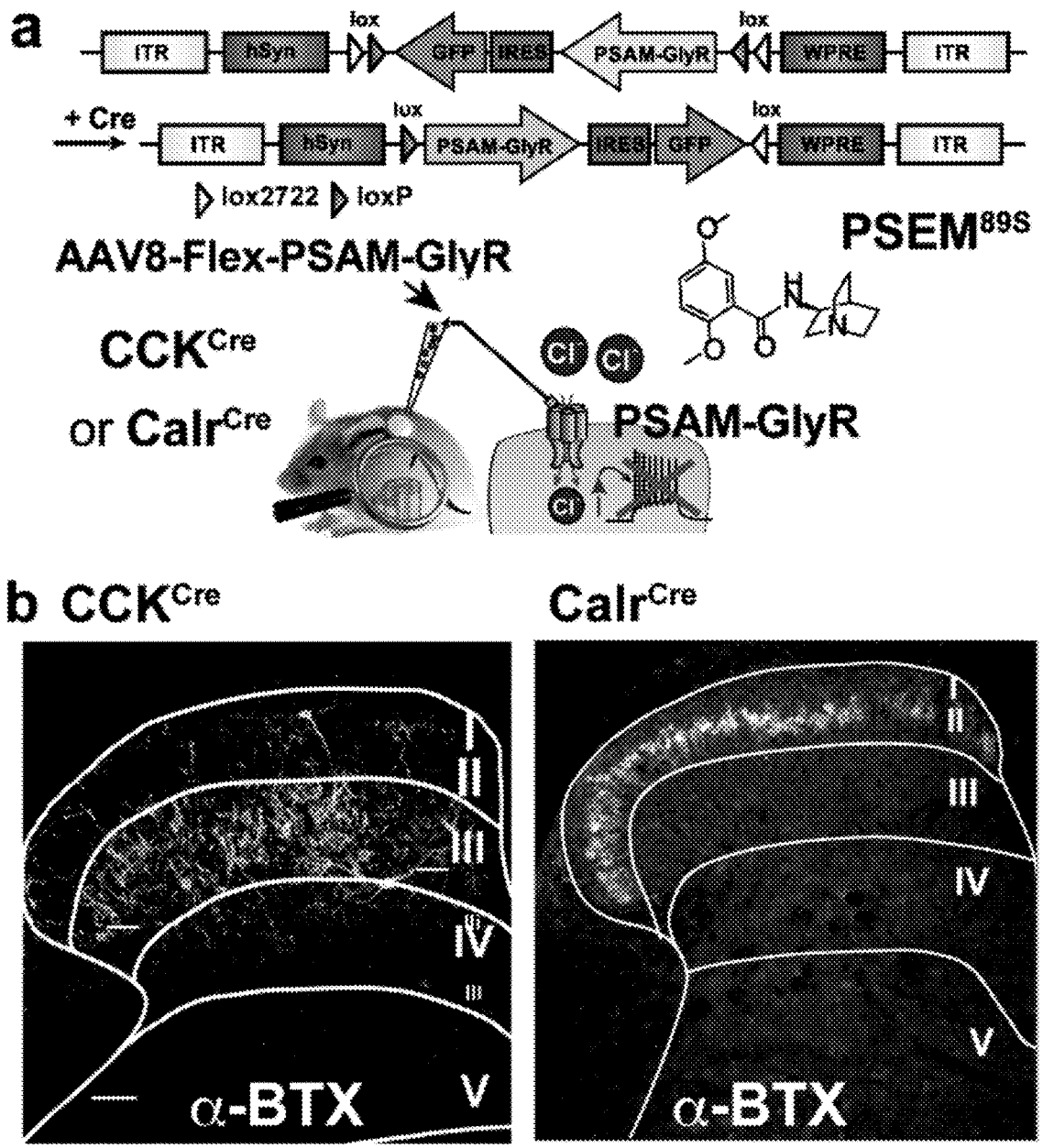
FIG. 5. (a) Cre-dependent construct for expressing PSAM-GlyR in neurons using AAV delivery. $PSEM^{89S}$ activates the PSAM-GlyR channel, preventing action potential firing of the cells expressing PSAM-GlyR. (b) Dorsal horns of $CCK^{Cre}$ and $Calr^{Cre}$ mice injected intraspinally with AAV8-Flex-PSAM-GlyR virus shows binding of alpha-bungarotoxin-Alexa647 (α-BTX-Alexa647) to PSAM-GlyR in patterns consistent with the distribution of these two genes.
Figure 6A:
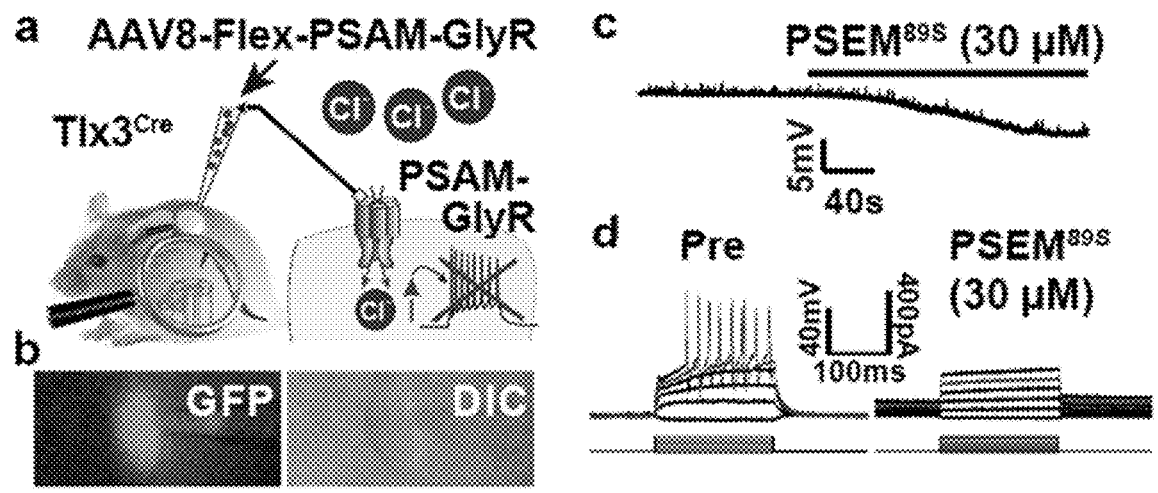
FIGS. 6A and 6B. Positive and negative controls for PSAM-GlyR and $PSEM^{89S}$. (a) Schematic of PSAM-GlyR construct with GFP reporter used to make AAV8-hSyn-Flex-PSAM-GlyR. Virus was injected into $Tlx3^{Cre}$ mice for electrophysiological slice recordings. (b) Electrode impaling a $GFP^+$ cell (also shown as DI, image) in a transverse slice of the dorsal horn from a $Tlx3^{Cre}$ mouse injected with AAV8-hSyn-Flex-PSAMGlyR virus. (c) Bath application of 30 μM $PSEM^{89S}$ induces a sustained hyperpolarization specifically in GFP-expressing cells. (d) Current injected into $GFP^+$ cell produces action potentials (Pre) that are completely blocked after application of $PSEM^{89S}$ (30 μM) to the slice. (e) Control for the specificity of α-BTX-Alexa647. Contralateral dorsal horn lacks staining for α-BTX-Alexa647. Calretinin (green in original); PKCγ. Scale bar=50 μm. Box indicates area of inset. (f) In mice lacking PSAM-GlyR, mechanical allodynia and heat hypersensitivity induced by the carrageenan pain model are not altered by injection of $PSEM^{89S}$ (30 mg/kg, i.p.) (p>0.999, n=4) (g) Punctate and dynamic allodynia induced by CFA are also not altered by injection of $PSEM^{89S}$ (p>0.999, n=6). (h) In the mice lacking PSAM-GlyR, punctate and dynamic allodynia induced by the sural-SNI model are not altered by injection of $PSEM^{89S}$ (30 mg/kg, i.p.) (n>0.999, n=6). Data are mean±standard error of the mean (SEM). ***P<0.001; ns=not significant (i.e. p>0.05)
Figure 8:
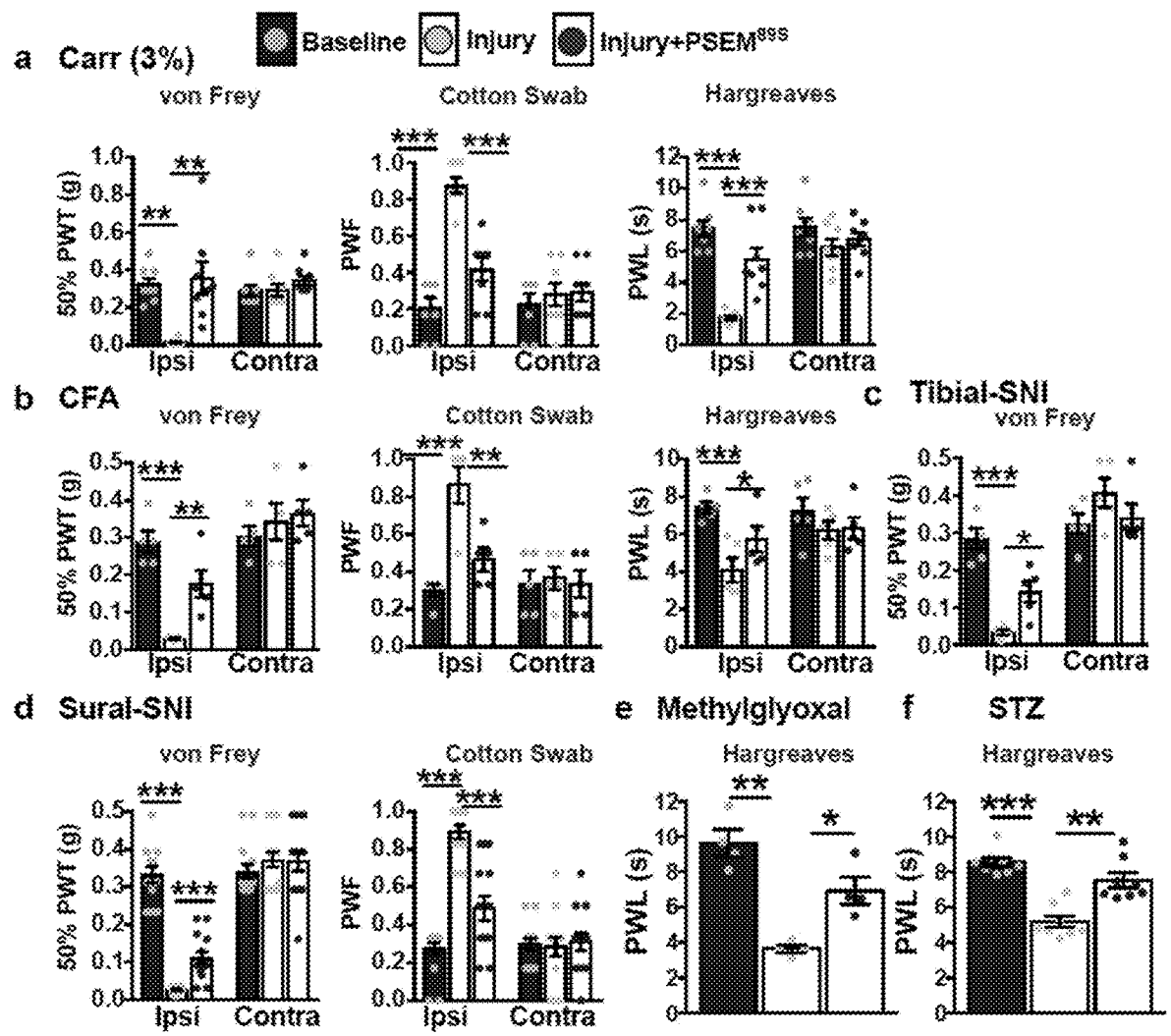
FIG. 8. $CCK^+$ excitatory dorsal horn neurons are required for the transmission of persistent forms of pain. Mice expressing PSAM-GlyR in $CCK^+$ dorsal horn neurons were tested in persistent pain behaviors. (a) In the carrageenan pain model, injection of $PSEM^{89S}$ (30 mg/kg, i.p.) reversed punctate (p=0.0017, n=8) and dynamic allodynia (p=0.0001, n=8) as well as heat hypersensitivity (p=0.0002, n=8). (b) In the CFA model, $PSEM^{89S}$ injection also markedly reversed punctate (p=0.0034, n=5) and dynamic allodynia (p=0.0016, n=5) as well as heat hypersensitivity (p=0.0368, n=5). (c,d) Inhibiting the CCK population reversed punctate allodynia in the sural-SNI (p=0.0003, n=12) and tibial-SNI (p=0.0054, n=5) models. Dynamic allodynia in sural-SNI is also reversed (p=0.0001, n=12). (e,f) $PSEM^{89S}$ also reversed heat hypersensitivity induced by MG (p=0.0272, n=4) or multi-dose STZ (p=0.010, n=9). Data are mean±SEM. *p<0.05, p<0.01, *P<0.001.
Figure 10:
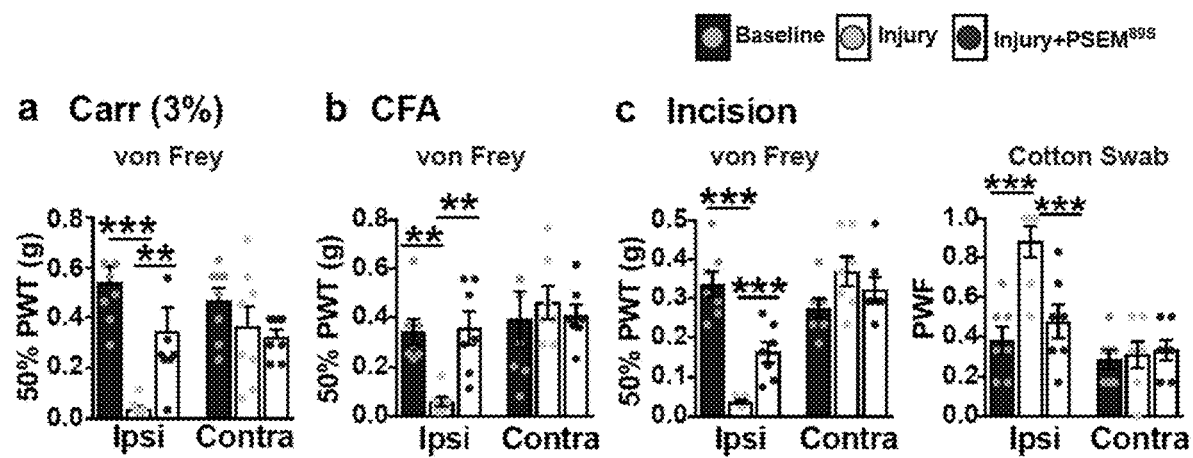
FIG. 10. $Calretinin^+$ excitatory neurons in lamina II of the dorsal horn convey mechanical allodynia induced by inflammatory, but not neuropathic pain models. Inhibition of PSAM-GlyR expressing calretinin neurons in the dorsal horn lamina II by injection of $PSEM^{89S}$ (30 mg/kg, i.p.) reverses mechanical allodynia induced by models of inflammatory pain including (a) carrageenan (p=0.0074, n=8), (b) CFA (p=0.0026, n=8), (c) incision (punctate, p=0.0028, n=7; dynamic p=0.0001, n=7) Data are mean±SEM. p<0.01, *P<0.001.

Results. To determine the role of calretinin and cholecystokinin (CCK) excitatory dorsal horn neurons in persistent pain and baseline somatosensory behavior, we used the designer ligand-gated anion channel, PSAM-GlyR (FIGS. 5, 8, and 10), which allowed us to acutely and reversibly inhibit these specific populations of neurons. Somatosensory behavior was tested under chemogenetic control at baseline and after the induction of inflammatory and neuropathic pain models (FIGS. 8 and 10). The inhibitory designer receptor, PSAM-GlyR[16], is engineered such that a mutated ligand-binding domain of the human α-7 nicotinic receptor is fused to the anion channel domain of the human glycine receptor (FIG. 5(a), that is, FIG. 1, panel (a)) (Magnus, C. J. et al. Chemical and genetic engineering of selective ion channel-ligand interactions. *Science* 333, 1292-1296, (2011)). This mutated receptor binding domain no longer recognizes physiological levels of acetylcholine, but instead binds the synthetic ligand PSEM$^{89S}$ with high affinity. To selectively target the CCK and Calretinin neurons in the dorsal horn, a Cre-dependent adeno-associated virus (AAV) encoding PSAM-GlyR (AAV8-hSyn.FLEX.PSAM-GlyR.IRES.EGFP) was injected unilaterally into the dorsal horn of P21 CCK$^{Cre}$ or Calretinin$^{Cre}$ mice (FIG. 5(b)). Four weeks later, receptor expression was examined by staining spinal cord slices with α-bungarotoxin conjugated to Alexa Fluor-647 (α-BTX-Alexa647), which specifically recognizes the ligand binding domain of α-7 nicotinic acetylcholine receptors, including the ligand binding domain of PSAM-GlyR (FIG. 5(b)). Expression of PSAM-GlyR was largely limited to laminae III-IV (FIG. 5(b)) and did not overlap with PKCγ (PKCγ staining not shown). Specificity of α-BTX-Alexa647 staining for the exogenously expressed PSAM-GlyR was demonstrated by the lack of staining observed in the contralateral dorsal horn (FIG. 6e).

In Vitro and In Vivo Controls for the Specific Actions of PSEM89S on PSAM-GlyR

Figure 6B:
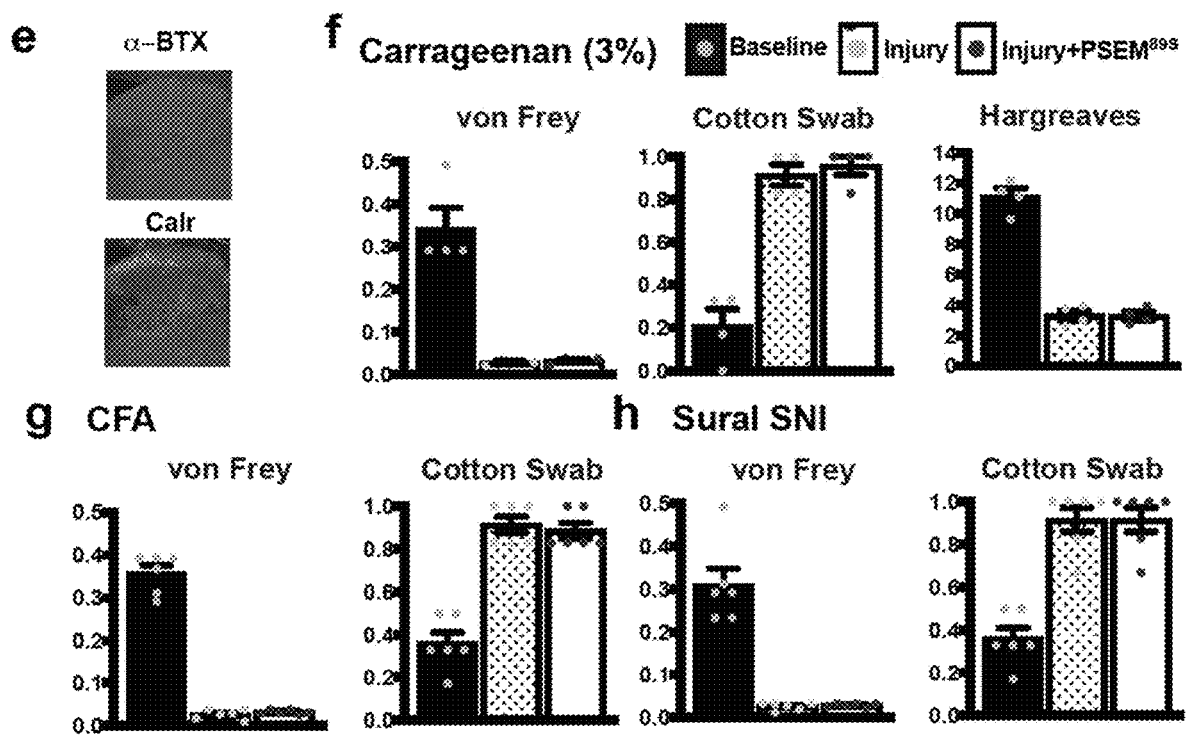

Prior to assessing the role of the neurons in somatosensory behavior, the ability of PSAM-GlyR to inhibit excitatory interneurons in the dorsal horn was tested using electrophysiological recordings in spinal cord slices. AAV8-Flex-PSAM-GlyR was injected intraspinally into the dorsal horn of P16 Tlx3$^{Cre}$ mice. In this mouse line, the recombinase is strictly expressed by excitatory neurons located throughout laminae I-III. Three weeks later, neuronal excitability was measured using patch clamp electrophysiology in spinal cord slices in the presence and absence of PSEM$^{89S}$ (FIG. 6(a-d)). To identify PSAM-GlyR$^+$ neurons, we identified cells expressing green fluorescent protein (GFP), which is also encoded by the PSAM-GlyR viral construct (FIG. 6(a,b)). Application of PSEM$^{89S}$ (30 μM) to spinal cord slices significantly decreased the membrane potential (−7.3±3.4 mV, n=3 cells from 2 mice) and blocked action potentials generated by current injection in GFP$^+$ (FIG. 6(c,d)), but not GFP$^-$ neurons (data not shown). We also tested the effect of the ligand PSEM$^{89S}$ on pain behavior in mice lacking the receptor (FIG. 6(f,h)). PSEM$^{89S}$ injection had no effect on mechanical allodynia or heat hypersensitivity in the carrageenan, complete Freund's adjuvant or SNI pain model, suggesting the drug alone has no unintended behavioral effects.

CCK$^+$ Dorsal Horn Neurons are Required for Conveying Persistent Pain, but not Baseline Somatosensory Behavior.

Figure 7:
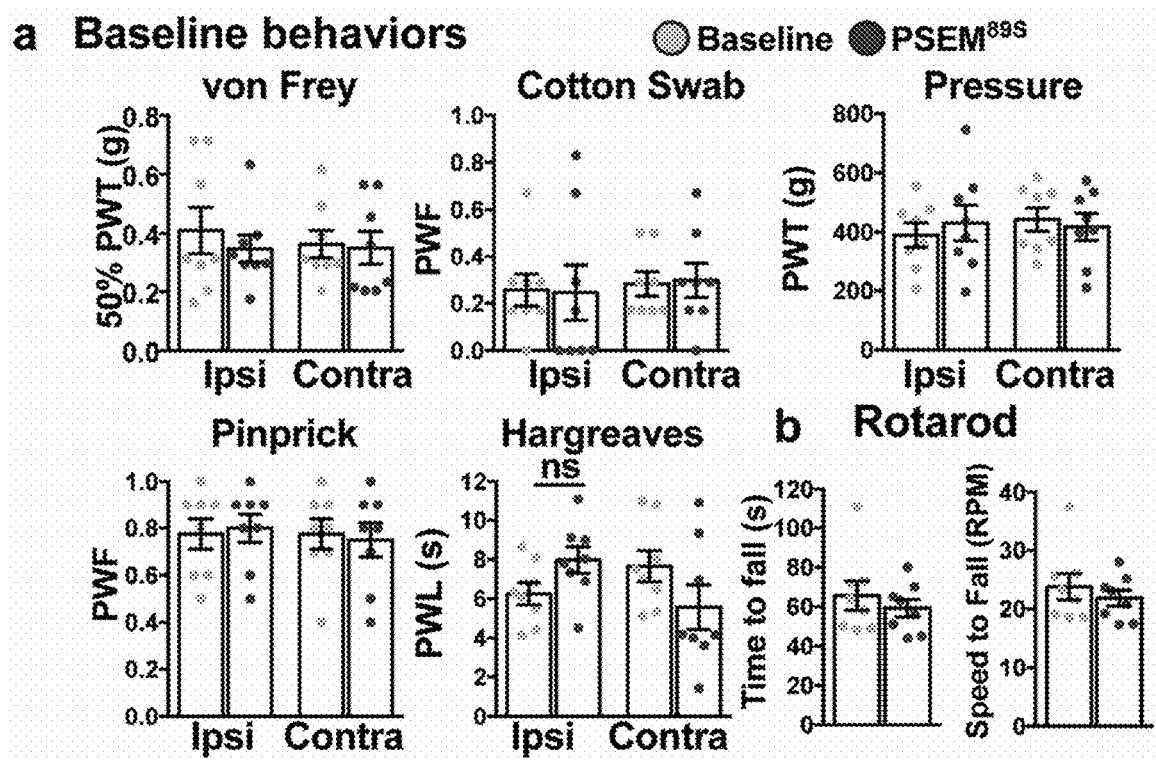
FIG. 7. $CCK^+$ excitatory neurons in the dorsal horn primarily lamina III-IV are not required for baseline somatosensory behavior or motor behavior on rotarod. (a) Injection of $PSEM^{89S}$ into $CCK^{Cre}$ mice expressing PSAM-GlyR ipsilaterally in the dorsal horn has no effect on baseline von Frey threshold (p=0.2192, n=8), response to cotton swab (p=0.7293, n=8), pressure with calibrated calipers (p=0.7450, n=8) or pinprick (p=0.5983, n=8). Hargreaves latencies are unchanged (p=0.9746, n=8). (b) Performance on the rotarod is also not altered by injection of $PSEM^{89S}$. Data are mean±SEM. None are significantly different.

Three weeks after unilateral injection of AAV8-hSyn-Flex-PSAM-GlyR in the dorsal horn of CCK$^{Cre}$ mice, we tested the effect of inhibiting the dorsal horn CCK neurons on baseline somatosensory behavior using von Frey threshold, cotton swab assay, pinprick assay, pressure test and Hargreaves assay (FIG. 7). We also tested motor behavior using rotarod (FIG. 7). All behaviors were normal and similar to the contralateral hindpaw (FIG. 7). We next tested the effect of inhibiting the dorsal horn CCK neurons on persistent pain in the carrageenan model of inflammatory pain. PSEM$^{89S}$ injection significantly reversed punctate and dynamic mechanical allodynia as well as heat hypersensitivity (FIG. 8(a)). Similarly, using the more chronic inflammatory model, complete Freund's adjuvant (CFA), PSEM$^{89S}$ injection again significantly reversed both punctate and dynamic allodynia (FIG. 8(b)) as well as heat hypersensitivity. Injection of PSEM$^{89S}$ (30 mg/kg, i.p.) into mice lacking the receptor showed no effect on CFA-induced persistent pain (FIG. 6(g)). In the sural-SNI model of neuropathic pain, PSEM$^{89S}$ injection significantly reversed both punctate and dynamic allodynia (FIG. 8(c)). Similarly, in the tibial-SNI model of neuropathic pain, PSEM$^{89S}$ injection markedly reversed punctate allodynia (FIG. 8(d)).

We have shown here that the CCK population is essential for the transmission of carrageenan and CFA-induced heat hypersensitivity, but is dispensable for normal heat sensibility. Because heat hypersensitivity also develops in diabetic neuropathic pain models, we tested whether the CCK neurons are also required in this type of pain. Indeed, acute inhibition of the CCK population markedly reversed the heat hypersensitivity induced by methylglyoxal (MG) treatment as well as the heat hypersensitivity induced by the multi-dose STZ model of diabetic neuropathy (FIG. 8(e,f)). These data reveal for the first time an essential role for CCK excitatory dorsal horn neurons in conveying punctate and dynamic mechanical allodynia induced by inflammatory and neuropathic pain models. This population also has an important role in conveying heat hypersensitivity induced by inflammatory and polyneuropathic pain models.

Figure 9:
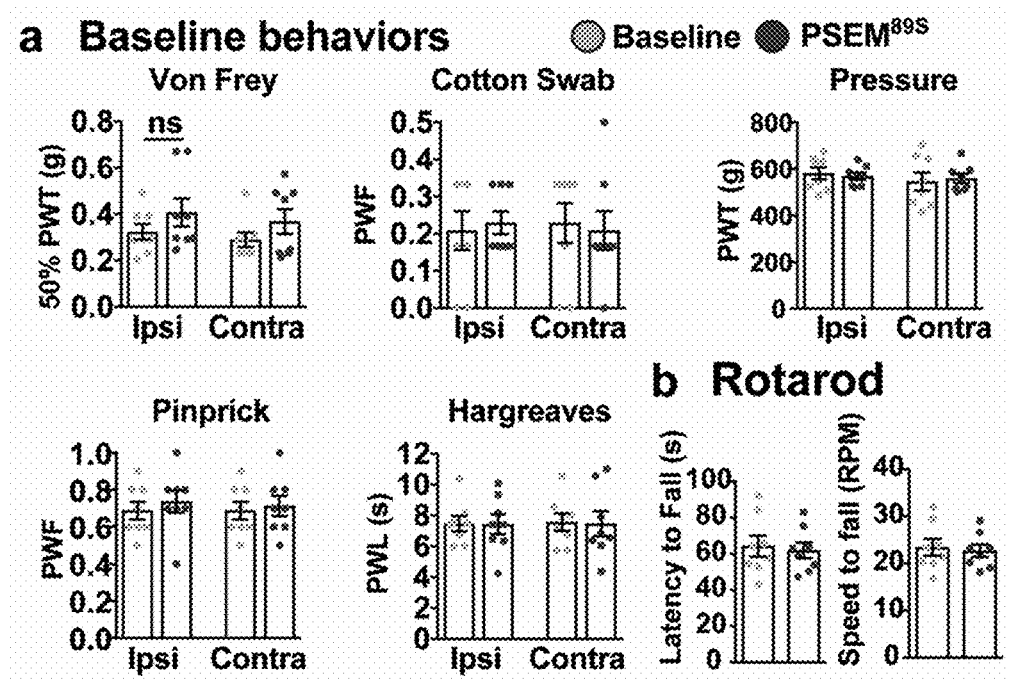
FIG. 9. $Calretinin^+$ excitatory neurons in the dorsal horn lamina II are not required for baseline somatosensory behavior or motor behavior on the rotarod. (a) Injection of $PSEM^{89S}$ (30 mg/kg, i.p.) into $Calr^{Cre}$ mice expressing PSAM-GlyR ipsilaterally in the dorsal horn has no effect on ipsilateral von Frey threshold (p=0.3988, n=8), response to cotton swab (p=0.7963, n=8), pressure with calibrated calipers (p=0.8350, n=8) sticky tape (p=0.9346, n=8) or pinprick (p=0.7689, n=8). Hargreaves latencies are also unchanged (p=0.6125, n=8). (b) Motor behavior measured by rotarod is not altered by inhibition of dorsal horn calretinin neurons with $PSEM^{89S}$. Data are mean±SEM. None are significantly different.

Calretinin neurons in lamina II of the dorsal horn are required for conveying mechanical allodynia induced by inflammatory injuries. Here we show that calretinin expressing neurons in inner lamina II of the dorsal horn are required for conveying mechanical allodynia induced by inflammatory injury. We unilaterally injected Cre-dependent AAV8 PSAM-GlyR into the dorsal horn of $Calr^{Cre}$ mice at P21 (FIGS. 5 and 10). Similar to what was observed when expressing the excitatory designer receptor in this population, neurons expressing PSAM-GlyR were restricted to inner lamina II (FIG. 5(b)) and co-localized with calretinin, but not PKCγ (not shown). Baseline measures of mechanical and heat sensitivity showed no change after injection of $PSEM^{89S}$ at either the ipsilateral or contralateral hindpaw. Motor behavior was also normal after $PSEM^{89S}$ injection (FIGS. 9(a,b)). We next tested whether the calretinin neurons are required for conveying mechanical allodynia or heat hypersensitivity in the carrageenan model of inflammatory pain. Injection of $PSEM^{89S}$ 24 hours after carrageenan injection significantly reversed punctate mechanical allodynia (FIG. 10(a)). We also tested whether the neurons are required for mechanical allodynia in the CFA model. Measured 5 days after injection of the inflammatory agent, injection of $PSEM^{89S}$ resulted in a complete reversal of punctate mechanical allodynia at the ipsilateral hindpaw (FIG. 10(b)). To determine how generalizable the requirement for calretinin neurons is in conveying mechanical allodynia induced by inflammatory pain models, we tested the incision model of post-operative pain (FIG. 10(c)). Inhibition of the calretinin neurons also significantly reversed mechanical allodynia in this model. The data collected from a number of inflammatory pain models show that dorsal horn neurons expressing calretinin are required for conveying mechanical allodynia induced by inflammatory injuries.

Discussion Work shown here demonstrates that targeting of a designer ligand-gated anion channel (in this case PSAM-GlyR) to neurons that express CCK⁺ or calretinin⁺ in the dorsal horn markedly attenuates mechanical allodynia and/or heat hypersensitivity caused by models of inflammatory and neuropathic pain when the receptor is activated by the designer ligand (in this case $PSEM^{89}S$). The data also demonstrate that $PSEM^{89S}$ and PSAM-GlyR mediated inhibition of the neurons does not affect baseline mechanical or thermal sensitivity. Finally, the data demonstrate that the ligand alone (i.e. in the absence of the receptor) does not affect mechanical or thermal sensitivity either before or after inflammatory or neuropathic injury. Therefore, the data suggest that inhibition of these neurons is sufficient to block persistent mechanical and heat pain.

Figure 11:
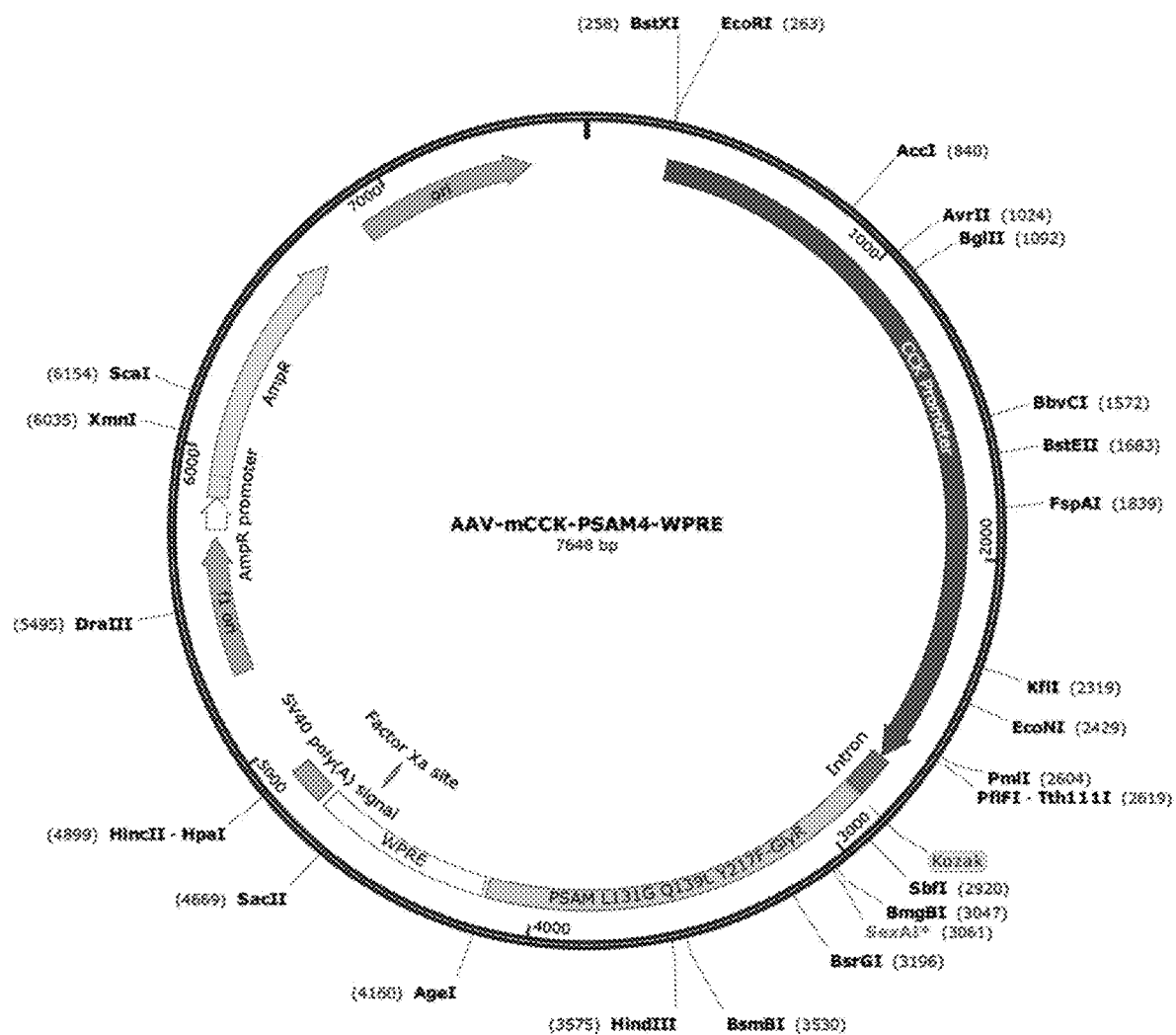
FIG. 11: AAV-mCCK-PSAM4-WPRE construct. A 2.5 kb fragment of the mouse CCK promoter was sub-cloned upstream of the PSAM (L131G Q139L Y217F)-GlyR (PSAM4) gene with a chimeric intron (135 bp) located in between the promoter and the PSAM4 gene.

Example 2—Mechanical Allodynia Induced by Inflammatory and Neuropathic Pain Models is Attenuated by Injection of Varenicline in Mice with mCCK-PSAM4 Delivered to the Dorsal Horn As further proof of concept, a varenicline-responsive PSAM-GlyR receptor mutant that was directly under the transcriptional control of a CCK promoter and delivered to the dorsal horn was shown to markedly attenuate mechanical allodynia in persistent pain models. The mouse cholecystokinin (CCK) promoter with an added chimeric intron to drive expression of $\alpha 7^{L131G, Q139L, Y217F}$ GlyR (PSAM4) was packaged into AAV2/8 and injected into the dorsal horn of 3-week-old wildtype C57Bl/6 male and female mice. Injection of AAV into the dorsal horn was performed as described previously (Peirs, C. et al. Dorsal Horn Circuits for Persistent Mechanical Pain. Neuron 87, 797-812 (2015)). See FIG. 11 for a schematic of the plasmid used to produce these rAAV particles. Briefly, a 2.5 kb fragment of the mouse CCK promoter was subcloned upstream of the PSAM4 gene with the chimeric intron (135 bp) located in between. This construct expressed in AAV8 is sufficient to drive expression in neurons in the deep dorsal horn.

Figure 12:
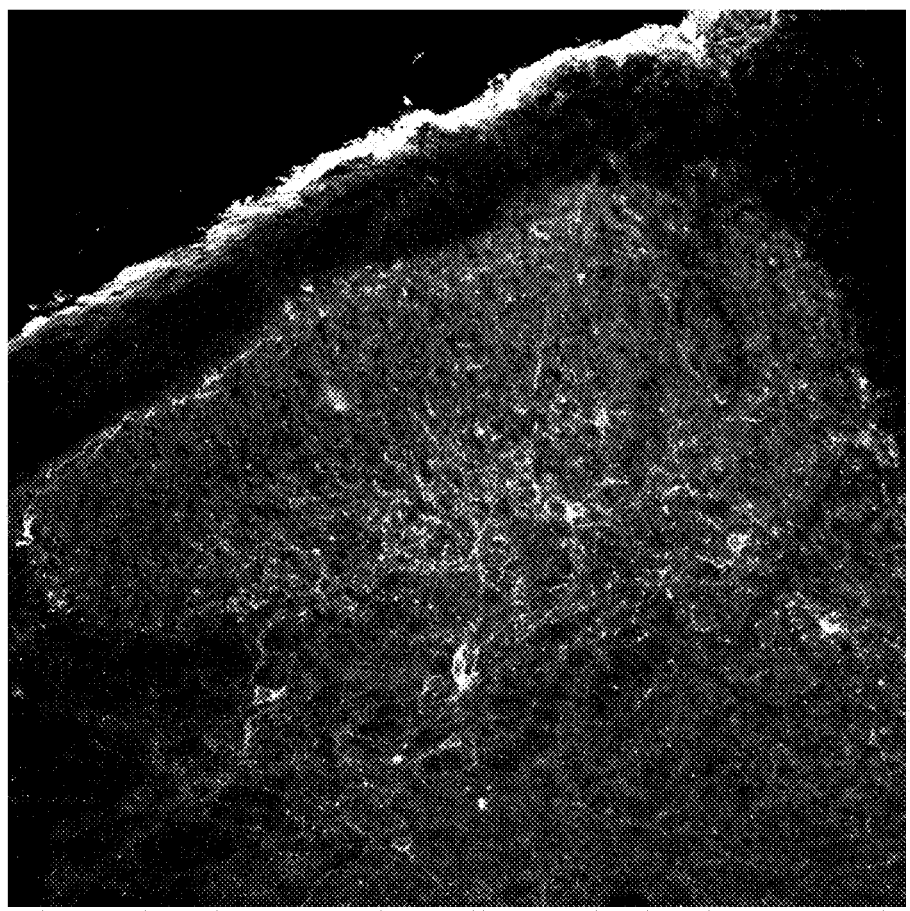
FIG. 12. Expression of PSAM4 in the dorsal horn of an adult wildtype C57Bl/6 mouse. α-bungarotoxin-Alexa647 (α-BTXAlexa-647) staining of the lumbar dorsal horn of a mouse unilaterally injected with the AAV8 mCCK-PSAM4-WPRE virus in the dorsal horn ($1^{13}$ vg/ml, custom packaged).

Expression of the PSAM4 in the dorsal horn was examined by immunostaining for α-BTX-Alexa647 (FIG. 12). α-BTX-Alexa647 staining was observed in cells in the deep dorsal horn below the PKCγ layer (PKCγ staining not shown). This expression pattern is similar to the pattern for CCK mRNA in the dorsal horn detected by in situ hybridization (Allen Spinal Cord Atlas) and by injecting AAV8 hSyn-Flex-PSAM-GlyR virus in the dorsal horn of $CCK^{Cre}$ mice (see FIG. 5(a)).

Varenicline has no effect on mechanical or heat sensitivity at baseline or after CFA or sural-SNI in the absence of PSAM4. Mechanical and heat hypersensitivity was tested in adult wildtype male and female C57Bl/6 mice (not injected with mCCK-PSAM4 virus) before and after intraperitoneal injection of (i.p) varenicline (0.1 milligram per kilogram (mpk) (FIG. 13). We also tested these parameters before and 2-5 days after induction of the complete Freund's adjuvant (CFA)-model of inflammatory pain and 7 days after induction of the sural version of the spared nerve injury (SNI) model of neuropathic pain (FIG. 13). Sensitivity to mechanical stimuli was tested by measuring the paw withdrawal threshold to von Frey filaments (PWT) and the paw withdrawal response to a cotton swab (percentage of response) as described previously (Peirs, C. et al. Dorsal Horn Circuits for Persistent Mechanical Pain. Neuron 87, 797-812 (2015)). Heat sensitivity was tested by measuring the withdrawal latency to a radiant heat source using the Hargreaves apparatus (PWL) as described previously (Peirs, C. et al. Dorsal Horn Circuits for Persistent Mechanical Pain. Neuron 87, 797-812 (2015)). As shown in FIG. 13, injection of varenicline (0.1 mpk, i.p) had no effect on baseline PWT, response frequency or PWL in uninjured mice (measured 30-60 minutes after injection). Injection of varenicline also had no effect on mechanical or heat hypersensitivity 3 and 2 days, respectively, after induction of CFA or 7 days after induction of sural-SNI models.

PSAM4 Ligands have No Effect on Baseline Mechanical or Heat Sensitivity, but Reverse Mechanical Allodynia Induced by CFA and SNI in Mice with Targeted Expression of PSAM4 in CCK⁺ Neurons of the Dorsal Horn.

Figure 14:
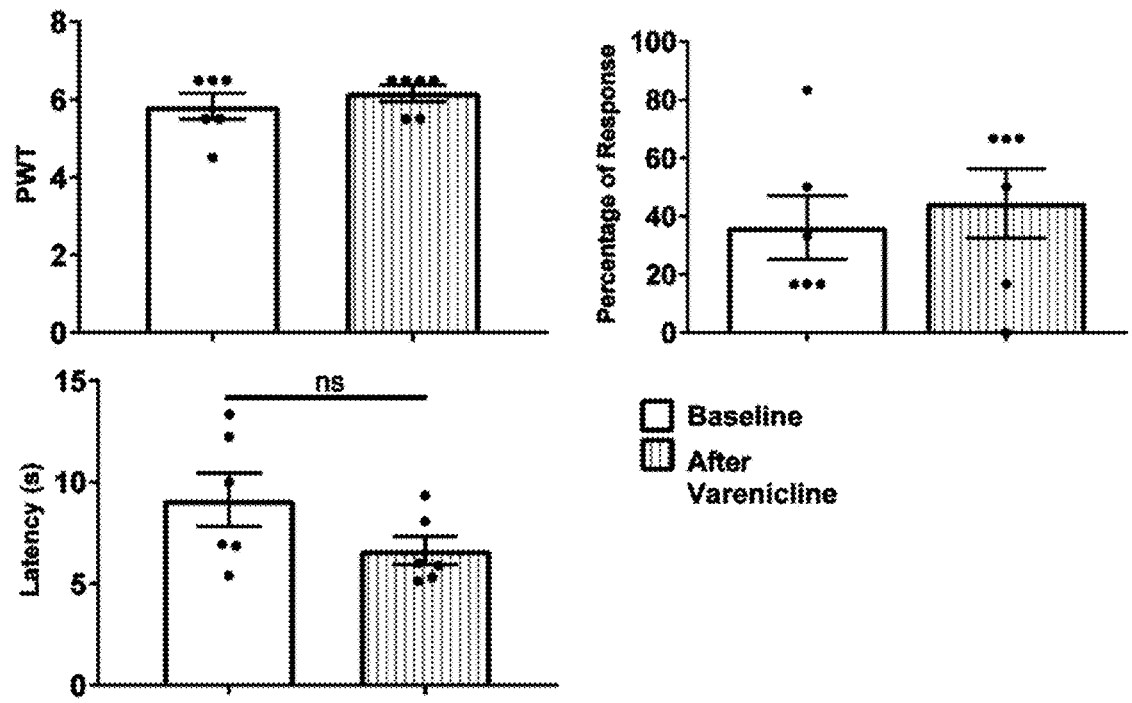
FIG. 14. Control showing effect of varenicline on mechanical and heat sensitivity at baseline in mice injected with mCCK-PSAM4 virus. The effect of varenicline (0.3 mpk, i.p) on baseline mechanical and heat hypersensitivity was tested 2 weeks after injection of AAV8 mCCK-PSAM4 unilaterally into the dorsal horn. Injection of varenicline had no effect on baseline PWT, percentage response or PWL (measured 30-60 minutes following injection of the drug) in mice expressing PSAM4 in dorsal horn CCK+ neurons. Data are mean±SEM. N=5-6 mice. p<0.05, p<0.01, ***P<0.001; ns=not significant (i.e. p>0.05).
Figure 15:
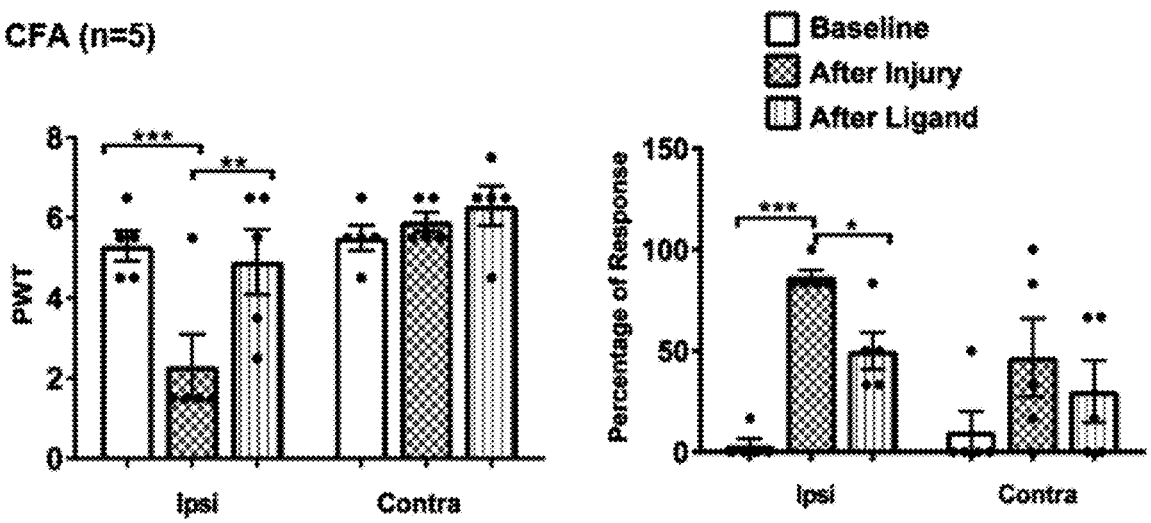
FIG. 15. Varenicline reverses mechanical allodynia induced by CFA in mice expressing mCCK-PSAM4 in the dorsal horn. Adult wildtype C57Bl/6 mice injected with AAV8 mCCK-PSAM4-WPRE virus unilaterally in the dorsal horn. PWT to von Frey filaments and percentage of response to cotton swab were measured before and 3 days after CFA injection in plantar hindpaw and after injection of varenicline (0.3 mpk, i.p). Injection of varenicline reversed both PWT and response frequency to cotton swab after CFA. Data are mean±SEM. N=5 mice. *p<0.05, p<0.01, *P<0.001.
Figure 16:
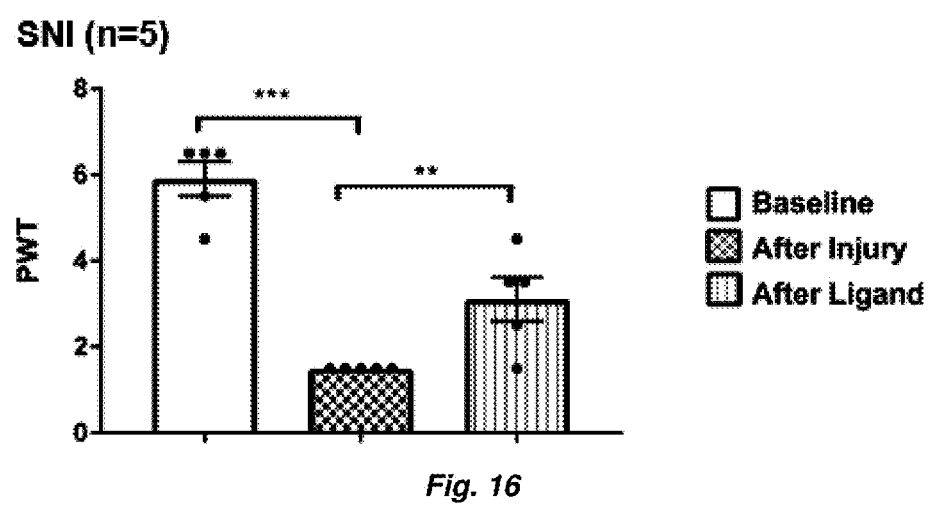
FIG. 16. Varenicline reverses mechanical allodynia induced by the sural model of SNI in mice expressing mCCK-PSAM4 in the dorsal horn. Adult wildtype C57Bl/6 mice injected with mCCK-PSAM4 unilaterally in the dorsal horn. Three weeks later, PWT to von Frey filaments was measured before and 7 days after sural-SNI surgery on the ipsilateral side and then again after injection of varenicline (0.3 mpk, i.p). Injection of varenicline reversed PWT after SNI. Data are mean±SEM. N=5 mice. p<0.01, *p<0.001.

Mice were injected unilaterally in the dorsal horn with AAV8 mCCK-PSAM4 virus and tested two weeks later. As shown in FIG. 14, varenicline (0.3 mpk, i.p.) did not alter baseline PWTs, response frequencies or PWLs. Thus, inhibition of the dorsal horn CCK⁺ neurons does not alter mechanical or heat sensitivity. The ipsilateral plantar hindpaw of the mice was injected with CFA and PWTs and response frequencies tested 3 days later in the absence and presence of varenicline (0.3 mpk, i.p.). As shown in FIG. 15, varenicline (0.3 mpk, i.p.) markedly reversed both PWT and response frequency after CFA. As shown in FIG. 16, varenicline (0.3 mpk, i.p.) markedly reversed the PWT when measured 7 days following sural spared nerve injury. These results are similar to what we observed with $PSEM^{89S}$ and PSAM-GlyR in FIGS. 7 and 8.

The following numbered clauses provide illustrative examples of aspects of the invention:

1. A nucleic acid comprising a gene for expressing a modified ligand-gated ion channel, comprising an open reading frame encoding a modified ligand-gated ion channel under transcriptional control of transcriptional control elements governing cell-specific expression in CNS neurons, such as dorsal horn neurons, spinal cord cells, or brain cells, or in inhibitory neurons or nerve cells, such as a CCK promoter, a Tac1 promoter, an NTS promoter, an NMU promoter, a Calb1 promoter, an SST promoter, a GRPR promoter, a parvalbumin promoter, a Gal promoter, an NPY promoter, a PKCγ promoter or Calb2 promoter, wherein the modified ligand-gated ion channel comprises a modified ligand binding domain activatable by an exogenous ligand, and optionally selective to the exogenous ligand, and an ion pore domain.
2. The nucleic acid of clause 1, wherein transcription of the modified ligand-gated ion channel is controlled at least in part by a CCK promoter, an SST promoter, a GRPR promoter, a Tac1 promoter, an NTS promoter, an NMU promoter, a Calb1 promoter, a parvalbumin promoter, a Gal promoter, an NPY promoter, a Calb2 promoter or a PKCγ promoter.
3. The nucleic acid of clause 1, wherein transcription of the modified ligand-gated ion channel is controlled at least in part by a CCK promoter, a Calb2 promoter, or a PKCγ promoter.
4. The nucleic acid of clause 1, wherein transcription of the modified ligand-gated ion channel is controlled at least in part by a CCK promoter.
5. The nucleic acid of any one of clauses 1-3, wherein the transcription control element comprises a human promoter sequence.
6. The nucleic acid of clause 5, wherein the transcription control element is a promoter having at least 75 percent sequence identity to a sequence set forth in SEQ ID NOs: 1-17.
7. The nucleic acid of any one of clauses 1-6, wherein the modified ligand binding domain is a modified α7 nicotinic acetylcholine ligand binding domain.
8. The nucleic acid of clause 7, wherein the modified α7 nicotinic acetylcholine ligand binding domain comprises a sequence having at least 75 percent sequence identity to a sequence set forth in SEQ ID NO: 18, SEQ ID NO: 19, or SEQ ID NO: 20.
9. The nucleic acid of clause 7, wherein the modified α7 nicotinic acetylcholine ligand binding domain comprises an amino acid substitution at one or more of amino acid residues 77, 79, 115, 131, 139, 141, 175, 210, 216, 217, and 219.
10. The nucleic acid of clause 7, wherein the modified α7 nicotinic acetylcholine ligand binding domain comprises an amino acid substitution at one or more of amino acid residues 77, 79, 115, 139, and 141, such as Q79A, Q79G, L141A, L141F, L141P, W77F, W77Y, and W77M.
11. The nucleic acid of clause 7, wherein the modified α7 nicotinic acetylcholine ligand binding domain comprises:
a L131G amino acid substitution, a Q139L amino acid substitution, and a Y217F amino acid substitution;
a W77F amino acid substitution, a Q79G amino acid substitution, and a G175K amino acid substitution;
a Q79G amino acid substitution, a Y115F amino acid substitution, and a G175K amino acid substitution;
a Y115F amino acid substitution and a G175K amino acid substitution;
a Q79G amino acid substitution and a 216I amino acid substitution; or
a R27D amino acid substitution and/or a E41R amino acid substitution.
12. The nucleic acid of clause 7, wherein the modified α7 nicotinic acetylcholine ligand binding domain comprises a L131G amino acid substitution, a Q139L amino acid substitution, and a Y217F amino acid substitution.
13. The nucleic acid of clause 7, wherein the modified α7 nicotinic acetylcholine ligand binding domain has reduced binding with endogenous acetylcholine (ACh) as compared to unmodified α7-nAChR LBD.
14. The nucleic acid of clause one of clauses 1-13, wherein the ion pore domain is anion-selective, or cation-selective, and optionally is an ion pore domain of an ionotropic nicotinic acetylcholine receptor, an ionotropic serotonin receptor, an ionotropic glycine receptor, or an ionotropic GABA receptor.
15. The nucleic acid of any one of clauses 1-13, wherein the ion pore domain is an ion pore domain from a serotonin 3 receptor (5HT3) ion pore domain, a glycine receptor (GlyR) ion pore domain, a gamma-aminobutyric acid (GABA) receptor ion pore domain, or an α7 nicotinic acetylcholine receptor ion pore domain.
16. The nucleic acid of clause 15, wherein the ion pore domain is a GlyR ion pore domain comprising an amino acid substitution at residue 298.
17. The nucleic acid of clause 16, wherein the GlyR ion pore domain comprising an A298G amino acid substitution.
18. The nucleic acid of clause 1, wherein the exogenous ligand is selected from the group consisting of a quinuclidine, a tropane, a 9-azabicyclo[3.3.1]nonane, a 6,7,8,9-tetrahydro-6,10-methano-6H-pyrazino(2,3-h)benzazepine, and a 1,4-diazabicyclo[3.2.2]nonane.
19. The nucleic acid of any one of clauses 1-18, comprising a sequence of a packageable viral genome comprising the gene for expressing a modified ligand-gated ion channel.
20. The nucleic acid of clause 19, comprising Adeno-associated virus ITR sequences flanking the gene for expressing a modified ligand-gated ion channel, producing a sequence of a packageable recombinant AAV genome or a self-complementary AAV genome comprising the gene for expressing a modified ligand-gated ion channel.
21. A method of modulating (increasing or decreasing) the membrane potential of an excitable cell or a secretory cell, comprising expressing in the cell a genetic construct comprising a gene for expressing a modified ligand-gated ion channel, comprising an open reading frame encoding a modified ligand-gated ion channel under transcriptional control of transcriptional control elements governing cell-specific expression in CNS neurons, such as dorsal horn neurons, spinal cord cells, or brain cells, or in inhibitory neurons or nerve cells, such as a CCK promoter, a Tac1 promoter, an NTS promoter, an NMU promoter, a Calb1 promoter, an SST promoter, a GRPR promoter, a parvalbumin promoter, a Gal promoter, an NPY promoter, a PKCγ promoter, or Calb2 promoter and a modified ligand-gated ion channel comprising a modified ligand binding domain activatable by an exogenous ligand, and optionally selective to the exogenous ligand, and an ion pore domain, and contacting the cell with an amount of the exogenous ligand effective to activate the modified ligand gated ion channel thereby modulating the membrane potential of the cell.

22. The method of clause 21, wherein transcription of the modified ligand-gated ion channel is controlled at least in part by a CCK promoter, an SST promoter, a GRPR promoter, a Tac1 promoter, an NTS promoter, an NMU promoter, a Calb1 promoter, a parvalbumin promoter, a Gal promoter, an NPY promoter, Calb2 promoter or a PKCγ promoter.

23. The method of clause 21, wherein transcription of the modified ligand-gated ion channel is controlled at least in part by a CCK promoter, a Calb2 promoter, or a PKCγ promoter.

24. The method of clause 21, wherein transcription of the modified ligand-gated ion channel is controlled at least in part by a CCK promoter.

25. The method of any one of clauses 21-24, wherein the transcription control element comprises a human promoter sequence.

26. The method of clause 25, wherein the transcription control element is a promoter having at least 75 percent sequence identity to a sequence set forth in SEQ ID NOs: 1-17.

27. The method of any one of clauses 21-26, wherein the modified ligand binding domain is a modified α7 nicotinic acetylcholine ligand binding domain.

28. The method of clause 27, wherein the modified α7 nicotinic acetylcholine ligand binding domain comprises a sequence having at least 75 percent sequence identity to a sequence set forth in SEQ ID NO: 18, SEQ ID NO: 19, or SEQ ID NO: 20.

29. The method of clause 27, wherein the modified α7 nicotinic acetylcholine ligand binding domain comprises an amino acid substitution at one or more of amino acid residues 77, 79, 115, 131, 139, 141, 175, 210, 216, 217, and 219.

30. The method of clause 27, wherein the modified α7 nicotinic acetylcholine ligand binding domain comprises an amino acid substitution at one or more of amino acid residues 77, 79, 115, 139, and 141, such as Q79A, Q79G, L141A, L141F, L141P, W77F, W77Y, and W77M.

31. The method of clause 27, wherein the modified α7 nicotinic acetylcholine ligand binding domain comprises:
a L131G amino acid substitution, a Q139L amino acid substitution, and a Y217F amino acid substitution;
a W77F amino acid substitution, a Q79G amino acid substitution, and a G175K amino acid substitution;
a Q79G amino acid substitution, a Y115F amino acid substitution, and a G175K amino acid substitution;
a Y115F amino acid substitution and a G175K amino acid substitution;
a Q79G amino acid substitution and a 216I amino acid substitution; or
a R27D amino acid substitution and/or a E41R amino acid substitution.

32. The method of clause 27, wherein the modified α7 nicotinic acetylcholine ligand binding domain comprises a L131G amino acid substitution, a Q139L amino acid substitution, and a Y217F amino acid substitution, and, optionally, the exogenous ligand is varenicline.

33. The method of clause 27, wherein the modified α7 nicotinic acetylcholine ligand binding domain has reduced binding with endogenous acetylcholine (ACh) as compared to unmodified α7-nAChR LBD.

34. The method of clause one of clauses 21-33, wherein the ion pore domain is an ion pore domain of an ionotropic nicotinic acetylcholine receptor, an ionotropic serotonin receptor, an ionotropic glycine receptor, or an ionotropic GABA receptor.

35. The method of any one of clauses 21-33, wherein the ion pore domain is anion-selective, or cation-selective, and optionally is an ion pore domain from a serotonin 3 receptor (5HT3) ion pore domain, a glycine receptor (GlyR) ion pore domain, a gamma-aminobutyric acid (GABA) receptor ion pore domain, or an α7 nicotinic acetylcholine receptor ion pore domain.

36. The method of clause 35, wherein the ion pore domain is a GlyR ion pore domain comprising an amino acid substitution at residue 298.

37. The method of clause 36, wherein the GlyR ion pore domain comprising an A298G amino acid substitution.

38. The method of clause 37, wherein the exogenous ligand-gated ion channel ligand is selected from the group consisting of a quinuclidine, a tropane, a 9-azabicyclo[3.3.1]nonane, a 6,7,8,9-tetrahydro-6,10-methano-6H-pyrazino(2,3-h)benzazepine, and a 1,4-diazabicyclo[3.2.2]nonane.

39. The method of any one of clauses 21-38, comprising a sequence of a packageable viral genome comprising the gene for expressing a modified ligand-gated ion channel.

40. A method of treating a disease or disorder associated with the nervous system in a patient comprising: delivering a nucleic acid according to any one of clauses 1-20 to the patient, and administering the exogenous ligand to the patient in an amount effective to activate the modified ligand gated ion channel in a patient thereby treating the disease or disorder associated with the nervous system in the patient.

41. The method of clause 40, wherein the disease or disorder associated with the nervous system is itch.

42. The method of clause 40, wherein the disease or disorder associated with the nervous system is chronic pain, and transcription of the modified ligand-gated ion channel is controlled at least in part by a CCK promoter, an SST promoter, a GRPR promoter, a Tac1 promoter, an NTS promoter, an NMU promoter, a Calb1 promoter, a parvalbumin promoter, a Gal promoter, an NPY promoter, a Calb2 promoter or a PKCγ promoter.

43. The method of clause 25, wherein transcription of the modified ligand-gated ion channel is controlled at least in part by a CCK promoter, a calb2 promoter, or a PKCγ promoter.

44. The method of any one of clauses 40-43, wherein the nucleic acid comprising the gene for expressing a modified ligand-gated ion channel is delivered to the patient as a recombinant AAV transducing particle.

45. The method of any one of clauses 40-44, wherein the exogenous ligand is selected from the group consisting of a quinuclidine, a tropane, a 9-azabicyclo[3.3.1]nonane, a 6,7,8,9-tetrahydro-6,10-methano-6H-pyrazino(2,3-h)benzazepine, and a 1,4-diazabicyclo[3.2.2]nonane.

While the present invention is described with reference to several distinct aspects or embodiments, those skilled in the art may make modifications and alterations without departing from the scope and spirit. Accordingly, the above detailed description is intended to be illustrative rather than restrictive.

What is claimed is:

1. A method of treating persistent pain in a patient comprising:

delivering to the dorsal horn of the spinal cord of the patient a nucleic acid comprising a gene for expressing a modified ligand-gated ion channel, comprising an open reading frame encoding a modified ligand-gated ion channel under transcriptional control of transcriptional control elements governing cell-specific expression in dorsal horn neurons, wherein the modified ligand-gated ion channel comprises a modified ligand binding domain activatable by an exogenous ligand, and an ion pore domain, wherein the modified ligand-gated ion channel is a modified α7 nicotinic acetylcholine ligand binding domain comprising:
 a. a L131G amino acid substitution, a Q139L amino acid substitution, and a Y217F amino acid substitution;
 b. a W77F amino acid substitution, a Q79G amino acid substitution, and a G175K amino acid substitution;
 c. a Q79G amino acid substitution, a Y115F amino acid substitution, and a G175K amino acid substitution;
 d. a Y115F amino acid substitution and a G175K amino acid substitution;
 e. a Q79G amino acid substitution and a P216I amino acid substitution; or
 f. a R27D amino acid substitution and/or a E41R amino acid substitution, wherein the transcriptional control element is a promoter sequence having at least 75% sequence identity with the sequence of one of SEQ ID NOs: 1-17, wherein the ion pore domain is a GlyR ion pore domain comprising an A298G amino acid substitution; and administering an exogenous ligand to the patient in an amount effective to activate the modified ligand gated ion channel in the patient, thereby treating the disease or disorder associated with the nervous system in the patient.

2. The method of claim 1, wherein the modified α7 nicotinic acetylcholine ligand binding domain has reduced binding with endogenous acetylcholine (ACh) as compared to unmodified α7-nAChR LBD.

3. The method of claim 1, wherein the exogenous ligand is selected from the group consisting of a quinuclidine, a tropane, a 9-azabicyclo [3.3.1] nonane, a 6,7,8,9-tetrahydro-6,10-methano-6H -pyrazino(2,3-h)benzazepine, and a 1,4-diazabicyclo[3.2.2] nonane.

4. The method of claim 1, wherein the nucleic acid comprises a sequence of a packageable viral genome comprising the gene for expressing a modified ligand-gated ion channel.

5. The method of claim 1, wherein the nucleic acid comprises Adeno-associated virus ITR sequences flanking the gene for expressing a modified ligand-gated ion channel.

* * * * *

UNITED STATES PATENT AND TRADEMARK OFFICE
CERTIFICATE OF CORRECTION

| | | |
|---|---|---|
| PATENT NO. | : 11,713,470 B2 | Page 1 of 1 |
| APPLICATION NO. | : 16/493387 | |
| DATED | : August 1, 2023 | |
| INVENTOR(S) | : Rebecca Seal et al. | |

It is certified that error appears in the above-identified patent and that said Letters Patent is hereby corrected as shown below:

In the Drawings

Figure 2, Sheet 16, Line 5, delete "21" and insert -- 18 --

Figure 2, Sheet 16, Line 10, delete "22" and insert -- 19 --

Figure 2, Sheet 16, Line 15, delete "23" and insert -- 20 --

Signed and Sealed this
Thirty-first Day of October, 2023

Katherine Kelly Vidal
*Director of the United States Patent and Trademark Office*